United States Patent
Han et al.

(10) Patent No.: US 11,241,503 B2
(45) Date of Patent: Feb. 8, 2022

(54) OXADIAZOLE LINKERS AND USE THEREOF

(71) Applicant: NewBio Therapeutics, Inc., Shanghai (CN)

(72) Inventors: Nianhe Han, Shanghai (CN); Deqiang An, Shanghai (CN); Di Zeng, Shanghai (CN); Baoxiang Wang, Shanghai (CN); Huali Li, Shanghai (CN); Hang Chen, Shanghai (CN); Chun Yang, Shanghai (CN)

(73) Assignee: NewBio Therapeutics, Inc., Shanghai (CN)

( * ) Notice: Subject to any disclaimer, the term of this patent is extended or adjusted under 35 U.S.C. 154(b) by 203 days.

(21) Appl. No.: 16/629,885

(22) PCT Filed: Jun. 4, 2018

(86) PCT No.: PCT/CN2018/089767
§ 371 (c)(1),
(2) Date: Jan. 9, 2020

(87) PCT Pub. No.: WO2019/011078
PCT Pub. Date: Jan. 17, 2019

(65) Prior Publication Data
US 2021/0154320 A1    May 27, 2021

(30) Foreign Application Priority Data
Jul. 10, 2017 (CN) .......................... 201710556847.1

(51) Int. Cl.
*A61K 47/68* (2017.01)
*C07D 271/113* (2006.01)
*C07K 16/32* (2006.01)

(52) U.S. Cl.
CPC ...... *A61K 47/6889* (2017.08); *A61K 47/6803* (2017.08); *A61K 47/6851* (2017.08); *C07D 271/113* (2013.01); *C07K 16/32* (2013.01); *C07K 2317/73* (2013.01); *C07K 2317/92* (2013.01)

(58) Field of Classification Search
None
See application file for complete search history.

(56) References Cited

FOREIGN PATENT DOCUMENTS

| CN | 103864711 A | 6/2014 |
|---|---|---|
| WO | 2014144878 A2 | 9/2014 |
| WO | 2016059611 A2 | 4/2016 |

OTHER PUBLICATIONS

Search Report in corresponding International Application No. PCT/CN2018/089767, dated Aug. 24, 2018.

*Primary Examiner* — Joseph R Kosack
(74) *Attorney, Agent, or Firm* — Edell, Shapiro & Finnan, LLC

(57) ABSTRACT

The present invention is directed to oxadiazole linkers and use thereof, more specifically to the compounds represented by formula I, II, and III, and their use in the preparation of antibody-drug conjugates (ADCs). The ADCs obtained from said oxadiazole linkers have high homogeneity and stability, and could be used effectively for the treatment of various diseases including tumors. The definition of the groups in formula I, II, and III is the same as that in the description.

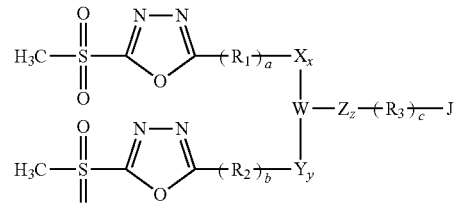

I

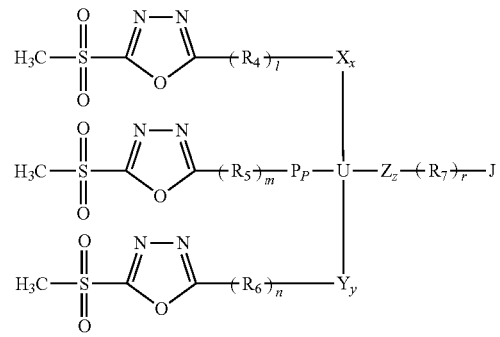

II

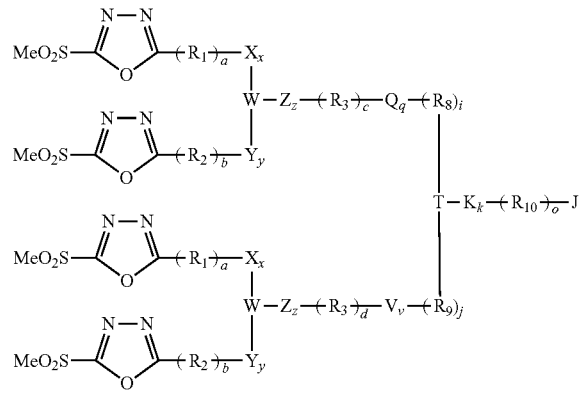

III

57 Claims, 8 Drawing Sheets

OXADIAZOLE LINKERS AND USE THEREOF

CROSS REFERENCE TO RELATED APPLICATIONS

This application is a National Phase application of International Application No. PCT/CN2018/089767, filed on Jun. 4, 2018, which claims priority under 35 U.S.C. § 119 to Application No. CN 201710556847.1 filed on Jul. 10, 2017, the contents of each of which are hereby incorporated by reference in their entireties.

FIELD OF THE INVENTION

The invention relates to novel oxadiazole linkers, antibody-drug conjugates prepared from these oxadiazole linkers, and use of the antibody-drug conjugates in the treatment of tumors and other diseases.

BACKGROUND OF THE INVENTION

Antibody-drug conjugates (ADCs) are a kind of novel targeted therapeutic agents for the treatment of cancer, auto-immune and inflammation diseases. ADC is composed of three independent parts, an antibody or antibody-like ligand, small-molecule drugs, and linkers that conjugate the drugs to the ligand. The mechanism of action (MOA) of an antibody-drug conjugate is as follows. An antibody or antibody-like ligand specifically recognizes and binds to the cell surface antigens. Once binding to the antigens, the binding complex will be internalized and thus deliver the linked drugs into the cell. The antibody or antibody-like ligand will be digested by enzymes, or the linkers will be cleaved, thereby the high-potency cytotoxic drugs could be released in an active form and kill the cells.

In traditional ADC structures, high-potency cytotoxic drugs are normally linked to the ε-amino group of lysine residues or cysteine residues after full/partial reduction of interchain disulfide bonds via bifunctional linkers. The optimized DAR (Drug/Antibody Ratio) is 2~4. The large number of ε-amino groups of lysine residues (~80/mAb) and the non-selective conjugation mode result in the uncertainty of conjugation sites and conjugated drug numbers, and thus afford ADC product with high heterogeneity. For example, Kadcyla™ (ad-trastuzumab emtansine) with average DAR~3.5 has a DAR distribution ranging from 0 to 8 (Rapid Commun. Mass Spectrum. 2005, 19, 1806-1814). Similarly, when cysteine residues are selected as conjugation sites, although there are only four reducible interchain disulfide bonds in the antibody, they should be partially reduced in order to provide ADCs with optimal average DAR (2~4) (Bioconjugate Chem. 2005, 16, 1282-1290). As existing reducing agents (DTT, TCEP, etc) cannot selectively reduce the interchain disulfide bonds, the conjugation products thus obtained are not homogeneous and contain multi-conjugates with DAR of 0, 2, 4, 6 and 8. Even for a fraction with specific DAR value, it is a mixture that contains conjugates with drugs conjugated at different sites. The heterogeneity of ADC products may ultimately lead to different PK, efficacy, and toxicity properties. For example, the conjugates with higher DAR have been reported, in some cases, to clear more rapidly and contribute to more severe toxicity (Bioconjugate Chem. 2011, 22, 1994-2004).

To overcome the above mentioned shortcomings of traditional linker technologies, new linker technology is highly needed to provide site-specific conjugation products with higher homogeneity.

SUMMARY OF THE INVENTION

The present invention intends to provide a novel oxadiazole linker that can be used to produce ADCs via chemical coupling methods, and ADCs prepared via said linkers, as well as their use in the treatment of various diseases including tumors.

In the first aspect, the invention provides a compound of formula I,

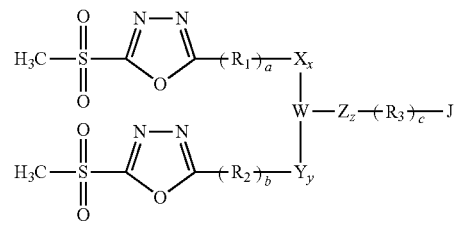

and pharmaceutically acceptable salt thereof,
wherein
W is selected from N, $CR_{11}$ and aryl;
X, Y and Z are each independently selected from O, $C(=O)$, $C(=O)NR_{12}$, $NR_{13}C(=O)$, $NR_{14}C(=O)NR_{15}$, $NR_{16}C(=O)O$ and $OC(=O)NR_{17}$;
J is selected from —COOH, —OH and —$NHR_{18}$;
a, b, c, x, y and z are each independently selected from 0 and 1;
$R_1$, $R_2$ and $R_3$ are each independently selected from $C_1$-$C_8$ alkylene and $C_1$-$C_8$ alkylene containing O in the backbone;
$R_{11}$, $R_{12}$, $R_{13}$, $R_{14}$, $R_{15}$, $R_{16}$, $R_{17}$ and $R_{18}$ are each independently selected from H and $C_1$-$C_8$ alkyl.

In a preferred embodiment, the invention provides a compound of formula I and pharmaceutical acceptable salt thereof, wherein
W is selected from N, CH and $C_6$-$C_{10}$ aryl, preferably phenyl.

In another preferred embodiment, the invention provides a compound of formula I and pharmaceutical acceptable salt thereof, wherein
a, b, x and y are all 0; or
a is 0, b is 1, while x and y are 0; or
a is 1, b is 0, while x and y are 0; or
a and b are 1, while x and y are 0; or
a and b are 1, while x and y are 1.

In another preferred embodiment, the invention provides a compound of formula I and pharmaceutical acceptable salt thereof, wherein
c is 0 or 1.

In another preferred embodiment, the invention provides a compound of formula I and pharmaceutical acceptable salt thereof, wherein
$R_1$ and $R_2$ are each independently selected from $C_1$-$C_4$ alkylene and $C_1$-$C_4$ alkylene containing O in the backbone.

In another preferred embodiment, the invention provides a compound of formula I and pharmaceutical acceptable salt thereof, wherein
$R_3$ is selected from $C_1$-$C_8$ alkylene and $C_1$-$C_8$ alkylene containing O in the backbone.

In another preferred embodiment, the invention provides a compound of formula I and pharmaceutical acceptable salt thereof, wherein
Z is selected from O, $C(=O)$, $C(=O)NR_{12}$ and $NR_{13}C(=O)$.

In another preferred embodiment, the invention provides a compound of formula I and pharmaceutical acceptable salt thereof, wherein
J is —COOH.

In another aspect, the invention provides a compound of formula II,

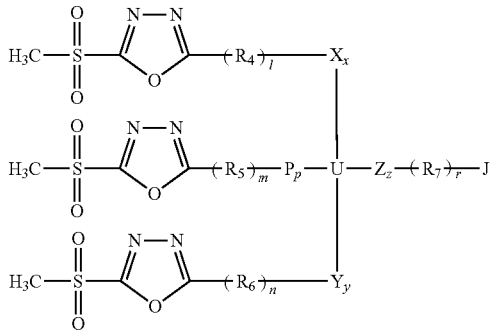

and pharmaceutically acceptable salt thereof,
wherein
U is selected from C and aryl;
X, Y, P and Z are each independently selected from O, C(=O), C(=O)NR$_{12}$, NR$_{13}$C(=O), NR$_{14}$C(=O)NR$_{15}$, NR$_{16}$C(=O)O and OC(=O)NR$_{17}$;
J is selected from —COOH, —OH and —NHR$_{18}$;
l, m, n, r, x, y and z are each independently selected from 0 and 1;
R$_4$, R$_5$, R$_6$ and R$_7$ are each independently selected from C$_1$-C$_8$ alkylene and C$_1$-C$_8$ alkylene containing O in the backbone;
R$_{12}$, R$_{13}$, R$_{14}$, R$_{15}$, R$_{16}$, R$_{17}$ and R$_{18}$ are each independently selected from H and C$_1$-C$_8$ alkyl.

In a preferred embodiment, the invention provides a compound of formula II and pharmaceutical acceptable salt thereof, wherein
U is C$_6$-C$_{10}$ aryl, preferably phenyl.

In another preferred embodiment, the invention provides a compound of formula II and pharmaceutical acceptable salt thereof, wherein
X, Y and P are each independently selected from O, C(=O), C(=O)NR$_{12}$ and NR$_{13}$C(=O).

In another preferred embodiment, the invention provides a compound of formula II and pharmaceutical acceptable salt thereof, wherein
Z is selected from O, C(=O), C(=O)NR$_{12}$ and NR$_{13}$C(=O).

In another preferred embodiment, the invention provides a compound of formula II and pharmaceutical acceptable salt thereof, wherein
R$_4$, R$_5$ and R$_6$ are each independently selected from C$_1$-C$_4$ alkylene and C$_1$-C$_4$ alkylene containing O in the backbone.

In another preferred embodiment, the invention provides a compound of formula II and pharmaceutical acceptable salt thereof, wherein
R$_7$ is selected from C$_1$-C$_8$ alkylene and C$_1$-C$_8$ alkylene containing O in the backbone.

In another preferred embodiment, the invention provides a compound of formula II and pharmaceutical acceptable salt thereof, wherein
J is —COOH.

In another aspect, the invention provides a compound of formula III,

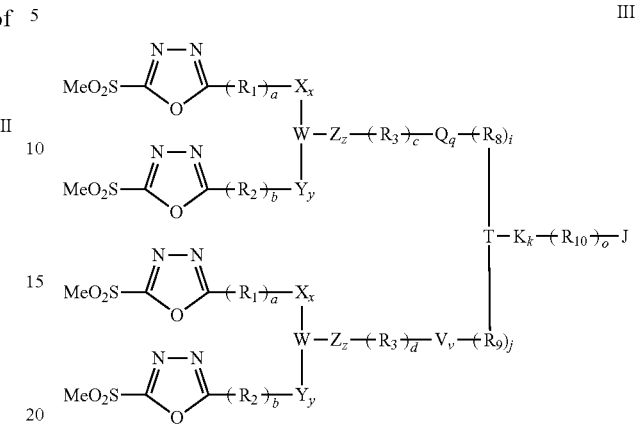

and pharmaceutically acceptable salt thereof,
wherein
T is selected from N, CR$_{11}$ and aryl;
X, Y, Z and K are each independently selected from O, C(=O), C(=O)NR$_{12}$, NR$_{13}$C(=O), NR$_{14}$C(=O)NR$_{15}$, NR$_{16}$C(=O)O and OC(=O)NR$_{17}$;
Q and V are each independently selected from O, C(=O), C(=O)NR$_{12}$, NR$_{13}$C(=O) and OC(=O);
a, b, c, d, i, j, k, v, o, q, x, y and z are each independently selected from 0 and 1;
R$_1$, R$_2$, R$_3$, R$_8$, R$_9$ and R$_{10}$ are each independently selected from C$_1$-C$_8$ alkylene and C$_1$-C$_8$ alkylene containing O in the backbone;
R$_{11}$, R$_{12}$, R$_{13}$, R$_{14}$, R$_{15}$, R$_{16}$ and R$_{17}$ are each independently selected from H and C$_1$-C$_8$ alkyl.

In a preferred embodiment, the invention provides a compound of formula III and pharmaceutical acceptable salt thereof, wherein
is selected from N and C$_6$-C$_{10}$ aryl, preferably phenyl.

In another preferred embodiment, the invention provides a compound of formula III and pharmaceutical acceptable salt thereof, wherein
R$_8$ and R$_9$ are each independently selected from C$_1$-C$_4$ alkylene and C$_1$-C$_4$ alkylene containing O in the backbone.

In another preferred embodiment, the invention provides a compound of formula III and pharmaceutical acceptable salt thereof, wherein
R$_{10}$ is selected from C$_1$-C$_8$ alkylene and C$_1$-C$_8$ alkylene containing O in the backbone.

In another preferred embodiment, the invention provides a compound of formula III and pharmaceutical acceptable salt thereof, wherein
Q and V are each independently selected from C(=O)NR$_{12}$, NR$_{13}$C(=O) and OC(=O).

In another preferred embodiment, the invention provides a compound of formula III and pharmaceutical acceptable salt thereof, wherein
K is selected from O, C(=O), C(=O)NR$_{12}$ and NR$_{13}$C(=O).

In another preferred embodiment, the invention provides a compound of formula III and pharmaceutical acceptable salt thereof, wherein
R$_3$ is selected from C$_1$-C$_4$ alkylene and C$_1$-C$_4$ alkylene containing O in the backbone;

In another preferred embodiment, the invention provides a compound of formula III and pharmaceutical acceptable salt thereof, wherein $R_1$ and $R_2$ are each independently selected from $C_1$-$C_4$ alkylene and $C_1$-$C_4$ alkylene containing O in the backbone;

In another preferred embodiment, the invention provides a compound of formula III and pharmaceutical acceptable salt thereof, wherein J is —COOH.

A typical compound of the invention includes but not limited to:

| Example No. | Structure and Name |
|---|---|
| 1 | 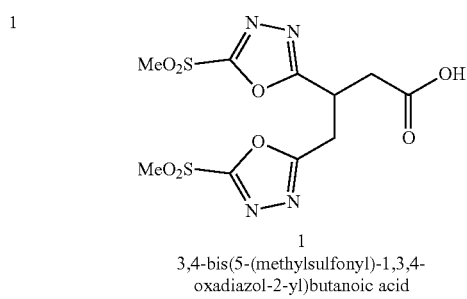<br>1<br>3,4-bis(5-(methylsulfonyl)-1,3,4-oxadiazol-2-yl)butanoic acid |
| 2 | 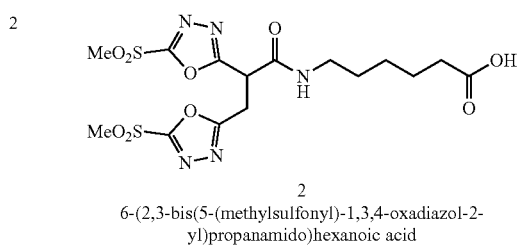<br>2<br>6-(2,3-bis(5-(methylsulfonyl)-1,3,4-oxadiazol-2-yl)propanamido)hexanoic acid |
| 3 | 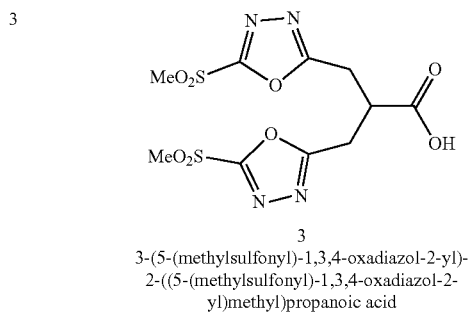<br>3<br>3-(5-(methylsulfonyl)-1,3,4-oxadiazol-2-yl)-2-((5-(methylsulfonyl)-1,3,4-oxadiazol-2-yl)methyl)propanoic acid |
| 4 | 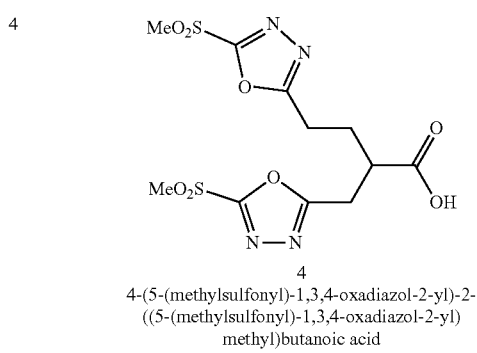<br>4<br>4-(5-(methylsulfonyl)-1,3,4-oxadiazol-2-yl)-2-((5-(methylsulfonyl)-1,3,4-oxadiazol-2-yl)methyl)butanoic acid |
| 5 | 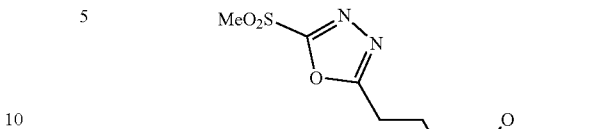<br>5<br>4-(5-(methylsulfonyl)-1,3,4-oxadiazol-2-yl)-2-(2-(5-(methylsulfonyl)-1,3,4-oxadiazol-2-yl)ethyl)butanoic acid |
| 6 | 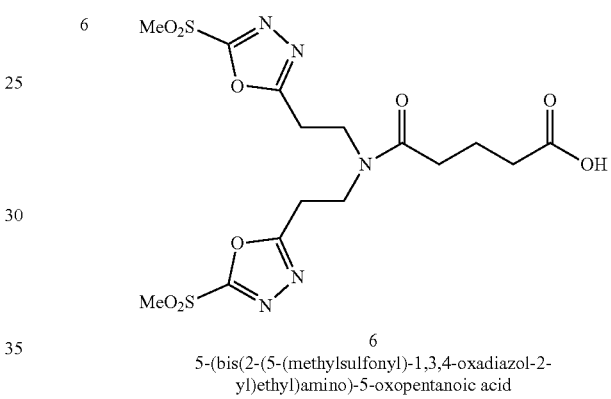<br>6<br>5-(bis(2-(5-(methylsulfonyl)-1,3,4-oxadiazol-2-yl)ethyl)amino)-5-oxopentanoic acid |
| 7 | 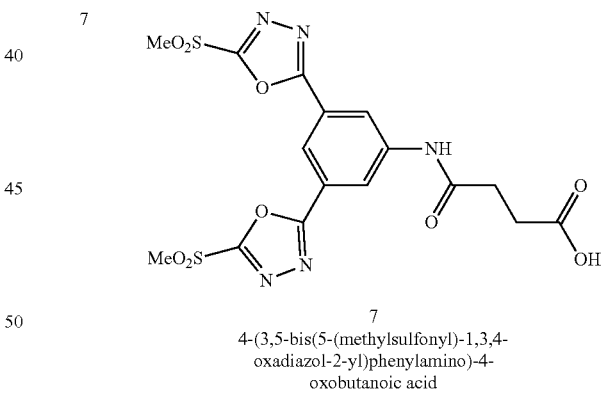<br>7<br>4-(3,5-bis(5-(methylsulfonyl)-1,3,4-oxadiazol-2-yl)phenylamino)-4-oxobutanoic acid |
| 8 | 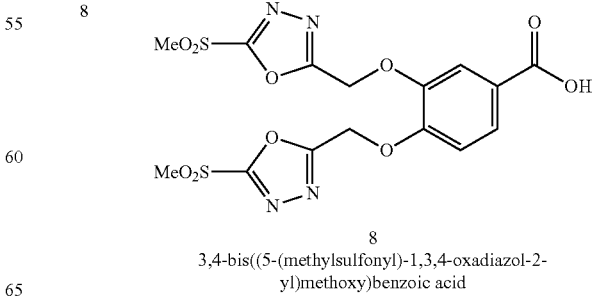<br>8<br>3,4-bis((5-(methylsulfonyl)-1,3,4-oxadiazol-2-yl)methoxy)benzoic acid |

| Example No. | Structure and Name |
|---|---|
| 9 | 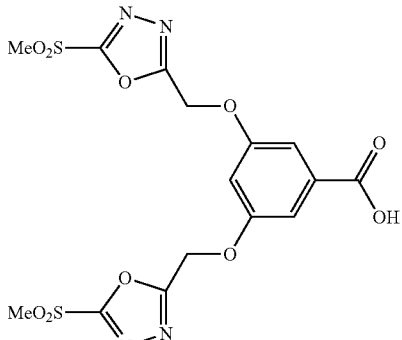<br>3,5-bis((5-(methylsulfonyl)-1,3,4-oxadiazol-2-yl)methoxy)benzoic acid |
| 10 | 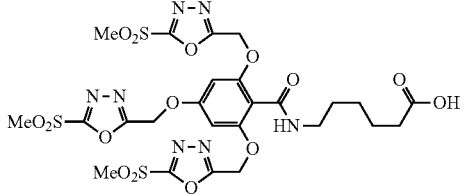<br>6-(2,4,6-tris((5-(methylsulfonyl)-1,3,4-oxadiazol-2-yl)methoxy)benzamido)hexanoic acid |
| 11 | 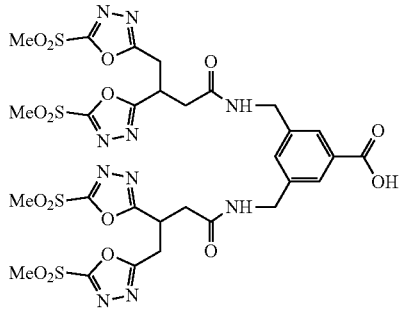<br>3,5-bis((3,4-bis(5-(methylsulfonyl)-1,3,4-oxadiazol-2-yl)butanamido)methyl)benzoic acid |
| 12 | 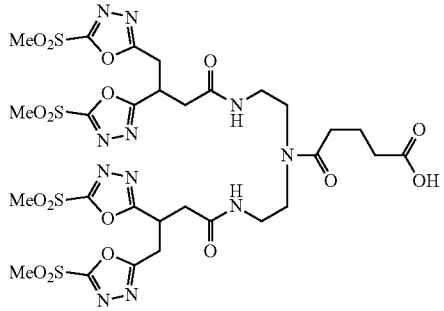<br>5-(bis(2-(3,4-bis(5-(methylsulfonyl)-1,3,4-oxadiazol-2-yl)butanamido)ethyl)amino)-5-oxopentanoic acid | or pharmaceutically acceptable salts thereof.

The invention further provides a compound of formula IV, $$B\text{-}A\text{-}D \qquad \qquad IV$$

wherein

B is a compound of formula I, II, or III, according to the present invention;

A is optionally other linker;

D is a drug molecule;

wherein B is linked to A or D by reaction between a terminal J group of B and a terminal group of A or D.

The invention further provides an antibody-drug conjugate of formula V, $$L\text{-}(B\text{-}A\text{-}D)_n \qquad \qquad V$$

wherein

L is an antibody, antibody fragment or protein;

B is a compound of formula I, II or III, according to the present invention;

A is optionally other linker;

D is a drug molecule;

n is an integer of 1 to 8;

wherein B is linked to A or D by reaction between a terminal J group of B and a terminal group of A or D, and is linked to L by reaction between the cysteines or other amino acid residues of L and 1,3,4-oxadiazole groups.

In a preferred embodiment, the invention provides a compound of formula IV or an antibody-drug conjugate of formula V, wherein A is optionally other linker than oxadiazole linker, including cleavable and noncleavable linkers.

In another preferred embodiment, the invention provides a compound of formula IV or an antibody-drug conjugate of formula V, wherein A has a formula of $C\text{-}E_e\text{-}F_f$ or $G_g$, wherein C is a cleavable linker;

E and F are self-immolative linkers;

e and f are each independently selected from an integer of 0 to 5;

G is a noncleavable linker;

g is an integer of 0 to 5.

In another preferred embodiment, the invention provides an antibody-drug conjugate of
formula V, according to the present invention, wherein it is the antibody-drug conjugate of formula VI, VII or VIII:

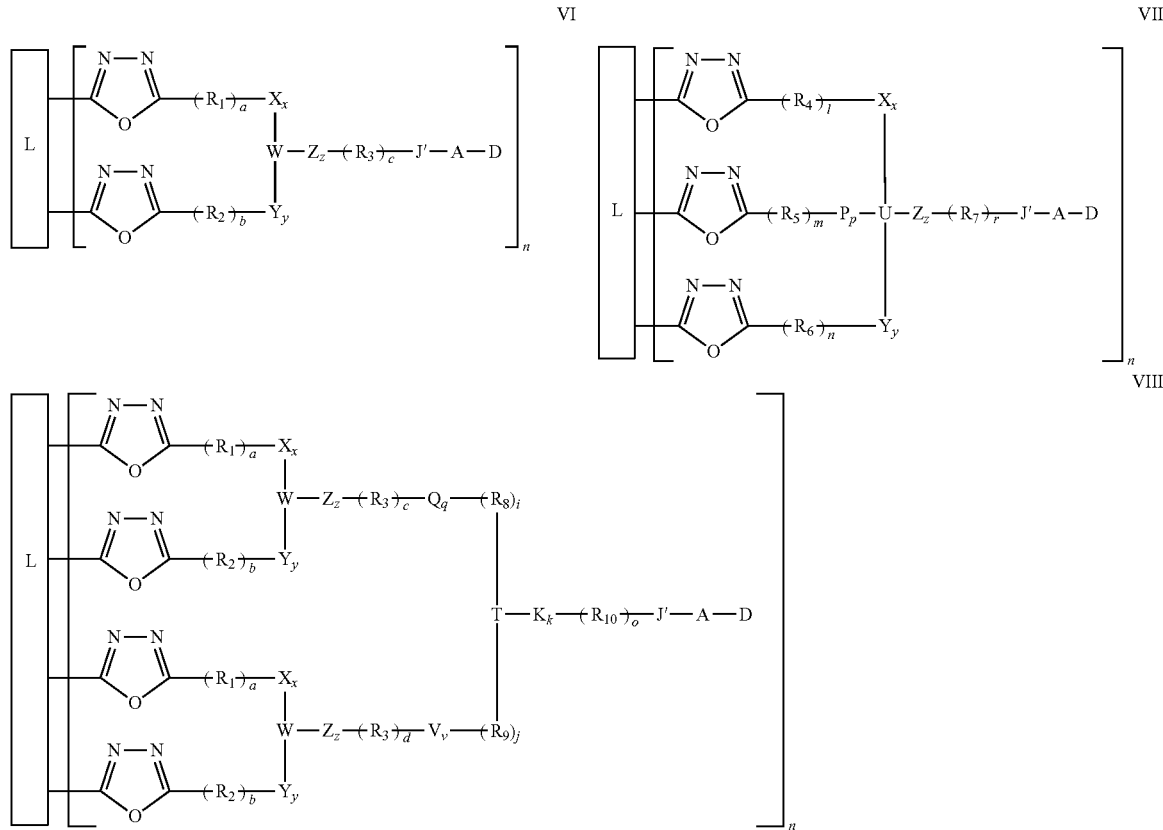

wherein

L is an antibody, antibody fragment or protein;

A is optionally other linker than 1,3,4-oxadiazole linker, including cleavable and noncleavable linker;

D is a drug molecule;

W is selected from N, $CR_{11}$ and aryl, preferably $C_6$-$C_{10}$ aryl, more preferably phenyl;

U is selected from C and aryl, preferably $C_6$-$C_{10}$ aryl, more preferably phenyl;

T is selected from N, $CR_{12}$ and aryl, preferably $C_6$-$C_{10}$ aryl, more preferably phenyl;

X, Y, P, Z and K are each independently selected from O, C(=O), C(=O)$NR_{12}$, $NR_{13}$C(=O), $NR_{14}$C(=O)$NR_{15}$, $NR_{16}$C(=O)O and OC(=O)$NR_{17}$;

Q and V are each independently selected from O, C(=O), C(=O)$NR_{12}$, $NR_{13}$C(=O) and OC(=O);

a, b, c, i, j, k, l, m, n, o, p, q, r, v, x, y and z are each independently selected from 0 and 1;

$R_1$, $R_2$, $R_3$, $R_4$, $R_5$, $R_6$, $R_7$, $R_8$, $R_9$ and $R_{10}$ are each independently selected from $C_1$-$C_8$ alkylene and $C_1$-$C_8$ alkylene containing O in the backbone, preferably $C_1$-$C_4$ alkylene and $C_1$-$C_4$ alkylene containing O in the backbone;

$R_{11}$, $R_{12}$, $R_{13}$, $R_{14}$, $R_{15}$, $R_{16}$ and $R_{17}$ are each independently selected from H and $C_1$-$C_8$ alkyl, preferably $C_1$-$C_4$ alkyl.

In another preferred embodiment, the invention provides an antibody-drug conjugate of
formula V according to the present invention, wherein the antibody targets cell surface receptors or tumor-related antigens.

In another preferred embodiment, the invention provides an antibody-drug conjugate of
formula V according to the present invention, wherein the antibody is IgG1.

In another preferred embodiment, the invention provides an antibody-drug conjugate of
formula V according to the present invention, wherein the drug is cytotoxic drug, anti-autoimmune disease drug, or anti-inflammation drug.

The invention further provides a pharmaceutical composition comprising an antibody-drug conjugate of formula V according to the present invention and pharmaceutically acceptable carriers.

The invention further provides a compound of formula I, II and III according to the present invention, for use as a linker in the preparation of antibody-drug conjugates.

The invention further provides the use of an antibody-drug conjugate of formula V according to the present invention, or the pharmaceutical composition comprising the same, in the preparation of drugs for the treatment of cancers, auto-immune diseases and inflammation diseases.

The invention further provides the use of the compound of the formula I, II, and III according to the present invention as linkers in the preparation of antibody-drug conjugates.

The invention further provides an antibody-drug conjugates of formula V according to the present invention, or the pharmaceutical composition comprising the said ADC, for use as a drug which is prepared for the treatment of cancers, auto-immune diseases or inflammation diseases.

The invention further provides a method for the treatment of cancers, auto-immune diseases or inflammation diseases, comprising administrating to the subject in need of it a therapeutically effective amount of the antibody-drug conjugates of formula V according to the present invention, or the pharmaceutical composition comprising the same.

DETAILED DESCRIPTION OF THE INVENTION

The invention disclosed a series of novel bis(1,3,4-oxadiazole), tri(1,3,4-oxadiazole) and tetra(1,3,4-oxadiazole) linkers.

The bis(1,3,4-oxadiazole) linker according to the present invention contains two 2-methylsulfonyl-1,3,4-oxadiazole groups, which can be used to crosslink the antibody interchain cysteine or other amino acid residues, leading to a conjugated product containing a main component with a DAR value of 4.

The tri(1,3,4-oxadiazole) linker according to the present invention contains three 2-methylsulfonyl-1,3,4-oxadiazole groups, which can be used to crosslink the antibody interchain cysteine or other amino acid residues, leading to a conjugated product containing a main component with a DAR value of 3.

The tetra(1,3,4-oxadiazole) linker according to the present invention contains four 2-methylsulfonyl-1,3,4-oxadiazole groups, which can be used to crosslink the antibody interchain cysteine or other amino acid residues, leading to a conjugated product containing a main component with a DAR value of 2.

The oxadiazole linkers according to the present invention can be used to prepare antibody-drug conjugates without the need of antibody recombinant modification, and thus are universal linkers that are applicable to most antibodies, such as IgG1. Also, the conjugation procedure is simple and controllable, endowing them with a broad application prospect.

Specifically, the bis(1,3,4-oxadiazole) linker according to the present invention contains two 2-methylsulfonyl-1,3,4-oxadiazole groups and a third coupling group. The two 2-methylsulfonyl-1,3,4-oxadiazole groups are used to crosslink the interchain cysteine (after reduction) or other amino acid residues, while the third coupling group is used to link small-molecule drug or drug-linker unit, as shown by scheme 1.

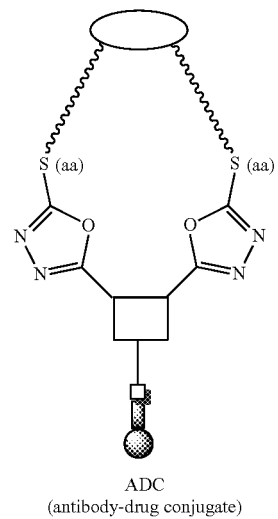

ADC
(antibody-drug conjugate)

The tri(1,3,4-oxadiazole) linker according to the present invention contains three 2-methylsulfonyl-1,3,4-oxadiazole groups and a fourth coupling group. The three 2-methylsulfonyl-1,3,4-oxadiazole groups are used to crosslink the interchain cysteine (after reduction) or other amino acid residues, while the fourth coupling group is used to link small-molecule drug or drug-linker unit, as shown by scheme 2.

Scheme 1

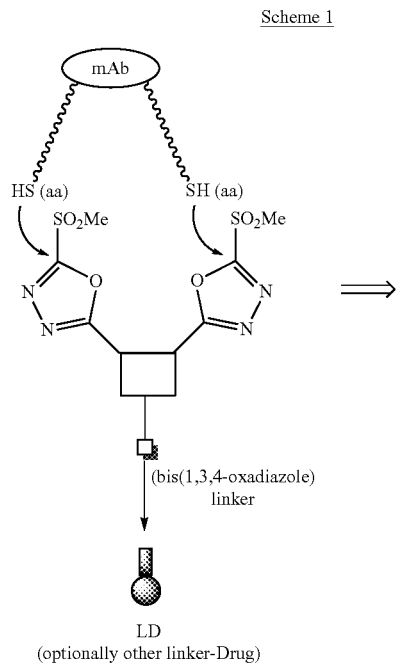

(bis(1,3,4-oxadiazole) linker)

LD
(optionally other linker-Drug)

Scheme 2

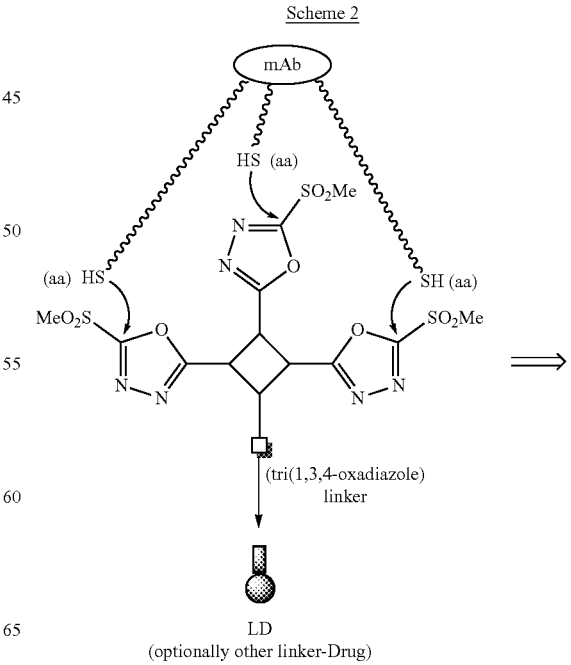

(tri(1,3,4-oxadiazole) linker)

LD
(optionally other linker-Drug)

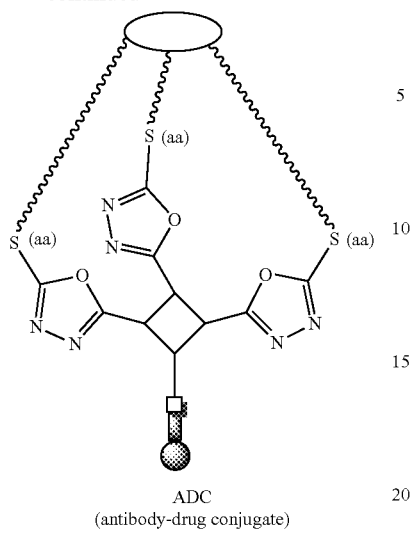

ADC
(antibody-drug conjugate)

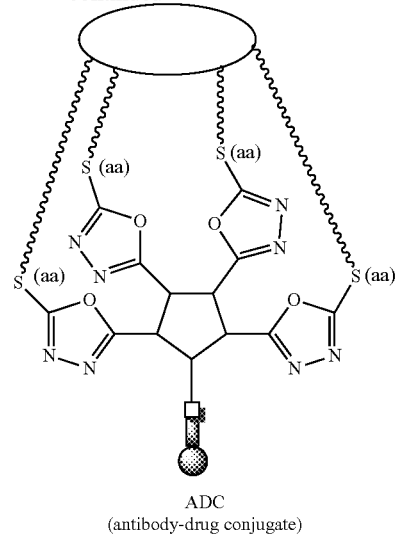

ADC
(antibody-drug conjugate)

The tetra(1,3,4-oxadiazole) linker according to the present invention contains four 2-methylsulfonyl-1,3,4-oxadiazole groups and a fifth coupling group. The four 2-methylsulfonyl-1,3,4-oxadiazole groups are used to crosslink the interchain cysteine (after reduction) or other amino acid residues, while the fifth coupling group is used to link small-molecule drug or drug-linker unit, as shown by scheme 3.

Scheme 3

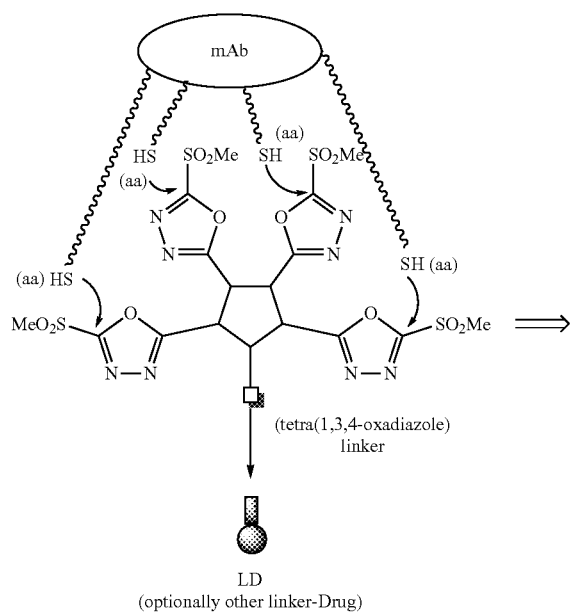

(tetra(1,3,4-oxadiazole) linker

LD
(optionally other linker-Drug)

The ADCs thus obtained can be used to selectively deliver cytotoxic drugs to target cells, for example, tumor cells. The antibody-drug conjugate will bind specifically to the cell surface proteins, and the binding complex will be internalized rapidly by the cells. Once internalized, the cytotoxic drug will be released in certain active form and take effects.

As used herein, the antibody includes chimeric, humanized, or human antibody; or antibody fragment that can bind to antigen; or Fc fused protein; or protein.

As used herein, the drug is high-potency cytotoxic drug, including but not limited to, maytansinoids, auristatins, calicheamicins, doxorubicins, CC-1065 and duocarmycins derivatives, PBD dimers, and tubulysins, etc. Under certain conditions, the drug could be poly(ethylene glycol).

The drug itself or drug-linker unit can be conjugated to the antibody via oxadiazole linkers, producing interchain cross-linked conjugates. Compared to traditional ones, the antibody-drug conjugate provided according to the present invention has a main component of DAR~4 (for bis(1,3,4-oxadiazole) linker), DAR~3 (for tris(1,3,4-oxadiazole) linker) and DAR~2 (for tetra(1,3,4-oxadiazole) linker), respectively. Furthermore, these ADC products have much narrower DAR distribution, which greatly improves both structural and pharmacological homogeneities.

Antibody

As used herein, the term "antibody" or "antibody unit" includes within its scope any fragments of an antibody that binds to or reactively associates or complexes with a receptor, antigen or other receptor unit associated with a given target-cell population. An antibody can be any protein or protein-like molecule that binds to, complexes with, or reacts with a moiety of a cell population to be therapeutically or otherwise biologically modified.

Antibody that makes up the ADCs of the invention preferably retains the antigen binding capability of their native, wild type counterparts. Thus, antibodies of the invention are capable of binding, preferably specifically, to antigens. Such antigens include, for example, tumor-associated antigens (TAA), cell surface receptor proteins and other cell surface molecules, cell survival regulatory factors, cell proliferation regulatory factors, molecules associated with tissue development or differentiation (e.g., known or suspected to contribute function), lymphokines, cytokines, molecules involved in cell cycle regulation, molecules involved in vasculogenesis and molecules associated with angiogenesis (for e.g. known or suspected to contribute function). The tumor-associated antigen may be a cluster differentiation factor (i.e., a CD protein). Antigens that bind to the antibodies of the present invention may be one or a subset of the above categories, wherein the other subset(s) of said category comprise other molecules/antigens that have a distinct characteristic (with respect to the antigen of interest).

Antibodies used in ADCs include, but not limited to, antibodies against cell surface receptors and tumor-associated antigens (TAA). Such tumor-associated antigens are well known in the art, and can be prepared according to the methods or information which is well known in the art for the preparation of antibodies. In order to develop effective cellular targets that can be used in the diagnosis and treatment for cancer, the researchers sought to find transmembrane or otherwise tumor-associated polypeptides that are specifically expressed on the surface of one or more particular type(s) of cancer cell as compared to the other one or more normal non-cancerous cell(s). Often, such tumor-associated polypeptides are more abundantly expressed on the surface of the cancer cells as compared to the non-cancerous cells. The identification of such tumor-associated factors can greatly enhance the specific targeting properties of antibodies based cancer therapy.

Examples of TAA include, but are not limited to, Tumor-Associated Antigens (1)-(36) listed below. For convenience, information relating to these antigens, all of which are known in the art, is listed below and includes names, alternative names, Genbank accession numbers. Nucleic acid and protein sequences corresponding to TAA (1)-(36) are available in public databases such as GenBank. Tumor-associated antigens targeted by antibodies include all amino acid sequence variants and isoforms possessing at least about 70%, 80%, 85%, 90%, or 95% sequence identity relative to the sequences identified in the cited references, or exhibit substantially the same biological properties or characteristics as a TAA having a sequence found in the cited references.

Tumor-Associated Antigens (1)-(36):
(1) BMPR1B (bone morphogenetic protein receptor-type IB, Genbank accession no. NM_001203);
(2) E16 (LAT1, SLC7A5, Genbank accession no. NM_003486);
(3) STEAP1 (six transmembrane epithelial antigen of prostate, Genbank accession no. NM_012449);
(4) 0772P (CA125, MUC16, Genbank accession no. AF361486);
(5) MPF (MPF, MSLN, SMR, megakaryocyte potentiating factor, mesothelin, Genbank accession no. NM_005823);
(6) Napi3b (NAPI-3B, NPTIIb, SLC34A2, solute carrier family 34 (sodium phosphate) member 2, type II sodium-dependent phosphate transporter 3b, Genbank accession no. NM_006424);
(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B, Genbank accession no. AB040878);
(8) PSCA hlg (2700050C12Rik, C530008016Rik, RIKEN cDNA 2700050C12, RIKEN cDNA 2700050C12 gene, Genbank accession no. AY358628);
(9) ETBR (Endothelin type B receptor, Genbank accession no. AY275463);
(10) MSG783 (RNF124, hypothetical protein FLJ20315, Genbank accession no. NM_017763);
(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank accession no. AF455138);
(12) TrpM4 (BR22450, FLJ20041, TRPM4, TRPM4B, transient receptor potential cation channel, subfamily M, member 4, Genbank accession no. NM_017636);
(13) CRIPTO (CR, CR1, CRGF, CRIPTO, TDGF1, teratocarcinoma-derived growth factor, Genbank accession no. NP_003203 or NM_003212;
(14) CD21 (CR2 (Complement receptor 2) or C3DR (C3d/Epstein Barr virus receptor) or Hs. 73792, Genbank accession no. M26004);
(15) CD79b (CD79B, CD79p, IGb (immunoglobulin associated beta), B29, Genbank accession no. NM_000626);
(16) FcRH2 (IFGP4, IRTA4, SPAP1A (SH2 domain containing phosphatase anchor protein 1a), SPAP1B, SPAP1C, Genbank accession no. NM_030764);
(17) HER2 (ErbB2, Genbank accession no. M11730);
(18) NCA (CEACAM6, Genbank accession no. M18728);
(19) MDP (DPEP1, Genbank accession no. BC017023);
(20) IL20Rα (IL20Ra, ZCYTOR7, Genbank accession no. AF184971);
(21) Brevican (BCAN, BEHAB, Genbank accession no. AF229053);
(22) EphB2R (DRT, ERK, Hek5, EPHT3, Tyro5, Genbank accession no. NM_004442);
(23) ASLG659 (B7h, Genbank accession no. AX092328);
(24) PSCA (Prostate stem cell antigen precursor, Genbank accession no. AJ297436);
(25) GEDA (Genbank accession no. AY260763);
(26) BAFF-R (B-cell activating factor receptor, BLys receptor 3, BR3, Genbank accession no. AF116456);
(27) CD22 (B-cell receptor CD22-β form, Genbank accession no. AK026467);
(28) CD79a (CD79A, CD79α, immunoglobulin-associated alpha, a B-cell specific protein that covalently interacts with Ig beta (CD79B) and forms a complex on the surface with Ig M molecules, transduces a signal involved in B-cell differentiation, Genbank accession No. NP-001774.1);
(29) CXCR5 (Burkitt's lymphoma receptor 1, a G protein-coupled receptor that is activated by the CXCL13 chemokine, plays a role in lymphocyte migration and humoral defense, plays a role in HIV-2 infection and perhaps development of AIDS, lymphoma, myeloma, and leukemia, Genbank accession No. NP_001707.1);
(30) HLA-DOB (Beta subunit of MHC class II molecule (Ia antigen) that binds peptides and presents them to CD4+T lymphocytes, Genbank accession No. NP_002111.1);
(31) P2X5 (Purinergic receptor P2X ligand-gated ion channel 5, an ion channel gated by extracellular ATP, may be involved in synaptic transmission and neurogenesis, its deficiency may contribute to the pathophysiology of idiopathic detrusor instability, Genbank accession No. NP_002552.2);
(32) CD72 (B-cell differentiation antigen CD72, Lyb-2, Genbank accession No. NP_001773.1);
(33) LY64 (lymphocyte antigen 64 (RP105), type I membrane protein family which is rich in leucine repeat (LRR), regulates B-cell activation and apoptosis, loss of function is associated with increased disease activity in patients with systemic lupus erythematosis, Genbank accession No. NP_005573.1);
(34) FcRH1 (Fc receptor-like protein 1, a putative receptor for the immunoglobulin Fc domain that contains C2 type Ig-like and ITAM domains, may play a role in B-lymphocyte differentiation, Genbank accession No. NP_443170.1);
(35) IRTA2 (Translocation-related immunoglobulin superfamily receptor 2, a putative immunoreceptor with possible roles in B cell development and lymphoma genesis; gene disorder caused by translocation occurs in certain B-cell malignancies, Genbank accession No. NP_112571.1);
(36) TENB2 (putative transmembrane proteoglycan, related to the EGF/heregulin family of growth factors and follistatin, Genbank accession No. AF179274).

Drug

As used herein, the term "drug" or "D" refers to any compound possessing a desired biological activity and having a reactive functional group that may be used to incorporate the drug into the conjugate of the invention. The desired biological activity includes diagnosis, cure, alleviation, treatment, or prevention of disease in human or other animals. Thus, so long as it has the necessary reactive functional group, the term "drug" refers to the drugs recognized by the official United States Pharmacopeia, official Homeopathic Pharmacopeia of the United States, official National Formulary, or any supplement thereof. Exemplary drugs are set forth in the Physician's Desk Reference (PDR) and in the Orange Book maintained by the U.S. Food and Drug Administration (FDA). New drugs are continually being discovered and developed, and the present invention provides that these new drugs may also be incorporated into the prodrugs of the present invention.

Preferably, the drug is a cytotoxic drug useful in cancer therapy; a protein or polypeptide possessing a desired biological activity, such as a toxin, e.g., abrin, ricin A, pseudomonas exotoxin, and diphtheria toxin; other suitable proteins including tumor necrosis factor, α-interferon, β-interferon, nerve growth factor, platelet derived growth factor, tissue plasminogen activator, and biological response modifiers, such as lymphokines, interleukin-1 (IL-1), interleukin-2 (IL-2), interleukin-6 (IL-6), granulocyte macrophage colony stimulating factor (GM-CSF), granulocyte colony stimulating factor (G-CSF), or other growth factors.

In one aspect, the drugs are maytansine or maytansinoids. Maytansine inhibits cell proliferation by inhibiting the formation of microtubules of the microtubulin protein (Science 1975, 189, 1002-1005; U.S. Pat. No. 5,208,020). Maytansinoids are derivatives of maytansine. Both maytansine and maytansinoids are highly cytotoxic, but their clinical use in cancer therapy has been greatly limited due to poor selectivity for tumors. However, the high cytotoxic potency enables them to be attractive drug moieties in ADCs. The structures shown below are maytansine, maytansinoids, and three representative maytansinoids commonly used in ADC:

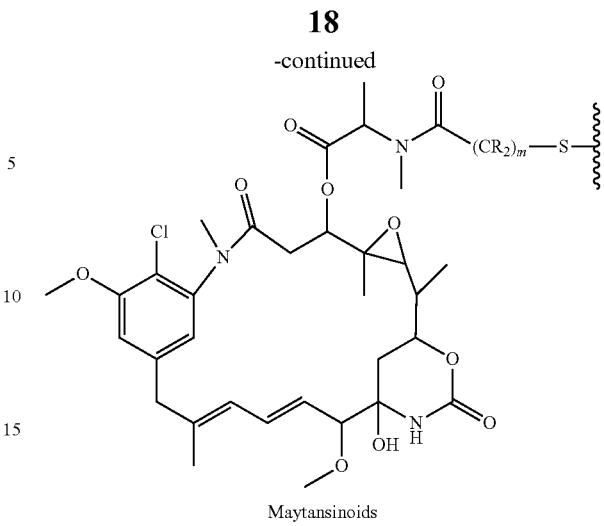

Maytansinoids

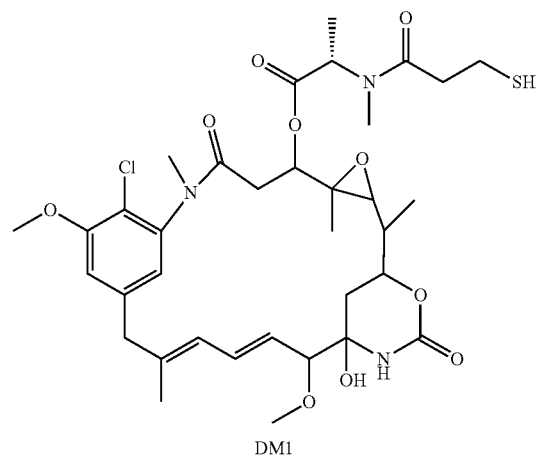

DM1

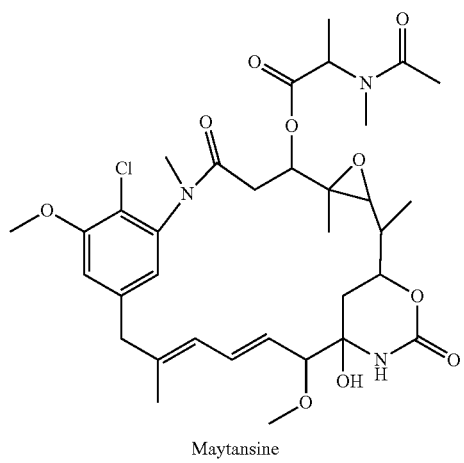

Maytansine

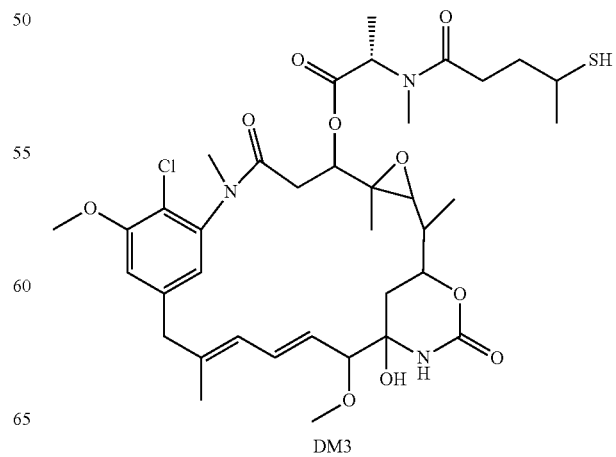

DM3

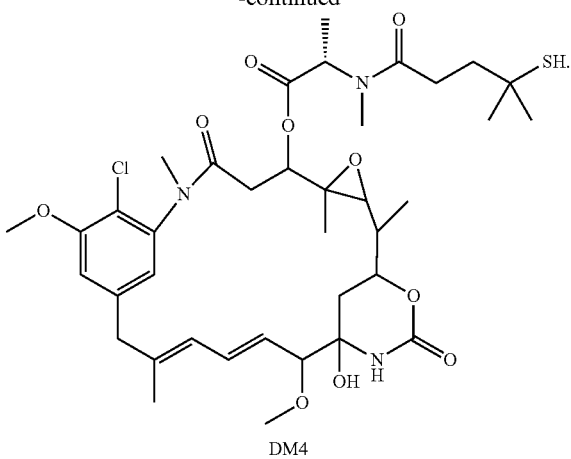

DM4

The main raw material for preparing maytansinoids is maytansinol, which is mainly obtained from ansamitocins hydrolysis. Ansamitocins could be accessibly produced by fermentation. Ansamitocin derivatives (WO 2012/061590) and alaninyl maytansinol (US 2012/0121615) are also reported to be good candidates as ADC "warheads".

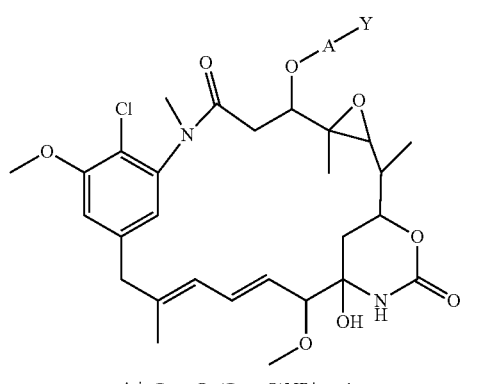

A is C=O, (C=O)NR', and (C=O)O
Y is a substituent group
Ansamitocin derivatives

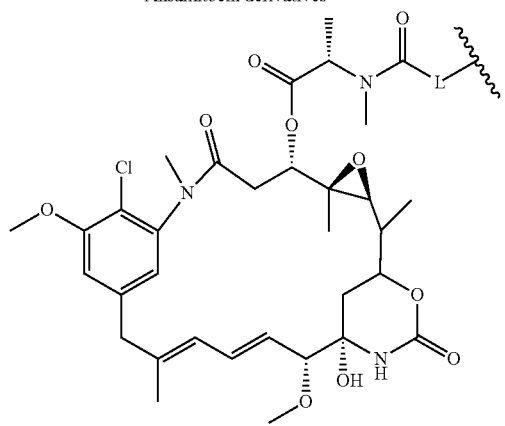

Alaninyl maytansinol

In another aspect, the drugs are auristatins. Auristatins are synthetic analogues of Dolastatin 10, which was biologically active polypeptide isolated from the marine mollusk *Dolabella auricularia* (U.S. Pat. No. 7,498,298). Dolastatin 10 is an agent that inhibits tubulin polymerization by binding to the same domain on tubulin as the anticancer drug vincristine. Dolastitin 10, auristatin PE, and auristatin E are all linear peptides having four amino acids, three of which are unique to the dolastatins, and a C-terminal amide. Two representative auristatins, monomethyl auristatin E (MMAE) and monomethyl auristatin F (MMAF), are preferred drug moiety candidates for ADCs.

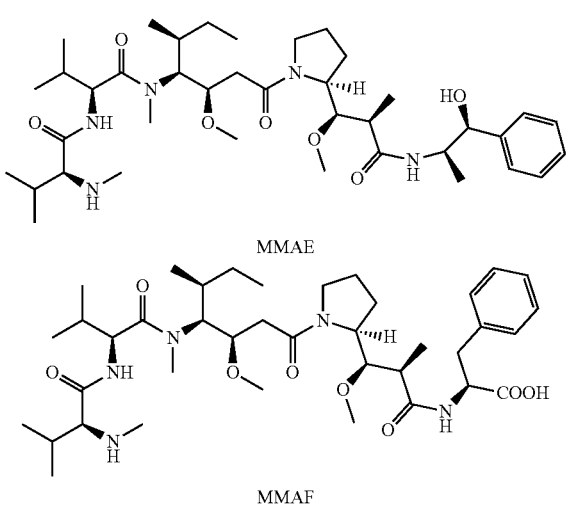

MMAE

MMAF

In another aspect, the drugs are tubulysins. Tubulysins are natural products first isolated from myxobacterial culture, which are potent cell growth inhibitor that act by inhibiting tubulin polymerization, and among which Tubulysin D is the most potent. Tubulysin D is a complex tetrapeptide, and unstable in both acidic or basic conditions due to the o-acyl/N,O-acetal functional groups. US 2011/0021568 and US 2013/0224228 disclosed a series of tubulysin analogs respectively, which remove the unstable groups from the structure and have high cytotoxic potency.

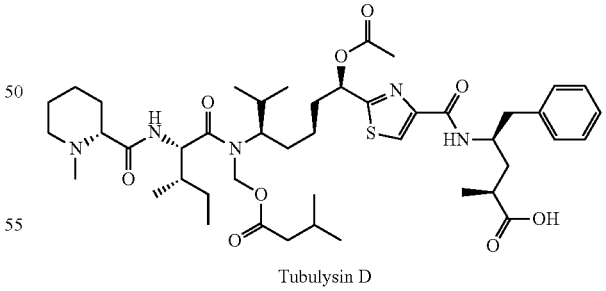

Tubulysin D

In another aspect, the drugs are calicheamicins. Calicheamicins are antitumor antibiotics that bind to the minor groove of DNA to promote double-stranded DNA cleavage at a specific site, thus causing cell death. Calicheamicins are potent at sub-picomolar concentrations in vitro, but their low therapeutic index precluded further clinical development. The high potency, however, makes them good candidates for ADCs (such as Gemtuzumab Ozogamicin and Inotuzumab Ozogamicin).

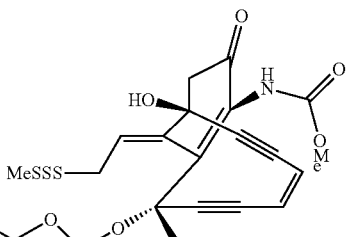
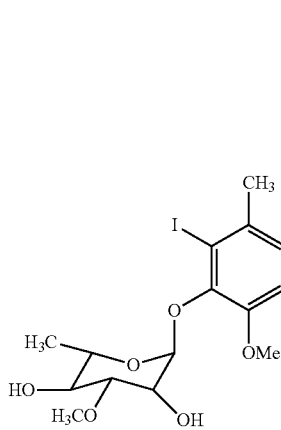

Calicheamicin

In another aspect, the drugs are doxorubicins. Doxorubicin is an intercalating agent that embeds DNA double helix structure to block DNA replication and is used as chemotherapeutic agent. Due to the relative low potency of doxorubicin ($IC_{50}$ of 0.1-0.2 µM for human carcinoma lines, whereas subnanomolar activities are now typically seen for ADC payloads), application of doxorubicin as ADC drug moiety is not popular.

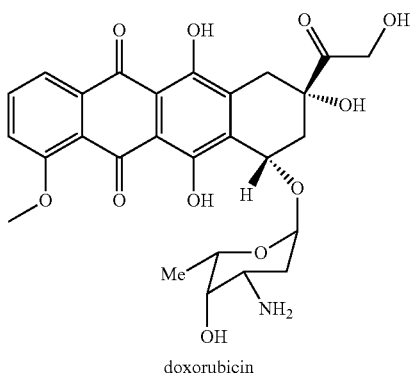 [SMILES: COc1cccc2c1C(=O)c1c(O)c3c(c(O)c1C2=O)C[C@@](O)(C(=O)CO)C[C@@H]3OC1CC(N)C(O)C(C)O1]

doxorubicin

In another aspect, the drugs are duocarmycins, CC-1065 and other cyclopropapyrroloind-4-one (CPI) derivatives, which are potent minor-groove binding DNA alkylating agents. Cyclopropabenzindol-4-one analogues (CBI) are chemically more stable, biologically more potent, and synthetically more accessible than their parent compounds comprising the nature CPI alkylating subunit. One representative CBI derivative is the phenolic hydroxyl group-protected CBI (see the formula below), which has decreased prodrug toxicity and improved water solubility.

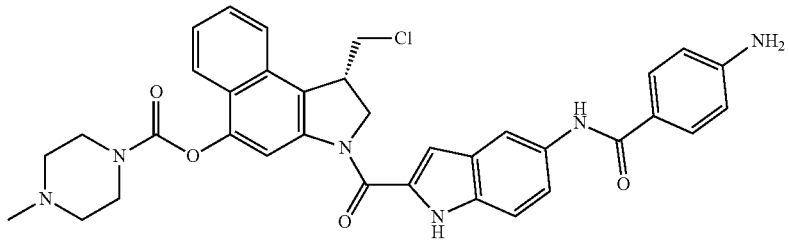 [SMILES: CN1CCN(C(=O)Oc2cc3c(c4ccccc24)[C@H](CCl)CN3C(=O)c2cc3cc(NC(=O)c4ccc(N)cc4)ccc3[nH]2)CC1]

In another aspect, the drugs are pyrrolo[2,1-c][1,4]benzodiazepines (PBDs) or PBD dimers. The pyrrolo[2,1-c][1,4]benzodiazepines (PBDs) are natural products produced by *Streptomyces* species with the unique characteristic of forming nondistortive covalent adducts in the minor groove of DNA, specifically at the purine-guanine-purine sequences. There is a growing interest in using PBDs as part of a small-molecule strategy for targeting DNA sequences and also as novel anticancer and antibacterial agents (Biochemistry 2008, 47, 11818-11829). The biological activity of these molecules can be potentiated by joining two PBD units together through their C8/C8-hydroxyl groups via a flexible alkylene linker (WO 2011/130616). The PBD dimers are thought to form sequence-selective DNA lesions such as the palindromic 5'-Pu-GATC-Py-3' interstrand cross-link, which mainly accounts for their biological activity. These compounds have been shown to be highly useful cytotoxic agents and good candidates as ADC warheads.

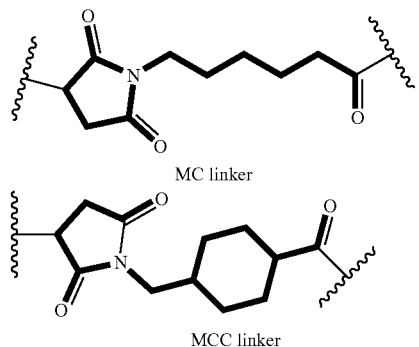

MC linker

MCC linker

Cleavable linkers, as the name implies, could be cleaved within the target cells to release the active drugs (small molecule drugs themselves). Cleavable linkers can be categorized into two main groups: chemically labile and enzyme-labile linkers.

Chemically labile linkers could be selectively cleaved according to the properties of the plasma and cytoplasm. Such properties include pH value, glutathione concentration, etc.

For pH sensitive linkers, generally called acid-cleavable linker, the linkers are relatively stable in the neutral environment (pH 7.3-7.5) of blood, but will undergo hydrolysis in the mildly acidic endosomes (pH 5.0-6.5) and lysosomes (pH 4.5-5.0). Most of the linkers, such as hydrozones, carbonates, acetals, ketals, were used for the first generation of ADCs. However, due to the limited plasma stability of the acid-cleavable linkers, the ADCs based on this kind of linkers have relatively short half-life (2-3 days). The shortened half-lives preclude the application of pH-sensitive linkers in the new generations of ADCs to a certain degree.

For glutathione-sensitive linkers, generally called disulfide linkers, the release is attributed to the high intracellular concentration in the cytoplasma (millimolar range) versus the relatively low concentration in the blood (micromolar range) of glutathione. This is especially true for tumor cells, where the hypoxic state results in enhanced activity of reductive enzymes and thus even higher glutathione concentrations. Disulfide bonds are thermodynamically stable and thus provide good stability in plasma.

Enzyme-labile linkers, such as peptide linkers, are alternative approaches to achieve better control of the drug

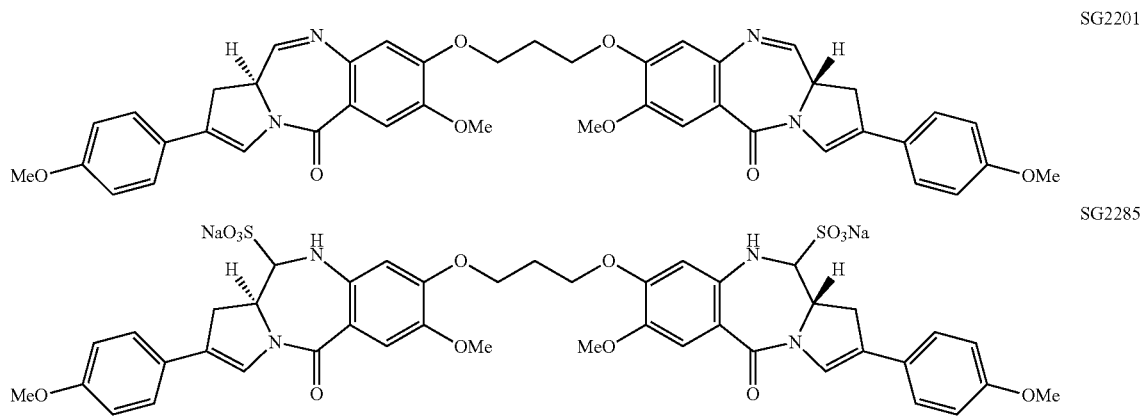

SG2201

SG2285

In another aspect, the drugs are not limited to abovementioned categories and also include all drugs that could be used in ADCs.

Linker

As used herein, the term "linker" or "ADC linker" refers to a bifunctional or multifunctional molecule that can react with a protein/antibody and a drug respectively, and thus link the protein/antibody to the drug as a "bridge". According to drug release mechanism in cells, "linker" or "ADC linker" could be classified into two categories: noncleavable linker and cleavable linker.

Noncleavable linker is a kind of relatively stable linker, which is difficult to be cleaved under in vivo conditions. For ADCs with noncleavable linkers, the release mechanism is believed to occur via internalization of the ADC followed by degradation of the mAb component in the lysosome, resulting in the release of the small molecular drug still attached via the linker to an antibody amino acid residue. The chemical modification of the drug didn't diminish its cytotoxic potential. This form of the drug is, however, charged (amino acid residue) and presumably hard to diffuse into neighboring cells. Hence, it can't kill adjacent tumor cells (bystander effects) that don't express the target antigen (antigen-negative cells) (Bioconjugate Chem. 2010, 21, 5-13). Some common linkers, such as MC linker, MCC linker, etc., are shown as below:

release. The peptide linkage will be effectively cleaved by lysosomal proteases, such as cathepsin B or plasmin (elevated levels in certain tumor tissues). Such peptidic linkages are deemed stable in plasma circulation, as proteases are usually not extracellularly active due to the extracellular unfavorable pH and the serum protease inhibitors. In view of the high plasma stability and good intracellular cleaving selectivity and efficiency, enzyme-labile linkers are broadly selected as cleavable linker candidates in ADCs. Typical enzyme-labile linkers include Val-Cit (vc), etc.

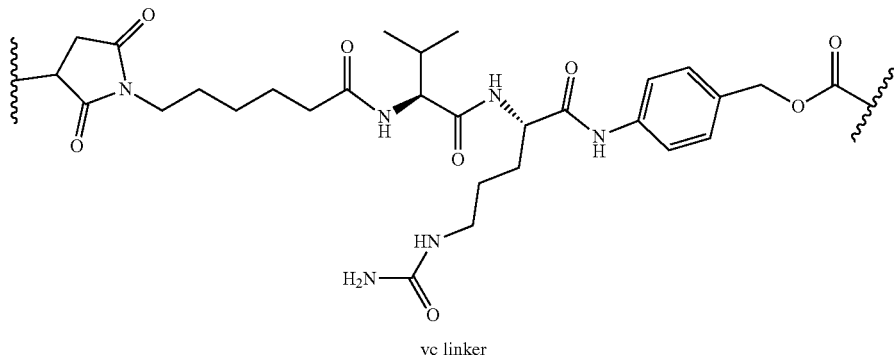 [SMILES: *C(=O)OCc1ccc(NC(=O)[C@H](CCCNC(N)=O)NC(=O)[C@@H](NC(=O)CCCCCN2C(=O)CC(*)C2=O)C(C)C)cc1]

vc linker

Self-immolative linker is generally sited between cleavable linker and cytotoxic drug, or is part of a cleavable linker itself. The working mechanism of self-immolative linker is that it can undergo self-structural rearrangement to release the linked active drug when the cleavable linker was cut by protease. Typical self-immolative linkers include p-aminobenzyl alcohol (PAB), etc.

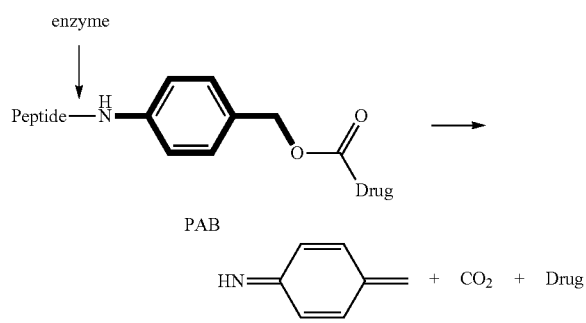

Antibody-drug Conjugate

The antibody-drug conjugate according to the present invention is composed of antibody, oxadiazole linker, optional other linker, and drug. The optional other linker is referred to cleavable linker or non-cleavable linker.

Antibodies are comprised of globular proteins, which have an array of amino acids linkage sites that can be used to conjugate drug-linker unit. Due to their tertiary and quaternary structure, only solvent-accessible amino acid residues can be conjugated. In practice, high-yielding conjugations usually occur on the ε-amino group of lysine residues or the sulfhydryl group of cysteine residues.

The abundance of lysine side-chains at the antibody surface provide multiple linkage sites for conjugation, which leads to a mixture of ADCs with different payload numbers (DARs) and conjugation sites.

Compared to the ones traditionally made, the ADCs prepared based on bis(1,3,4-oxadiazole) linker according to the present invention not only have the average DAR around 4, residing in the optimized ADC DAR range of 2-4, but also have much narrower DAR distribution, with the DAR4 fraction being the main component (more than 85%).

Compared to the ones traditionally made, the ADCs prepared based on tri(1,3,4-oxadiazole) linker according to the present invention not only have the average DAR around 3, residing in the optimized ADC DAR range of 2-4, but also have much narrower DAR distribution, with the DAR3 fraction being the main component (more than 85%).

Compared to the ones traditionally made, the ADCs prepared based on tetra(1,3,4-oxadiazole) linker according to the present invention not only have the average DAR around 2, residing in the optimized ADC DAR range of 2-4, but also have much narrower DAR distribution, with the DAR2 fraction being the main component (more than 85%).

In addition, the conjugation products based on the above oxadiazole linkers don't contain naked antibody (DAR=0), which has no cell killing effect. Also, the conjugation products don't contain heavily conjugated antibody (for example DAR>6), which is cleared more rapidly than those with low DAR numbers. As a result, the ADC products provided according to the present invention show much improved homogeneity.

Definition

The term "Drug/Antibody Ratio (DAR)" as used herein refers to the number of drugs that are conjugated to each antibody molecule. Because antibody-drug conjugate samples contain multiple components with different DAR values, the concepts of "average DAR value" and "DAR value distribution" are more suitable for describing the composition of antibody drug conjugates. The average DAR value is the ratio of the total number of drug molecules in a sample to the total number of antibodies, and the DAR value distribution refers to the content distribution of the components with various DAR value in the sample.

"Alkyl" refers to a saturated straight or branched aliphatic hydrocarbon group including 1-20 carbon atoms. Preferably, an alkyl group is an alkyl having 1 to 12 carbon atoms, more preferably 1 to 10 carbon atoms, and most preferably an alkyl having 1 to 6 carbon atoms. Representative examples include, but are not limited to, methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and isomers of branched chains thereof. More preferably, an alkyl group is a lower alkyl having 1 to 6 carbon atoms. Representative examples include, but are not limited to, methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, etc. The alkyl group can be substituted or unsubstituted. When substituted, the substituent group(s) can be substituted at any available connection point, and preferably the substituent group(s) is one or more groups independently selected from the group consisting of alkyl, alkenyl, alkynyl, alkyloxyl, alkylthio, alkylamino, halogen, thiol, hydroxy, nitro, cyano, cycloalkyl, heterocyclyl, aryl, heteroaryl, cycloalkoxy, heterocyclic alkoxy, cycloalkylthio, heterocyclic alkylthio, oxo group, carboxyl or carboxylate group.

"Alkylene" means an alkyl group as defined above wherein one of the hydrogen atoms is further removed to form a divalent group. Representative examples include, but are not limited to, methylene (—CH$_2$—), ethylene (—(CH$_2$)$_2$—), propylene ((CH$_2$)$_3$—), butylene (—(CH$_2$)$_4$—), and the like.

"Alkenyl" refers to an alkyl group as defined above consisting of at least two carbon atoms and at least one carbon-carbon double bond, for example vinyl, 1-propenyl, 2-propenyl, 1-, 2- or 3-butenyl and the like. The alkenyl group may be substituted or unsubstituted, and when substituted, the substituent group(s) can be substituted at any available connection point, and preferably one or more groups independently selected from the group consisting of alkyl, alkenyl, alkynyl, alkoxy, alkylthio, alkylamino, halogen, mercapto, hydroxy, nitro, cyano, cycloalkyl, heterocycloalkyl, aryl, heteroaryl, cycloalkoxy, heterocycloalkoxy, cycloalkylthio, heterocycle alkylthio.

"Alkynyl" refers to an alkyl group as defined above consisting of at least two carbon atoms and at least one carbon-carbon triple bond, for example ethynyl, propynyl, butynyl and the like. The alkynyl group may be substituted or unsubstituted, and when substituted, the substituent group(s) can be substituted at any available connection point, and preferably one or more groups independently selected from the group consisting of alkyl, alkenyl, alkynyl, alkoxy, alkylthio, alkylamino, halogen, thiol, hydroxy, nitro, cyano, cycloalkyl, heterocycloalkyl, aryl, heteroaryl, cycloalkoxy, heterocycloalkoxy, cycloalkylthio, heterocycle alkylthio.

"Alkenylene" is an unsaturated linear, branched or carbocyclic ring hydrocarbon group containing two monovalent radical centers due to the removal of two hydrogen atoms on the same or two different carbon atoms of the parent alkene. Representative examples include, but are not limited to, vinylene (—CH═CH—), 1,3-propenylene (—CH$_2$CH═CH—), and the like.

"Alkynylene" is an unsaturated linear, branched or carbocyclic ring hydrocarbon group containing two monovalent radical centers due to the removal of two hydrogen atoms on the same or two different carbon atoms of the parent alkyne. Representative examples include, but are not limited to, ethynylene (—C≡C—), 1,3-propynyl (—CH$_2$C≡C—), and the like.

"Arylene" refers to an aromatic hydrocarbon group of 6 to 12 carbon atoms comprising two monovalent radical centers due to the removal of two hydrogen atoms from two different carbon atoms of the parent aromatic ring system. Representative examples include, but are not limited to, 1,2-Phenylene, 1,3-phenylene, 1,4-phenylene and the like.

"Cycloalkyl" refers to a saturated and/or partially unsaturated monocyclic or polycyclic hydrocarbon group having 3 to 20 carbon atoms, preferably 3 to 12 carbon atoms, more preferably 3 to 10 carbon atoms, and most preferably 3 to 8 carbon atoms. Unlimited examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl, and the like. Polycyclic cycloalkyl includes a cycloalkyl having a spiro ring, fused ring or bridged ring.

"Spiro cycloalkyl" refers to a 5 to 20 membered polycyclic group with rings connected through one common carbon atom (called a spiro atom), wherein one or more rings may contain one or more double bonds, but none of the rings has a completely conjugated pi-electron system, preferably 6 to 14 membered spiro cycloalkyl, and more preferably 7 to 10 membered spiro cycloalkyl. According to the number of the common spiro atoms, spiro cycloalkyl may be divided into mono-spiro cycloalkyl, di-spiro cycloalkyl, or poly-spiro cycloalkyl, and preferably a mono-spiro cycloalkyl or di-spiro cycloalkyl, more preferably 4-membered/4-membered, 4-membered/5-membered, 4-membered/6-membered, 5-membered/5-membered, or 5-membered/6-membered mono-spiro cycloalkyl. Unlimited examples of spiro cycloalkyls include, but are not limited to:

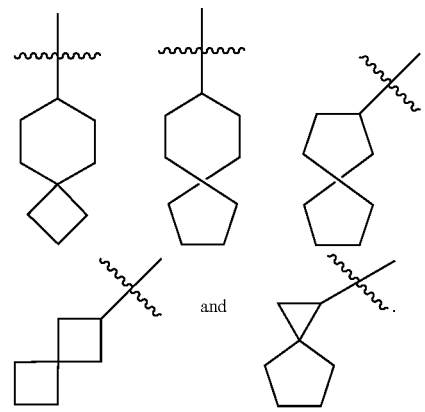

"Fused cycloalkyl" refers to a 5 to 20 membered full-carbon polycyclic group, wherein each ring in the system shares an adjacent pair of carbon atoms with another ring, wherein one or more rings may contain one or more double bonds, but none of the rings has a completely conjugated pi-electron system, preferably 6 to 14 membered fused cycloalkyl, more preferably 7 to 10 membered fused cycloalkyl. According to the number of membered rings, fused cycloalkyl may be divided into bicyclic, tricyclic, tetracyclic or polycyclic fused cycloalkyl, preferably bicyclic or tricyclic fused cycloalkyl, and more preferably 5-membered/5-membered, or 5-membered/6-membered bicyclic fused cycloalkyl. Unlimited examples of fused cycloalkyl include, but are not limited to:

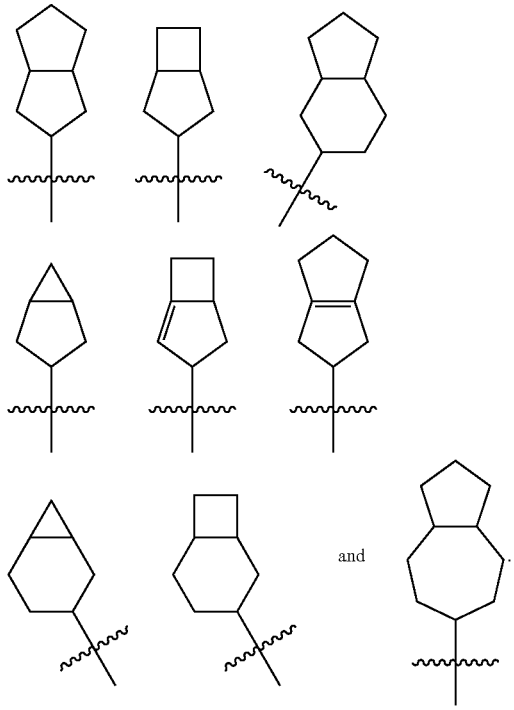

"Bridged cycloalkyl" refers to a 5 to 20 membered full-carbon polycyclic group, wherein every two rings in the system share two disconnected atoms, wherein the rings may have one or more double bonds, but none of the rings has a completely conjugated pi-electron system, preferably 6 to 14 membered bridged cycloalkyl, and more preferably 7 to 10 membered bridged cycloalkyl. According to the number of membered rings, bridged cycloalkyl may be divided into bicyclic, tricyclic, tetracyclic or polycyclic bridged cycloalkyl, and preferably bicyclic, tricyclic or tetracyclic bridged cycloalkyl, and more preferably bicyclic or tricyclic bridged cycloalkyl. Unlimited examples of bridged cycloalkyls include, but are not limited to:

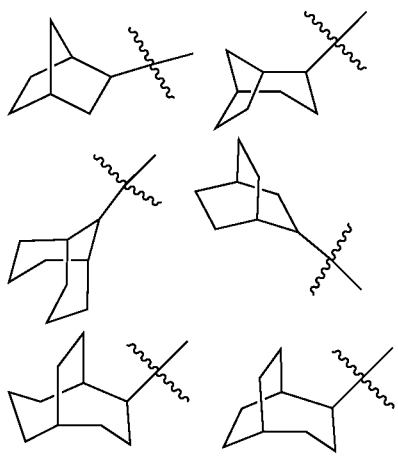

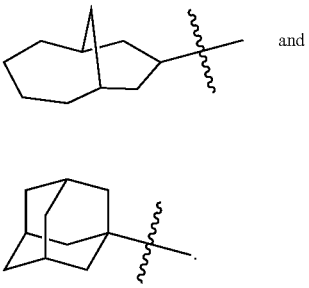

Said cycloalkyl can be fused to aryl, heteroaryl or heterocyclyl, wherein the ring bound to the parent structure is cycloalkyl. Unlimited examples include indanyl, tetrahydronaphthyl, benzocycloheptyl and the like. The cycloalkyl may be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclylthio, oxo, carboxyl, carboxylic ester.

"Heterocyclyl" refers to a 3 to 20 membered saturated and/or partially unsaturated monocyclic or polycyclic hydrocarbon group having one or more heteroatoms selected from the group consisting of N, O, and $S(O)_m$ (wherein m is an integer selected from 0 to 2) as ring atoms, but excluding —O—O—, —O—S— or —S—S— in the ring, and the remaining ring atoms being carbon atoms. Preferably, heterocyclyl has 3 to 12 atoms with 1 to 4 heteroatoms, more preferably 3 to 10 atoms with 1 to 3 heteroatoms, and most preferably 5 to 6 atoms with 1 to 2 or 1 to 3 heteroatoms. Unlimited examples of monocyclic heterocyclyl include, but are not limited to, pyrrolidinyl, imidazolidinyl, tetrahydrofuranyl, tetrahydrothienyl, dihydroimidazolidinyl, dihydrofuranyl, dihydropyrazolidinyl, dihydropyrrolidinyl, piperidyl, piperazinyl, morpholinyl, thiomorpholinyl, homopiperazinyl, pyranyl, and the like, preferably 1,2,5-oxadiazolyl, pyranyl, and morpholinyl. Polycyclic heterocyclyl includes a heterocyclyl having a spiro ring, fused ring or bridged ring.

"Spiro heterocyclyl" refers to a 5 to 20 membered polycyclic heterocyclyl with rings connected through one common atom (called a spiro atom), wherein said rings have one or more heteroatoms selected from the group consisting of N, O, and $S(O)_m$ (wherein m is an integer selected from 0 to 2) as ring atoms and the remaining ring atoms being carbon atoms, wherein one or more rings may contain one or more double bonds, but none of the rings has a completely conjugated pi-electron system; preferably 6 to 14 membered spiro heterocyclyl, and more preferably 7 to 10 membered spiro heterocyclyl. According to the number of common spiro atoms, spiro heterocyclyl may be divided into mono-spiro heterocyclyl, di-spiro heterocyclyl, or poly-spiro heterocyclyl, preferably mono-spiro heterocyclyl or di-spiro heterocyclyl, and more preferably 4-membered/4-membered, 4-membered/5-membered, 4-membered/6-membered, 5-membered/5-membered, or 5-membered/6-membered mono-spiro heterocyclyl. Unlimited examples of spiro heterocyclyls include, but are not limited to:

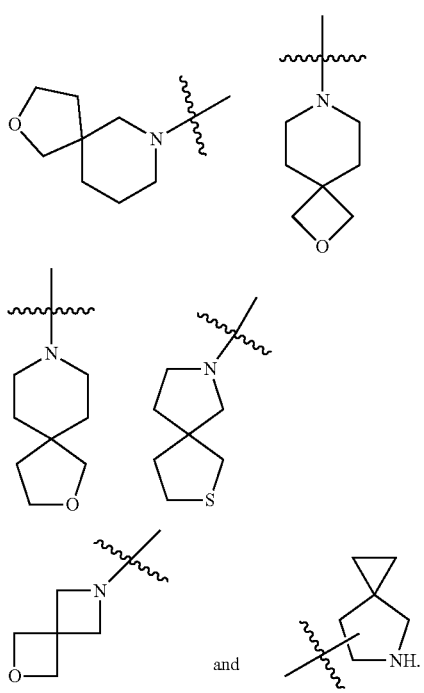

"Fused heterocyclyl" refers to a 5 to 20 membered polycyclic heterocyclyl group, wherein each ring in the system shares an adjacent pair of atoms with another ring, wherein one or more rings may contain one or more double bonds, but none of the rings has a completely conjugated pi-electron system, and wherein said rings have one or more heteroatoms selected from the group consisting of N, O, and $S(O)_m$ (wherein m is an integer selected from 0 to 2) as ring atoms, and the remaining ring atoms being carbon atoms; preferably 6 to 14 membered fused heterocyclyl, and more preferably 7 to 10 membered fused heterocyclyl. According to the number of membered rings, fused heterocyclyl may be divided into bicyclic, tricyclic, tetracyclic or polycyclic fused heterocyclyl, preferably bicyclic or tricyclic fused heterocyclyl, and more preferably 5-membered/5-membered, or 5-membered/6-membered bicyclic fused heterocyclyl. Unlimited examples of fused heterocyclyl include, but are not limited to:

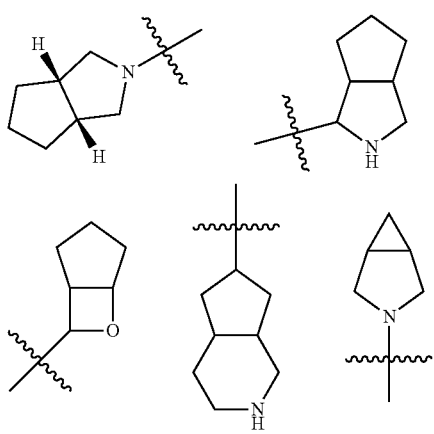

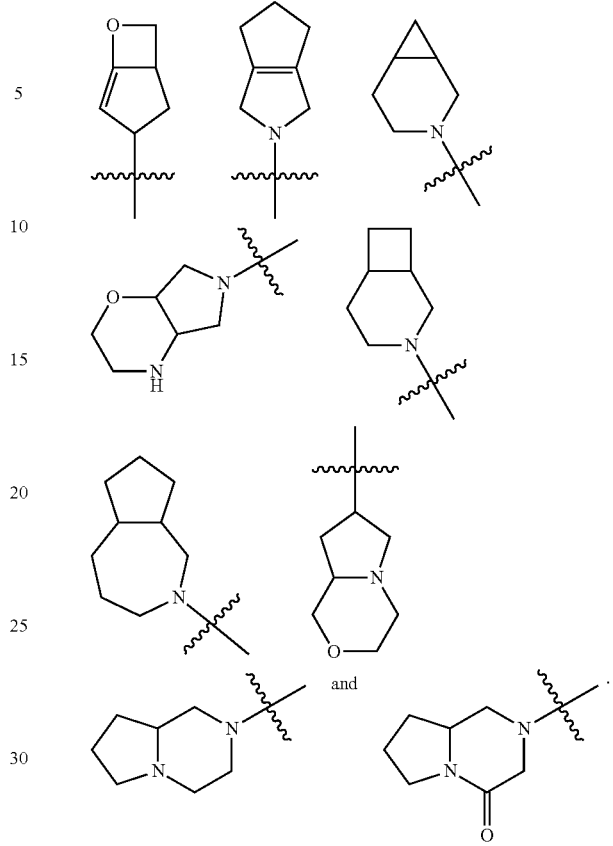

"Bridged heterocyclyl" refers to a 5 to 14 membered poly cyclic heterocyclyl group, wherein every two rings in the system share two disconnected atoms, wherein the rings may have one or more double bonds, but none of the rings has a completely conjugated pi-electron system, and the rings have one or more heteroatoms selected from the group consisting of N, O, and $S(O)_m$ (wherein m is an integer selected from 0 to 2) as ring atoms, and the remaining ring atoms being carbon atoms; preferably 6 to 14 membered bridged heterocyclyl, and more preferably 7 to 10 membered bridged heterocyclyl. According to the number of membered rings, bridged heterocyclyl may be divided into bicyclic, tricyclic, tetracyclic or polycyclic bridged heterocyclyl, and preferably bicyclic, tricyclic or tetracyclic bridged heterocyclyl, and more preferably bicyclic or tricyclic bridged heterocyclyl. Unlimited examples of bridged heterocyclyls include, but are not limited to:

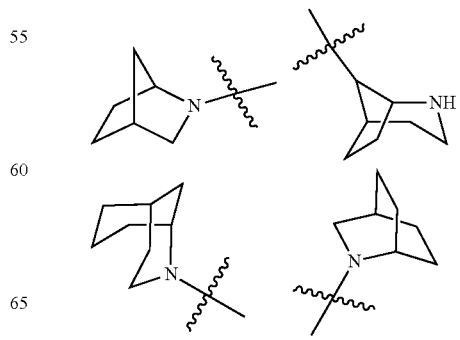

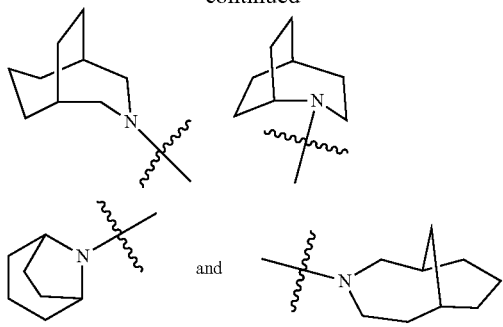

Said heterocyclyl can be fused to aryl, heteroaryl or cycloalkyl, wherein the ring bound to the parent structure is heterocyclyl. Unlimited examples include, but are not limited to:

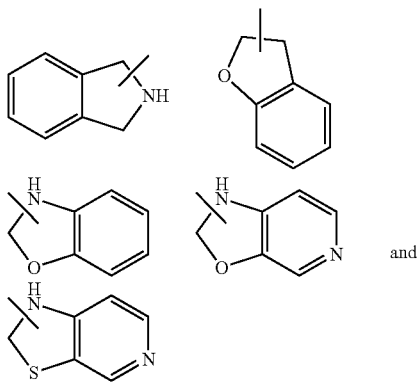

etc.

The heterocyclyl may be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclylthio, oxo, carboxyl, carboxylic ester.

"Aryl" refers to a 6 to 14 membered full-carbon monocyclic ring or polycyclic fused ring (i.e. each ring in the system shares an adjacent pair of carbon atoms with another ring in the system) group having a completely conjugated pi-electron system; preferably 6 to 10 membered aryl, more preferably phenyl and naphthyl, and most preferably phenyl. The aryl can be fused to heteroaryl, heterocyclyl or cycloalkyl, wherein the ring bound to parent structure is aryl. Unlimited examples include, but are not limited to:

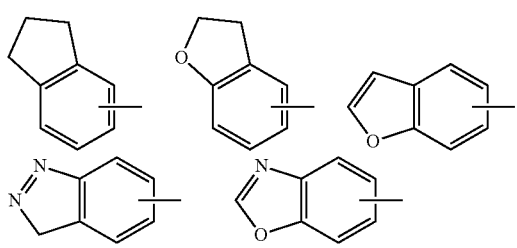

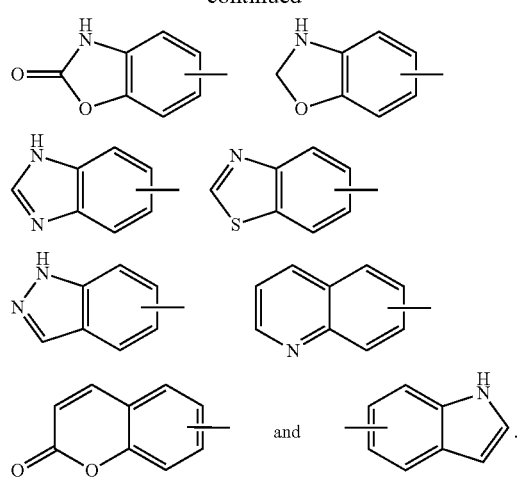

The aryl may be optionally substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclylthio, carboxyl, carboxylic ester.

"Heteroaryl" refers to 5 to 14 membered aryl having 1 to 4 heteroatoms selected from the group consisting of O, S and N as ring atoms and remaining ring atoms being carbon atoms; preferably 5 to 10 membered heteroaryl having 1 to 3 heteroatoms, more preferably 5- or 6-membered heteroaryl having 1 to 2 heteroatoms. Example include, but not limited to, imidazolyl, furyl, thienyl, thiazolyl, pyrazolyl, oxazolyl, pyrrolyl, tetrazolyl, pyridyl, pyrimidinyl, thiadiazolyl, pyrazinyl, and the like. Preferable examples include imidazolyl, thiazolyl, pyrazolyl, pyrimidinyl, thiazolyl. More preferable examples include pyrazolyl and thiazolyl. The heteroaryl can be fused to aryl, heterocyclyl or cycloalkyl, wherein the ring bound to parent structure is heteroaryl. Unlimited examples include, but are not limited to:

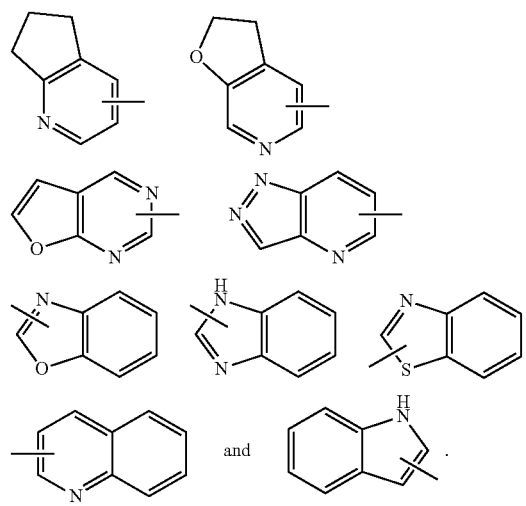

The heteroaryl may be optionally substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclylthio, carboxyl, carboxylic ester.

"Optional" or "optionally" means that the event or circumstance described subsequently can, but need not, occur, and such description includes the situation in which the event or circumstance may or may not occur. For example, "the heterocyclic group optionally substituted with an alkyl" means that an alkyl group can be, but need not be, present, and such description includes the situation of the heterocyclic group being substituted with an alkyl and the heterocyclic group being not substituted with an alkyl.

"Substituted" refers to one or more hydrogen atoms in a group, preferably up to 5, more preferably 1 to 3 hydrogen atoms, independently substituted with a corresponding number of substituents. It goes without saying that the substituents only exist in their possible chemical position. The person skilled in the art is able to determine whether the substitution is possible or impossible by experiments or theory without paying excessive efforts. For example, when amino or hydroxy having free hydrogen is bound to a carbon atoms having unsaturated bonds (such as olefinic) may be unstable.

A "pharmaceutical composition" refers to a mixture of one or more of the compounds according to the present invention or physiologically/pharmaceutically acceptable salts or prodrugs thereof and other chemical components such as physiologically/pharmaceutically acceptable carriers and excipients. The purpose of a pharmaceutical composition is to facilitate administration of a compound to an organism and the absorption of the active ingredient and thus displaying biological activity.

"Pharmaceutically acceptable salts" refers to salts of the compounds of the invention that are safe and effective in mammals and have the desired biological activity.

The pharmaceutically acceptable salts of the compound of formula I, II, and III according to the present invention may be an acid addition salt or a basic addition salts. The acid may be inorganic acids including, but not limited to, hydrochloric acid, sulfuric acid, phosphoric acid, hydrobromic acid; or organic acids including, but not limited to, citric acid, maleic acid, oxalic acid, formic acid, acetic acid, propionic acid, glycolic acid, benzoic acid, fumaric acid, trifluoroacetic acid, succinic acid, tartaric acid, lactic acid, glutamic acid, aspartic acid, salicylic acid, pyruvic acid, methanesulfonic acid, benzenesulfonic acid, p-toluenesulfonic acid. The base may be inorganic bases including, but not limited to, sodium hydroxide, potassium hydroxide, magnesium hydroxide, calcium hydroxide; or organic bases including, but not limited to, ammonium hydroxide, triethylamine, arginine, or lysine.

In another aspect of the invention, the antibody drug conjugate according to the present invention can be prepared as a clinically useful pharmaceutical composition. According to clinical indications, administration route and method, the pharmaceutical preparations include, but are not limited to, oral preparations such as tablets, gels, soft/hard capsules, emulsions, dispersible powders, granules, water/oil suspoemulsions; injections including intravenous injections, intramuscular injections, intraperitoneal injections, rectal administration suppositories, intracranial injections, which may be aqueous solutions or oil solutions; topical formulations including creams, ointments, gels, water/oil solutions, and packages; inhalation formulations including fine powders, liquid aerosols, and various dosage forms suitable for in vivo implantation.

The pharmaceutical composition of the present invention may be added with conventional pharmaceutical excipients as needed. These excipients should comply with the pharmaceutical preparation process rules and be compatible with the active ingredient. The solid oral preparation excipients include, but are not limited to, mannitol, lactose, starch, magnesium stearate, cellulose, glucose, sucrose, cyclodextrin, and vitamin E-PEG 1000 which promotes intestinal absorption. Oral formulations may be added with suitable colorants, sweeteners, flavoring agents and preservatives.

It is well-known to those skilled in the art that the dosage of the drug to be administered depends on a variety of factors including, but not limited to, the activity of the specific compound employed, the age of the patient, the patient's body weight, the patient's condition, diet, time of administration, mode of administration, rate of excretion, combination of drugs, and the like. In addition, the optimal treatment modalities such as the mode of treatment, the daily dosage of the compound of the general formula, or the type of pharmaceutically acceptable salt can be verified according to conventional treatment regimens.

Preparation Method for ADCs

The ADCs according to the invention can be prepared via the method as following.

Method 1 is shown in scheme 4.

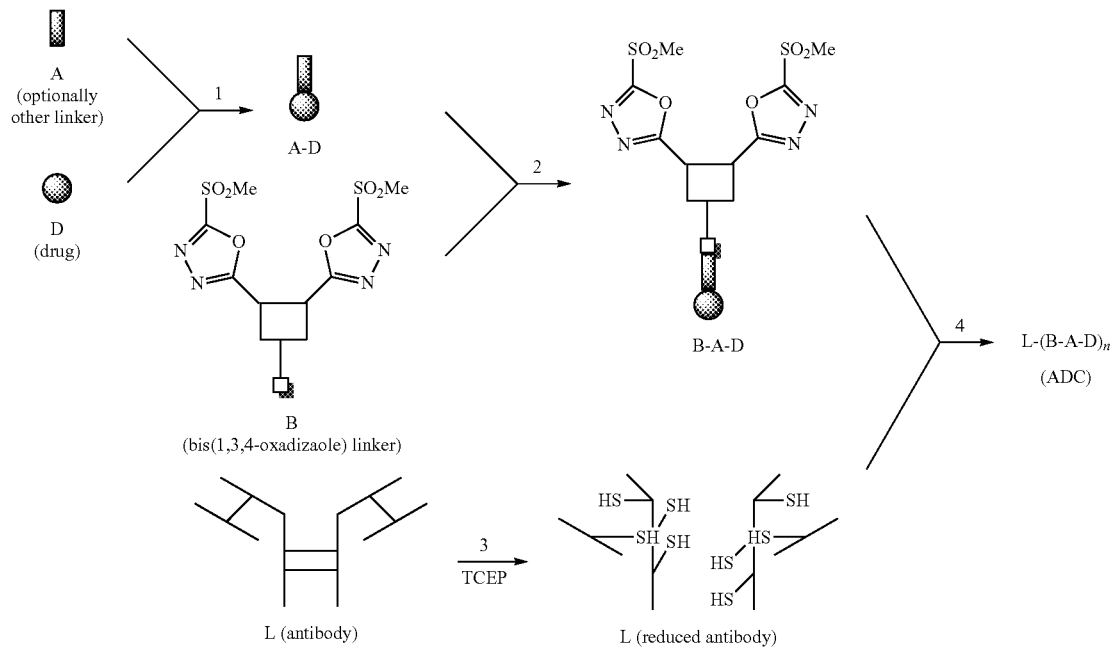

Step 1: The optionally other linker (A) and a drug (D) are conjugated to afford an optionally other linker-dug (A-D);

Step 2 The bis(1,3,4-oxadiazole) linker (B) and A-D are conjugated to give bis(1,3,4-oxadiazole) linker-optionally other link-drug (B-A-D);

Step 3: The inter-chain disulfide bonds of an antibody (L) are reduced to produce a total of eight sulfhydryl groups;

Step 4: B-A-D is crosslinked with the reduced sulfhydryl groups or other amino acid residues of the antibody to afford antibody-drug conjugate L-(B-A-D)$_n$.

Method 2 is shown in scheme 5.

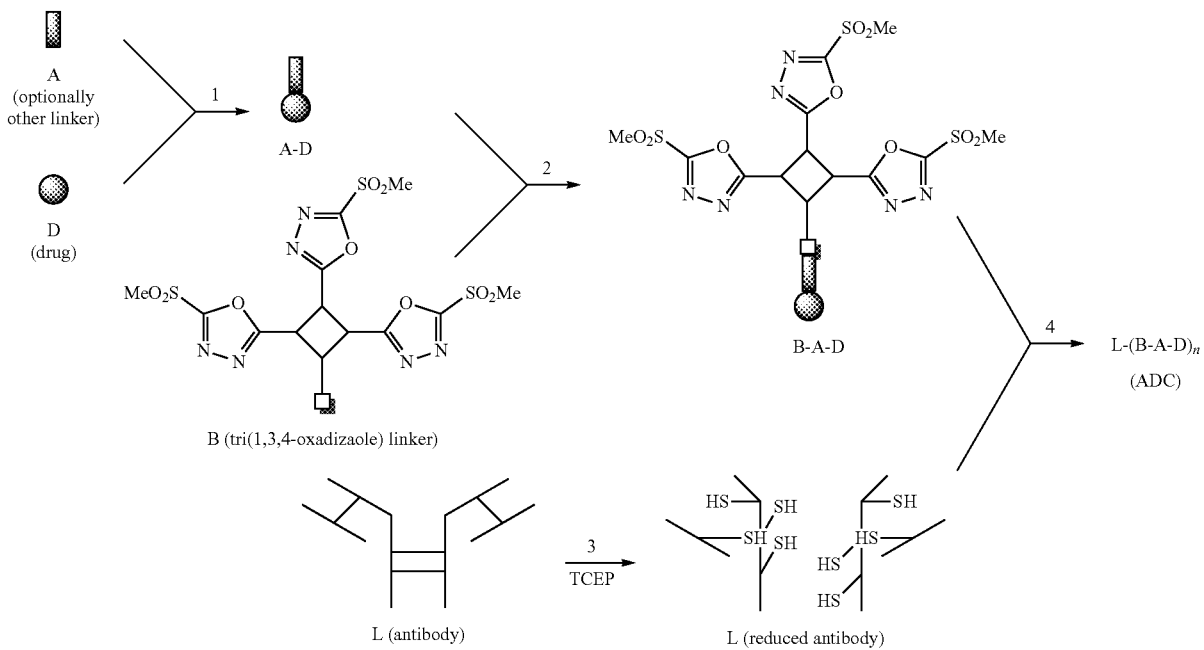

Step 1: The optionally other linker (A) and a drug (D) are conjugated to afford an optionally other linker-Drug (A-D);

Step 2: A tri(1,3,4-oxadiazole) linker (B) and A-D are conjugated to give tris(1,3,4-oxadiazole) linker-optionally other linker-drug (B-A-D);

Step 3: The inter-chain disulfide bonds of an antibody (L) are reduced to produce a total of eight sulfhydryl groups;

Step 4: B-A-D is crosslinked with the sulfhydryl groups or other amino acid residues of the antibody to afford antibody-drug conjugate L-(B-A-D)$_n$.

Method 3 is shown in scheme 6.

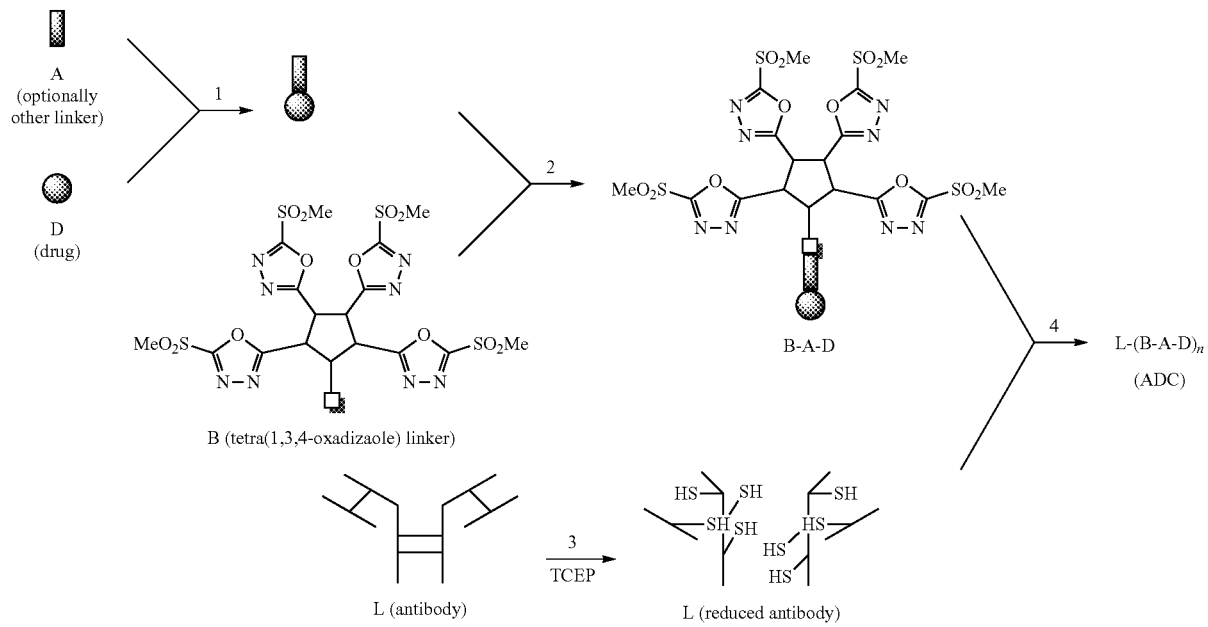

Scheme 6

Step 1: The optionally other linker (A) and a drug (D) are conjugated to afford a linker-Drug (A-D);

Step 2: A tetra(1,3,4-oxadiazole) linker (B) and A-D are conjugated to give tri(1,3,4-oxadiazole) linker-optionally other linker-drug (B-A-D);

Step 3: The inter-chain disulfide bonds of an antibody (L) are reduced to produce a total of eight sulfhydryl groups;

Step 4: B-A-D is crosslinked with the sulfhydryl groups or other amino acid residues of the antibody to afford antibody-drug conjugate L-(B-A-D)$_n$.

Use

The antibody-drug conjugates according to the present invention target a special cell population and bind to the specific cell surface proteins (antigens) to form a complex, followed by the internalization of the complex into the cell and releasing of the drug within the cell in active form.

The antibody-drug conjugates according to the present invention target a special cell population and bind to the specific cell surface proteins (antigens) to take effects; or release drugs outside the cell, followed by the permeation of the drugs into the cell to take effects.

The present invention provides a method for the treatment of cancers or other tumors in animal subjects comprising administration of a therapeutically effective amount of the antibody-drug conjugate according to the invention to a subject suffering from cancers or other tumors.

The present invention provides a method for the treatment of autoimmune disease or infectious disease comprising administration of a therapeutically effective amount of the antibody-drug conjugate according to the invention to a subject suffering from autoimmune diseases or infectious diseases.

The above technical features or features mentioned in the following examples can be combined at will. All the features disclosed in the present invention can be applied together with any combination, and each feature can be substituted with any identical, equal, or similar features. Unless otherwise specific state, all disclosed features are only general examples of the equal or similar features.

The present invention has the following main advantages:
1. The present invention provides three novel types of linkers including bis(1,3,4-oxadiazole), tri(1,3,4-oxadiazole) and tetra(1,3,4-oxadiazole). Correspondingly, these linkers could not only control the average DAR values of the ADCs around 4, 3, and 2, but also provide the main components with DAR value of 4, 3 and 2, respectively. Therefore, the homogeneity of the ADC products can be greatly improved.
2. The bis(1,3,4-oxadiazole) linker according to the present invention contains two 2-methylsulfonyl-1,3,4-oxadiazole groups, which can be used to crosslink the antibody interchain cysteine or other amino acid residues, leading to a conjugated product containing a main component (85%+) with a DAR value of 4.
3. The tri(1,3,4-oxadiazole) linker according to the present invention contains three 2-methylsulfonyl-1,3,4-oxadiazole groups, which can be used to crosslink the antibody interchain cysteine or other amino acid residues, leading to a conjugated product containing a main component (85%+) with a DAR value of 3.
4. The tetra(1,3,4-oxadiazole) linker according to the present invention contains four 2-methylsulfonyl-1,3,4-oxadiazole groups, which can be used to crosslink the antibody interchain cysteine or other amino acid residues, leading to a conjugated product containing a main component (85%+) with a DAR value of 2.
5. The conjugation technology according to the present invention is applicable to most antibodies, which can avoid complicated antibody engineering used to introduce specific sites for coupling. Therefore, the conjugation technology may have very broad application prospect.

EXAMPLES

Figure 1:
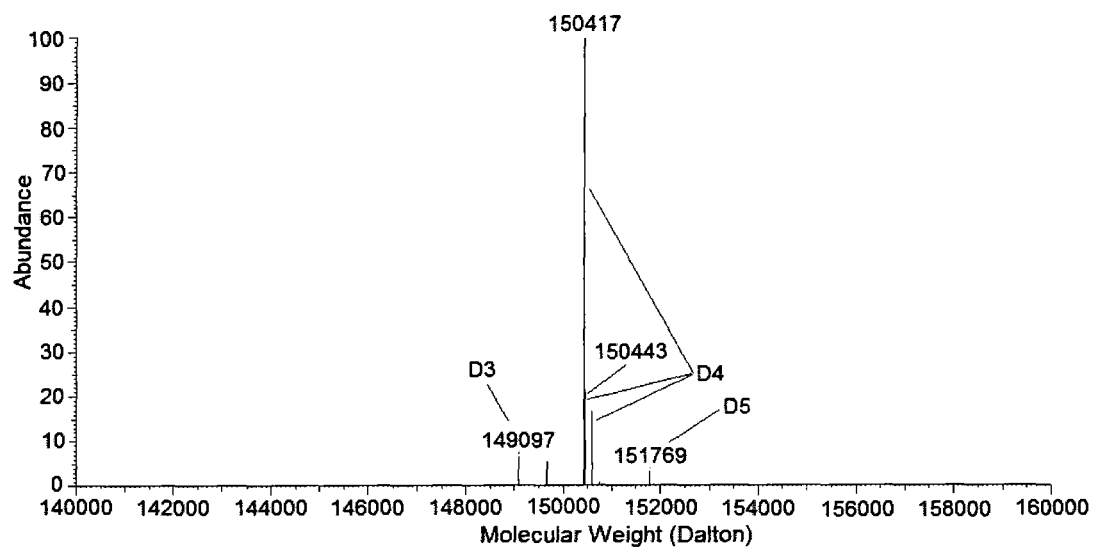
FIG. 1 illustrates the native MS spectrum of H-1-vcM-MAE of the invention.

The present invention will be further described in details with the following examples. However, it should be understood that these examples are used to illustrate the present invention, but should not be considered as limiting the scope of the invention. The unstated experiment conditions are generally according to routine conditions or conditions suggested by manufacturers. All reactions were conducted under nitrogen atmosphere, except for hydrogenation reaction.

Unless otherwise defined, all of the professional and scientific terms used in the present invention have the same meaning as those familiar by the expertise in the art. Furthermore, any method or material similar or equal to those used in the present invention can be applied herein. The optimized methods and materials used in the present invention are only used for illustration while not for limitation.

ABBREVIATION

Ab antibody
Ac acetyl
ACN acetonitrile
BOC (Boc) tert-butoxycarbonyl
t-Bu tert-butyl
DCM dichloromethane
DIEA diisopropylethylamine
DMF N,N-dimethylformamide
ELISA enzyme linked immunosorbent assay
Et ethyl
EA (EtOAc) ethyl acetate
Eq equivalent
g gram
h hour
HOSu N-hydroxy succinimide
HIC hydrophobic interaction chromatography
HPLC high performance liquid chromatography
LC-MS liquid chromatography-mass spectrum
MeOH methanol
mAb monoclonal antibody
Me methyl
min minute
ML milliliter
MS mass spectrometry
nm nanometer
μg microgram
μL microliter
PE petroleum ether
prep-RP-HPLC preparative-reverse phase-high performance liquid chromatography
rt room temperature
$R_t$ retention time
SDS-PAGE sodium dodecyl sulfate polyacrylamide gel electrophoresis
SEC size exclusion chromatography
TEA triethylamine
TFA trifluoroacetic acid
THF tetrahydrofuran
TLC thin layer chromatography
TsCl p-tolyl chloride Unless otherwise stated, all of the anhydrous solvents are purchased from the suppliers and kept under nitrogen atmosphere. All other reagents and solvents purchased are of high purity and need not to be purified before use.

$^1$H NMR spectrum was collected on a Bruker Avance III 500 MHz instrument. Chemical shift (b) unit is ppm, and the reference reagent is TMS ($\delta$=0).

For LC-MS, low resolution mass spectrum was collected on Agilent 6110 (acid method) or 6120B (base method) mass spectrometers coupled with Hewlett-Packard Agilent 1200 HPLC.

Method 1: Waters Sunfire C18 reverse phase column (4.60×50 mm, 3.5 μm) is used in the acid HPLC method for separation, and the eluting gradient is 5%-95% B (acetonitrile, containing 0.01% TFA) in A (water, containing 0.01% TFA) over 1.4 min. The flow rate is 2.3 mL/min, and the column temperature is 50° C.

Method 2: Waters Sunfire C18 reverse phase column (4.60×50 mm, 3.5 μm) is used in the acid HPLC method for separation, and the eluting gradient is 5%-95% B (acetonitrile, containing 0.01% TFA) in A (water, containing 0.01% TFA) over 1.4 min. The flow rate is 2.0 mL/min, and the column temperature is 50° C.

Method 3: Waters Sunfire C18 reverse phase column (3.0×30 mm, 2.5 μm) is used in the acid HPLC method for separation, and the eluting gradient is 5%-95% B (acetonitrile, containing 0.01% TFA) in A (water, containing 0.01% TFA) over 1.5 min. The flow rate is 1.5 mL/min, and the column temperature is 50° C.

Method 4: Waters Sunfire C18 reverse phase column (4.6×50 mm, 3.5 μm) is used in the acid HPLC method for separation, and the eluting gradient is 5%-95% B (acetonitrile, containing 0.01% TFA) in A (water, containing 0.01% TFA) over 1.2 min. The flow rate is 2.0 mL/min, and the column temperature is 50° C.;

Method 5: Waters Xbridge C18 reverse phase column (4.60×50 mm, 3.5 μm) is used in the base HPLC method for separation, and the eluting gradient is 5%-95% B (acetonitrile) in A (water, containing 10 mM ammonium bicarbonate) over 1.5 min. The flow rate is 2.0 mL/min, and the column temperature is 40° C.

Purification by preparative HPLC is conducted on a Gilson instrument. Waters Sunfire C18 reverse phase column (250×19 mm, 10 μm) is used for separation.

Method 6: The acid HPLC preparation method. Mobile phase: A is aqueous solution containing 0.1% TFA; B is ACN. The flow rate is 20 mL/min.

SK-BR-3 human breast cancer cell is purchased from ATCC. Her2 antigen is purchased from Sino Biological Inc (Beijing). Antibody H (Herceptin Biosimilar, IgG1) is purchased from Genor Biopharma Co. Ltd. (Shanghai). The enzyme labeled anti-antibody is purchased from Sigma (Shanghai). Substrate solution is purchased from Decent Biotech (Shanghai). Cell Counting Kit (CCK-8) cell proliferation-cytotoxicity assay kit is purchased from Dojindo (Shanghai).

PREPARATION EXAMPLES

Synthesis of Key Intermediates (KIs)

Preparation Example 1

Synthesis of 2-(chloromethyl)-5-(methylthio)-1,3,4-oxadiazole (KI-1)

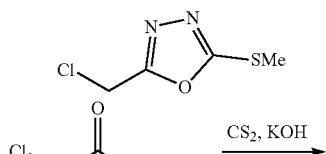

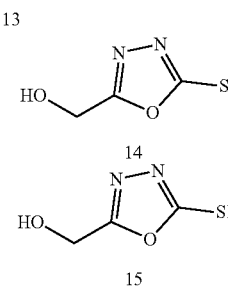

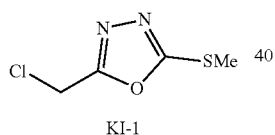

Step 1: Synthesis of (5-mercapto-1,3,4-oxadiazol-2-yl)methanol (14)

2-Hydroxyacetohydrazide (13, 9.99 g) was dissolved in MeOH (100 mL), to which carbon disulfide (16.87 g, 0.22 mol) and potassium hydroxide (85%, 14.63 g, 0.22 mol) were sequentially added. The reaction mixture was stirred at rt for 1 h, and then refluxed for 3 h. After cooling down, the mixture was concentrated under reduced pressure to give yellow solid-liquid residue. MeOH was added to the residue, to which concentrated hydrochloric acid was dropwise added to adjust pH to 3. The mixture was concentrated under reduced pressure to give a yellow solid, which was further purified by silica gel chromatography (PE/EA 2:1) to give compound 14 (1.50 g) as yellow oil.

Step 2: Synthesis of (5-(methylthio)-1,3,4-oxadiazol-2-yl)methanol (15)

Compound 14 (1.50 g, 11.36 mmol) was dissolved in THF (20 mL), and the solution was cooled to 0° C. with an ice-water bath, to which iodomethane (2.42 g, 17.04 mmol) and TEA (1.72 g, 17.04 mmol) were added sequentially. The reaction mixture was stirred at rt for 2 h, and then concentrated under reduced pressure to remove the solvent. The residue was purified by silica gel chromatography (PE/EA 1:1) to give compound 15 (900 mg) as yellow oil.

Step 3: Synthesis of 2-(chloromethyl)-5-(methylthio)-1,3,4-oxadiazole (KI-1)

Compound 15 (900 mg, 6.16 mmol) was dissolved in DCM (10 mL), and the solution was cooled to 0° C., to which TsCl (2.35 g, 12.32 mmol) and TEA (1.24 g, 12.32 mmol) were sequentially added. The reaction mixture was stirred at rt for 2 h, and then concentrated under reduced pressure to remove the solvent. The residue was purified by silica gel chromatography (PE/EA 10:1) to give compound KI-1 (520 mg) as yellow oil.

LC-MS (method 1): $R_t$=1.56 min; m/z (ES$^+$)=165.1 (M+H)$^+$.

$^1$H NMR (500 MHz, CDCl$_3$) δ 4.68 (s, 2H), 2.74 (s, 3H).

Preparation Example 2

Synthesis of 2-(chloromethyl)-5-(methylthio)-1,3,4-oxadiazole (KI-2)

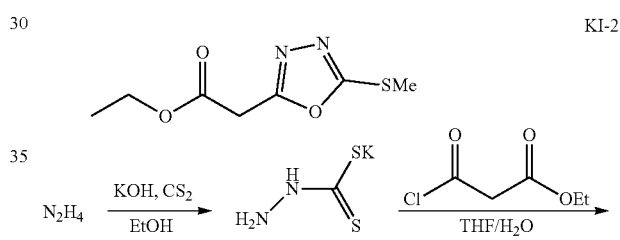

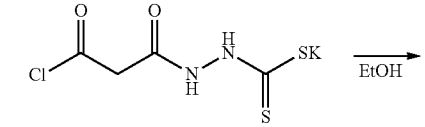

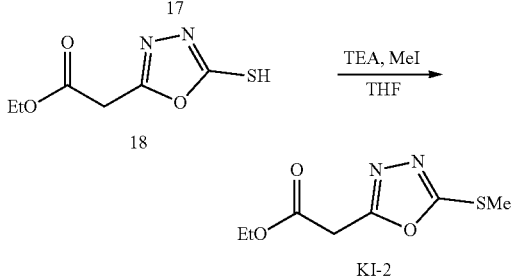

Step 1: Synthesis of Potassium Hydrazinecarbodithioate (16)

Aqueous hydrazine solution (80%, 8.0 g, 0.20 mol) was dissolved in ethanol (50 mL), to which carbon disulfide (15.2 g, 0.2 mol) and potassium hydroxide (85%, 13.18 g, 200 mmol) were sequentially added. The reaction mixture was stirred at rt for 1 h, and then concentrated under reduced pressure to remove the solvent. MeOH (50 mL) was added to the crude product, and the white solid was collected by filtration, washed, and dried to give compound 16 (19.5 g).

Step 2: Synthesis of Potassium 2-(3-ethoxy-3-oxo-propanoyl)hydrazinecarbodithioate (17)

Compound 16 (21.02 g, 144 mmol) was dissolved in THF/H₂O (40 mL, v/v 1/1), and the solution was cooled to 5° C., to which ethyl 3-chloro-3-oxopropanoate (21.67 g, 144 mmol) was added dropwise in 30 min, followed by dropwise addition of aqueous potassium hydrocarbonate solution (14.40 g in 20 mL water) in 30 min. After the addition, the reaction mixture was stirred at rt for 12 h, and then concentrated under reduced pressure to remove the solvent to give the crude product 17 (16.5 g), which was used for next step without further purification.

Step 3: Synthesis of ethyl 2-(5-mercapto-1,3,4-oxadiazol-2-yl)acetate (18)

Compound 17 (16.5 g) was dissolved in ethanol (100 mL), and the solution was heated to reflux for 1.5 h. After cooling down, the mixture was concentrated to remove the solvent. EA (200 mL) and brine (50 mL) were added to the residue, to which concentrated hydrochloric acid was added dropwise to adjust pH to 3. The aqueous phase was extracted by EA (200 mL×3). The combined organic phase was sequentially washed with brine, dried, filtered, and concentrated under reduced pressure. The residue was purified by silica gel chromatography (PE/EA 1:1) to give compound 18 (8.5 g) as yellow oil.

LC-MS (method 1): R$_t$=1.38 min; m/z (ES⁺)=188.9 (M+H)⁺.

¹H NMR (500 MHz, CDCl₃) δ 4.26-4.22 (m, 2H), 3.45 (s, 2H), 1.30 (t, 3H).

Step 4: Synthesis of ethyl 2-(5-(methylthio)-1,3,4-oxadiazol-2-yl)acetate (KI-2)

Compound 18 (2.50 g, 13.3 mmol) was dissolved in THF (30 mL), and the solution was cooled to 0° C., to which iodomethane (2.83 g, 19.95 mmol) and TEA (2.01 g, 19.95 mmol) were added sequentially. The reaction mixture was stirred at rt for 30 min, and then concentrated under reduced pressure to remove the solvent. The residue was purified by silica gel chromatography (PE/EA 1:1) to give compound KI-2 (2.44 g) as yellow oil.

LC-MS (method 1): R$_t$=1.55 min; m/z (ES⁺)=203.1 (M+H)⁺.

¹H NMR (500 MHz, CDCl₃) δ 4.22 (q, 2H), 3.92 (s, 2H), 2.71 (s, 3H), 1.27 (t, 3H).

Preparation Example 3

Synthesis of 2-(methylthio)-5-vinyl-1,3,4-oxadiazole (KI-3)

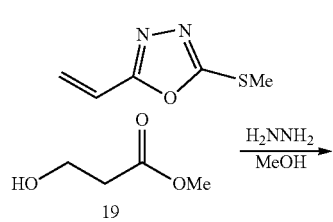

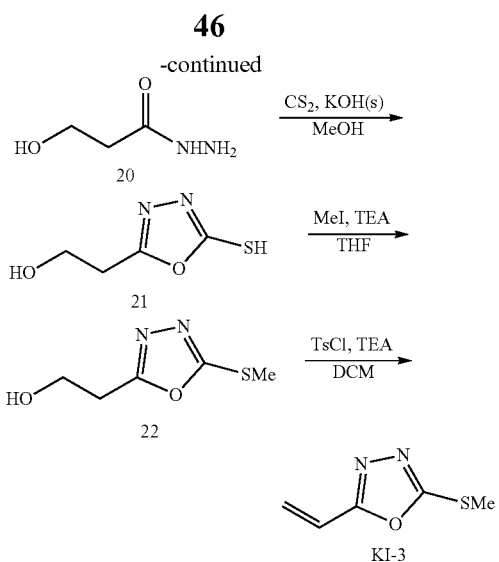

Step 1: Synthesis of 3-hydroxypropanehydrazide (20)

Methyl 3-hydroxypropanoate (19) was dissolved in methanol (200 mL), to which aqueous hydrazine solution (80%, 12.0 g, 192 mmol) was added. The reaction mixture was heated to reflux for 4 h, and then concentrated under reduced pressure to remove the solvent. The crude product 20 (15.3 g) was used directly for next step without further purification.

Step 2: Synthesis of 2-(5-mercapto-1,3,4-oxadiazol-2-yl)ethanol (21)

Compound 20 (9.50 g, 91.3 mmol) was dissolved in MeOH (100 mL), to which carbon disulfide (13.88 g, 183 mmol) and potassium hydroxide (85%, 12.03 g, 183 mmol) were sequentially added. The reaction mixture was stirred at rt for 2 h, and then heated to reflux for 3 h. The mixture was concentrated under reduced pressure to give yellow crude product, to which MeOH (30 mL) was added and concentrated hydrochloric acid was added to adjust pH to 2~3. The solution was concentrated under reduced pressure to give a yellow crude, which was further purified by silica gel chromatography (PE/EA 1:1) to give compound 21 (9.60 g) as a yellow solid.

LC-MS (method 1): R$_t$=0.93 min; m/z (ES⁺)=147.1 (M+H)⁺.

Step 3: Synthesis of 2-(5-(methylthio)-1,3,4-oxadiazol-2-yl)ethanol (22)

Compound 21 (9.60 g, 65.8 mmol) was dissolved in THF (100 mL), and the solution was cooled to 0° C., to which iodomethane (14.0 g, 98.6 mmol) and TEA (9.96 g, 98.63 mmol) were added sequentially. The reaction mixture was stirred at rt for 2 h, and then concentrated under reduced pressure to remove the solvent. The residue was purified by silica gel chromatography (PE/EA 1:1) to give compound 22 (3.2 g) as yellow oil.

LC-MS (method 1): R$_t$=1.24 min; m/z (ES⁺)=161.0 (M+H)⁺.

Step 4: Synthesis of 2-(methylthio)-5-vinyl-1,3,4-oxadiazole (KI-3)

Compound 22 (3.20 g, 20.0 mmol) was dissolved in DCM (50 mL), and the solution was cooled to 0° C., to which TsCl (7.63 g, 40.0 mmol) and TEA (6.06 g, 60 mmol) were sequentially added. The reaction mixture was stirred at rt for 2 d, and then concentrated to give a residue. Further purification by silica gel chromatography (PE/EA 10:1) gave the compound KI-3 (1.90 g) as a yellow solid.

LC-MS (method 1): $R_t$=1.34 min; m/z (ES$^+$)=143.1 (M+H)$^+$.

$^1$H NMR (500 MHz, CDCl$_3$) δ 6.79 (dd, 1H), 6.19 (d, 1H), 5.89 (d, 1H), 2.73 (s, 3H).

Example 1

Synthesis of 3,4-bis(5-(methylsulfonyl)-1,3,4-oxadiazol-2-yl)butanoic Acid (Linker 1)

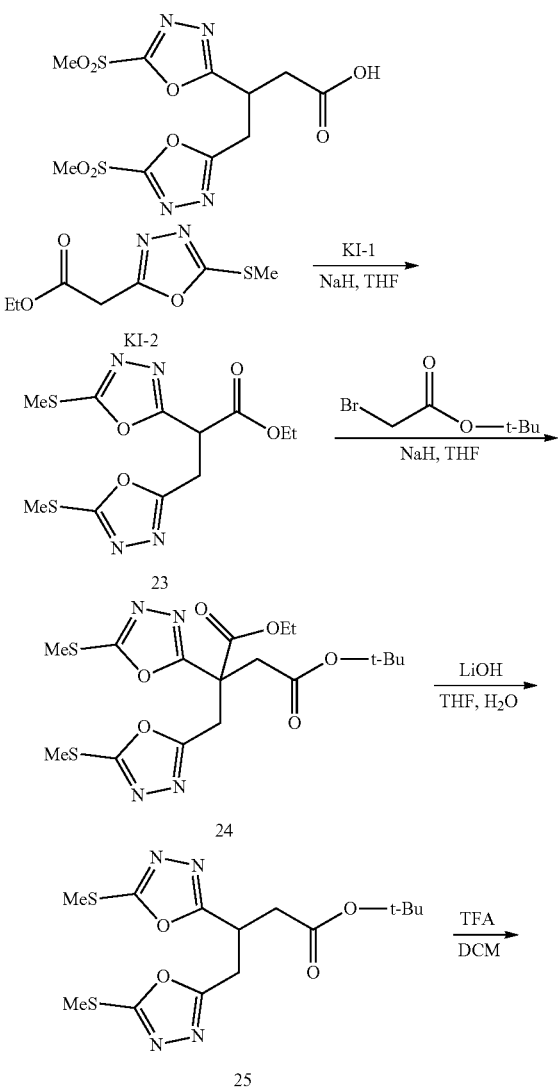

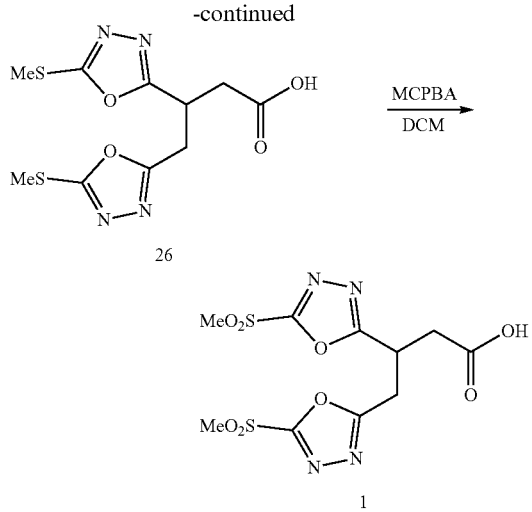

Step 1: Synthesis of ethyl 2,3-bis(5-(methylthio)-1,3,4-oxadiazol-2-yl)propanoate (23)

KI-2 (51 mg, 0.25 mmol) was dissolved in anhydrous THF (5 mL), to which sodium hydride (60% dispersion in mineral oil, 20 mg, 0.50 mmol) was added. The reaction mixture was stirred at rt for 30 min, and then KI-1(41 mg, 0.25 mmol) was added, followed by stirring at 35° C. for 3 h. The mixture was concentrated under reduced pressure, and the residue was purified by silica gel chromatography (PE/EA 3:2) to give compound 23 (35 mg) as colorless oil.

LC-MS (method 1): $R_t$=1.68 min; m/z (ES$^+$)=331.1 (M+H)$^+$.

$^1$H NMR (500 MHz, CDCl$_3$) δ 4.53 (t, 1H), 4.21-4.14 (m, 2H), 3.66-3.61 (m, 1H), 3.53-3.48 (m, 1H), 2.65 (s, 3H), 2.62 (s, 3H), 1.20 (t, 3H).

Step 2: Synthesis of 4-tert-butyl 1-ethyl 2-(5-(methylthio)-1,3,4-oxadiazol-2-yl)-2-((5-(methylthio)-1,3,4-oxadiazol-2-yl)methyl)succinate (24)

Compound 23 (50 mg, 0.15 mmol) was dissolved in THF (3 mL), to which sodium hydride (12 mg, 0.30 mmol) was added. The reaction mixture was stirred at rt for 30 min, to which tert-butyl bromoacetate (49 μL, 0.30 mmol) was added, followed by stirring at rt for 3 h. Hydrochloric acid (0.5 M) was added to quench the reaction, and the mixture was extracted by EA. The organic phase was washed with water, dried, filtered and concentrated under reduced pressure. The residue was purified by silica gel chromatography (PE/EA 5:1 to 3:1) to give compound 24 (40 mg) as colorless oil.

LC-MS (method 1): $R_t$=1.98 min; m/z (ES$^+$)=115.1 (M+H)$^+$.

$^1$H NMR (500 MHz, CDCl$_3$) δ4.28-4.21 (m, 2H), 3.91-3.84 (d, 2H), 3.35 (d, 1H), 3.21 (d, 1H), 2.71 (s, 3H), 2.67 (s, 3H), 1.42 (s, 9H), 1.25 (t, 3H).

Step 3: Synthesis of tert-butyl 3,4-bis(5-(methylthio)-1,3,4-oxadiazol-2-yl)butanoate (25)

Compound 24 (40 mg, 90 μmol) was dissolved in THF (0.2 mL), to which aqueous lithium hydroxide solution (1.0 M, 180 μL, 180 μmol) was added. The reaction mixture was stirred at rt for 2 h, to which concentrated hydrochloric acid (38 µL, 450 mmol) was added, followed by stirring at rt for 16 h. The mixture was extracted by EA, and the organic phase was washed with water, dried, and concentrated under reduced pressure sequentially. The residue was purified by silica gel chromatography (PE/EA 5:1 to 3:1) to give compound 25 (26 mg) as colorless oil.

LC-MS (method 1): R$_f$=1.85 min; m/z (ES$^+$)=373.1 (M+H)$^+$.

$^1$H NMR (500 MHz, CDCl$_3$) δ3.94-3.91 (m, 1H), 3.42-3.26 (m, 2H), 2.90-2.74 (m, 2H), 2.68 (s, 3H), 2.67 (s, 3H), 1.40 (s, 9H).

Step 4: Synthesis of 3,4-bis(5-(methylthio)-1,3,4-oxadiazol-2-yl)butanoic Acid (26)

Compound 25 (82 mg, 0.22 mmol) was dissolved in DCM (2 mL), to which TFA (1 mL) was added. The reaction mixture was stirred at rt for 3 h, and then concentrated under reduced pressure to remove the solvent. The residue was purified by prep-RP-HPLC (method 6: 30%-60% B in 8 min→95% B in 4 min) to give compound 26 (21 mg).

LC-MS (method 1): R$_f$=1.46 min; m/z (ES$^+$)=316.9 (M+H)$^+$.

$^1$H NMR (500 MHz, CDCl$_3$) δ7.63 (br s, 1H), 3.99-3.96 (m, 1H), 3.47-3.34 (m, 2H), 3.08-2.90 (m, 2H), 2.68 (s, 3H), 2.67 (s, 3H).

Step 5: Synthesis of 3,4-bis(5-(methylsulfonyl)-1,3,4-oxadiazol-2-yl)butanoic Acid (1)

Compound 26 (21 mg, 0.066 mmol) was dissolved in DCM (2 mL), to which m-chloroperbenzoic acid (135 mg, 0.66 mmol) was added. The reaction mixture was stirred at rt for 16 h, and then concentrated under reduced pressure to remove the solvent. The residue was purified by prep-RP-HPLC (method 6: 30%-60% B in 8 min→95% B in 4 min) to give compound 1 (14 mg) as a white solid.

LC-MS (method 1): R$_f$=1.40 min; m/z (ES$^+$)=380.8 (M+H)$^+$.

$^1$H NMR (500 MHz, DMSO-d$_6$) δ12.66 (br s, 1H), 4.11-4.08 (m, 1H), 3.67-3.55 (m, 8H), 3.03-2.98 (m, 2H).

Example 2

Synthesis of 6-(2,3-bis(5-(methylsulfonyl)-1,3,4-oxadiazol-2-yl) propanamido)hexanoic Acid (Linker 2)

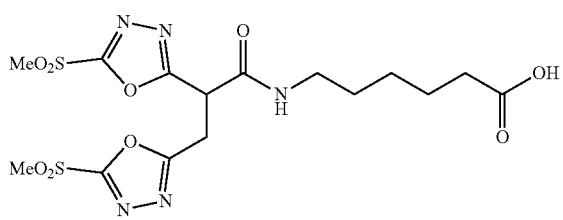

2

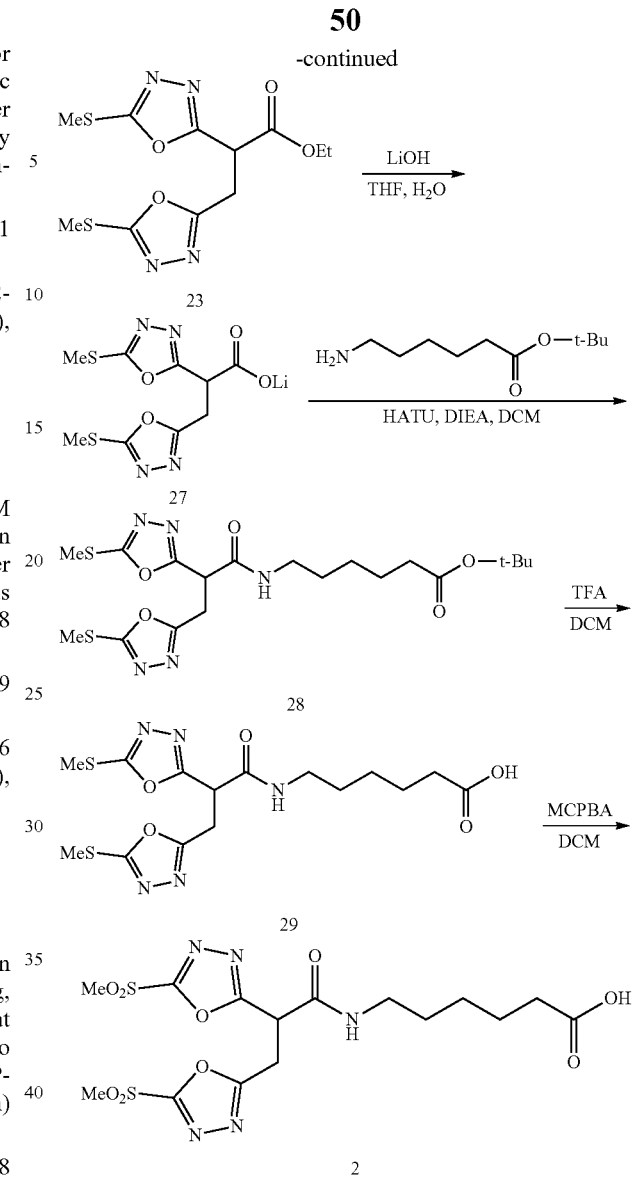

Step 1: Synthesis of Lithium 2,3-bis(5-(methylthio)-1,3,4-oxadiazol-2-yl)propanoate (27)

Compound 23 (83 mg, 0.25 mmol) was dissolved in THF (6 mL), to which aqueous lithium hydroxide solution (5.6 mL, 1.9 mg/mL, 0.44 mmol) was added. The reaction mixture was stirred at rt for 2 h, and then lyophilized to give crude product 27 (77 mg), which was used for next step without further purification.

Step 2: Synthesis of tert-butyl 6-(2,3-bis(5-(methylthio)-1,3,4-oxadiazol-2-yl) propanamido)hexanoate (28)

Compound 27 (77 mg), tert-butyl 6-aminohexanoate (94 mg, 0.50 mmol, prepared according to US2010/0261736) and HATU (190 mg, 0.50 mmol) were dissolved in DMF (3 mL), to which DIEA (88 µL, 0.50 mmol) was added. The reaction mixture was stirred at rt for 4 h, and then EA was added. The organic phase was washed with water, dried, filtered, and concentrated under reduced pressure sequentially. The residue was purified by silica gel chromatography (PE/EA 1:1) to give compound 28 (90 mg) as colorless oil.

LC-MS (method 1): R$_t$=1.88 min; m/z (ES$^+$)=472.1 (M+H)$^+$.

Step 3: Synthesis of 6-(2,3-bis(5-(methylthio)-1,3,4-oxadiazol-2-yl)propanamido) Hexanoic Acid (29)

Compound 28 (40 mg, 80 μmol) was dissolved in DCM (5 mL), to which TFA (2 mL) was added. The reaction mixture was stirred at rt for 2 h, and then concentrated under reduced pressure to remove the solvent. The residue was purified by silica gel chromatography (DCM/MeOH 20:1) to give compound 29 (15 mg) as a yellow solid.

LC-MS (method 1): R$_t$=1.51 min; m/z (ES$^+$)=416.1 (M+H)$^+$.

$^1$H NMR (500 MHz, CDCl$_3$) δ7.07 (br s, 1H), 4.53 (t, 1H), δ 3.75-3.72 (m, 1H), 3.56-3.52 (m, 1H), 3.33-3.21 (m, 2H), 2.70 (s, 3H), 2.68 (s, 3H), 2.35 (t, 2H), 1.66-1.60 (m, 2H), 1.55-1.50 (m, 2H), 1.38-1.25 (m, 2H).

Step 4: Synthesis of 6-(2,3-bis(5-(methylsulfonyl)-1,3,4-oxadiazol-2-yl)propanamido) Hexanoic Acid (2)

Compound 29 (10 mg, 25 μmol) was dissolved in DMF (5 mL), to which m-chloroperbenzoic acid (43 mg, 0.25 mmol) was added. The reaction mixture was stirred at rt overnight, and then concentrated under reduced pressure to remove the solvent. The residue was purified by prep-RP-HPLC (method 6: 20%-50% B in 8 min→95% B in 4 min) to give compound 2 (3.5 mg) as a white solid.

LC-MS (method 1): R$_t$=1.51 min; m/z (ES$^+$)=480.1 (M+H)$^+$.

$^1$H NMR (500 MHz, CDCl$_3$) δ 8.66 (t, 1H), 4.72 (t, 1H), 3.79-3.77 (m, 2H), 3.69 (s, 3H), 3.65 (s, 3H), 3.10-3.07 (m, 2H), 2.20-2.17 (m, 2H), 1.49-1.46 (m, 2H), 1.42-1.39 (m, 2H), 1.06-1.05 (m, 2H).

Example 3

Synthesis of 3-(5-(methylsulfonyl)-1,3,4-oxadiazol-2-yl)-2-((5-(methylsulfonyl)-1,3,4-oxadiazol-2-yl)methyl)propanoic Acid (Linker 3)

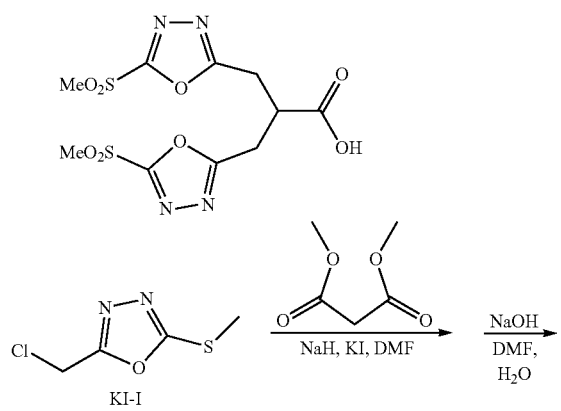

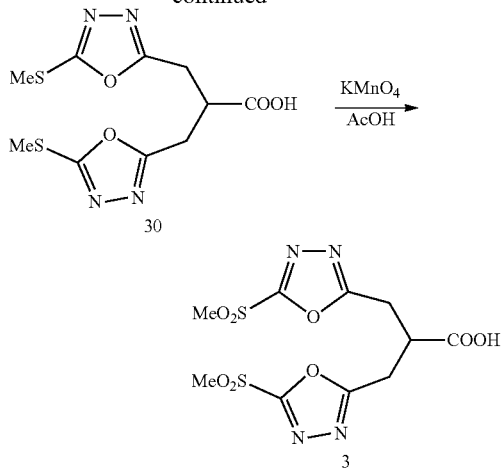

Step 1: Synthesis of 3-(5-(methylthio)-1,3,4-oxadiazol-2-yl)-2-((5-(methylthio)-1,3,4-oxadiazol-2-yl)methyl) Propanoic Acid (30)

Dimethyl malonate (81 mg, 0.61 mmol) was dissolved in THF (5 mL), to which sodium hydride (60% dispersion in mineral oil, 73 mg, 1.82 mmol) was added. The reaction mixture was stirred at rt for 30 min, followed by sequential addition of KI-1 (200 mg, 1.21 mmol) and potassium iodide (201 mg, 1.21 mmol). The reaction mixture was continuously stirred at rt for 1 h, and then aqueous sodium hydroxide solution (1.0 M, 2 mL, 2.0 mmol) was added, followed by continuous stirring at rt for 1 h. Concentrated hydrochloric acid was added to adjust the pH of the solution to 2~3, and then the mixture was extracted by EA. The organic phase was sequentially washed with brine, dried, filtered, and concentrated under reduced pressure. The residue was purified by prep-RP-HPLC (method 6: 40%-60% B in 8 min→95% B in 4 min) to give compound 30 (40 mg).

LC-MS (method 1): R$_t$=1.48 min; m/z (ES$^+$)=317.0 (M+H)$^+$.

$^1$H NMR (500 MHz, CDCl$_3$) δ 8.95 (br s, 1H), 3.54-3.51 (m, 1H), 3.40-3.36 (m, 2H), 3.25-3.20 (m, 2H), 2.68 (s, 6H).

Step 2: Synthesis of 3-(5-(methylsulfonyl)-1,3,4-oxadiazol-2-yl)-2-((5-(methylsulfonyl)-1,3,4-oxadiazol-2-yl)methyl)propanoic Acid (3)

Compound 30 (40 mg, 0.13 mmol) was dissolved in acetic acid (2 mL), to which potassium permanganate (50 mg, 0.32 mmol) was added. The reaction mixture was stirred at rt for 2 h, and then filtered to remove the solid. The filtrate was diluted by EA, and the organic phase was sequentially washed with water, dried, filtered, and concentrated under reduced pressure. The residue was purified by prep-RP-HPLC (method 6: 30%-60% B in 8 min→95% B in 4 min) to give compound 3 (12 mg) as a white solid.

LC-MS (method 1): R$_t$=1.42 min; m/z (ES$^+$)=381.0 (M+H)$^+$.

$^1$H NMR (500 MHz, DMSO-d$_6$) δ3.65 (s, 6H), 3.54-3.52 (m, 1H), 3.47-3.35 (m, 4H).

Example 4

Synthesis of 4-(5-(methylsulfonyl)-1,3,4-oxadiazol-2-yl)-2-((5-(methylsulfonyl)-1,3,4-oxadiazol-2-yl)methyl)butanoic Acid (Linker 4)

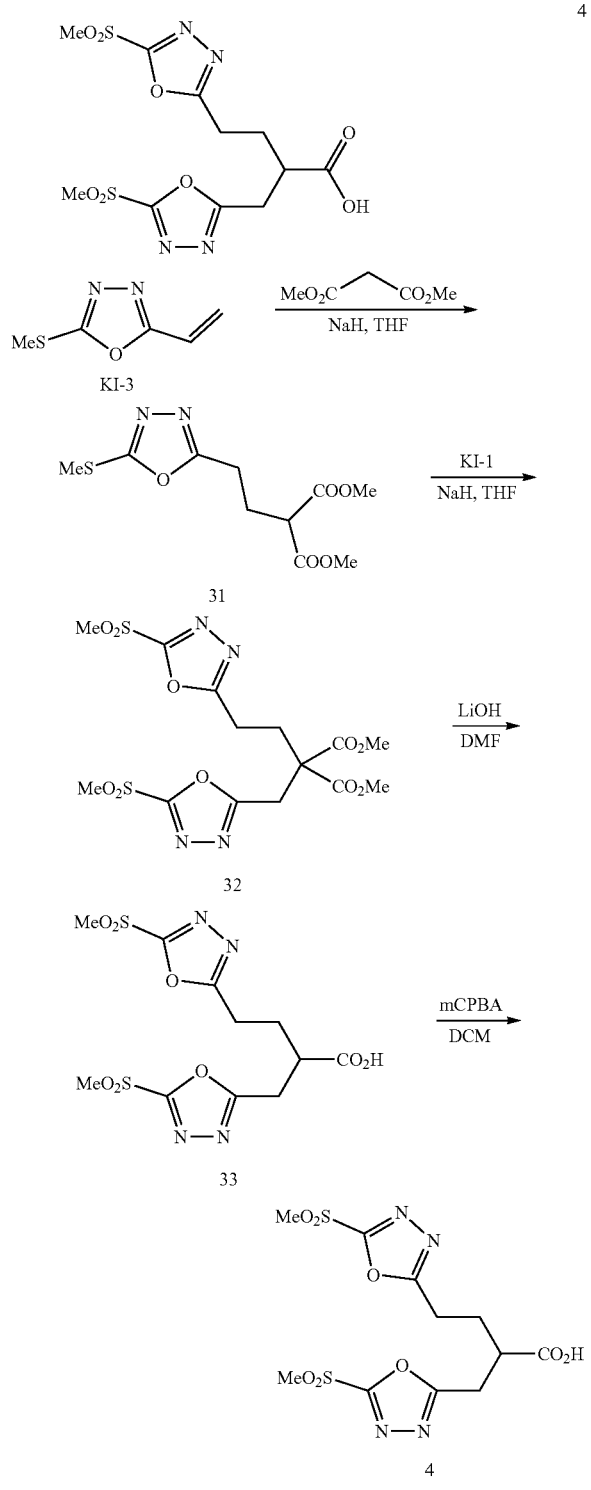

Step 1: Synthesis of dimethyl 2-(2-(5-(methylthio)-1,3,4-oxadiazol-2-yl)ethyl)malonate (31)

Dimethyl malonate (98 mg, 0.75 mmol) was dissolved in THF (5 mL), to which sodium hydride (60% dispersion in mineral oil, 50 mg, 1.25 mmol) was added. The reaction mixture was stirred at rt for 30 min, followed by the addition of KI-3 (177 mg, 1.25 mmol) and continuous stirring for 4 h. The mixture was concentrated under reduced pressure to remove the solvent, and the residue was purified by prep-RP-HPLC (method 6: 40%-70% B in 8 min→95% B in 4 min) to give compound 31 (90 mg) as colorless oil.

LC-MS (method 1): $R_t$=1.43 min; m/z (ES$^+$)=275.0 (M+H)$^+$.

$^1$H NMR (500 MHz, CDCl$_3$) δ3.76 (s, 6H), 3.56 (t, 1H), 2.93 (t, 2H), 2.71 (s, 3H), 2.39 (q, 2H).

Step 2: Synthesis of dimethyl 2-(2-(5-(methylthio)-1,3,4-oxadiazol-2-yl)ethyl)-2-((5-(methylthio)-1,3,4-oxadiazol-2-yl)methyl)malonate (32)

Compound 31 (90 mg, 0.33 mmol) was dissolved in THF (2 mL), to which sodium hydride (60% dispersion in mineral oil, 20 mg, 0.50 mmol) was added. The reaction mixture was stirred at rt for 30 min, followed by the addition of KI-1 (65 mg, 0.40 mmol) and continuous stirring for 3 h. The reaction mixture was concentrated under reduced pressure to remove the solvent, and the residue was purified by prep-RP-HPLC (method 6: 40%-70% B in 8 min→95% B in 4 min) to give compound 32 (25 mg) as colorless oil.

LC-MS (method 1): $R_t$=1.53 min; m/z (ES$^+$)=402.9 (M+H)$^+$.

$^1$H NMR (500 MHz, CDCl$_3$) δ3.77 (s, 6H), 3.53 (s, 2H), 2.91 (t, 2H), 2.68 (s, 6H), 2.43 (t, 2H).

Step 3: Synthesis of 4-(5-(methylthio)-1,3,4-oxadiazol-2-yl)-2-((5-(methylthio)-1,3,4-oxadiazol-2-yl)methyl) butanoic Acid (33)

Compound 32 (25 mg, 62 µmol) was dissolved in DMF (2 mL), to which aqueous lithium hydroxide (1 M, 0.62 mL, 0.62 mmol) was added. The reaction mixture was stirred at rt for 48 h, followed by the addition of concentrated hydrochloric acid to adjust pH to 2~3. The mixture was extracted by EA, and the organic phase was sequentially washed with water, dried, filtered, and concentrated under reduced pressure to give compound 33 (12 mg) as colorless oil.

LC-MS (method 1): $R_t$=1.34 min; m/z (ES$^+$)=330.9 (M+H)$^+$.

$^1$H NMR (500 MHz, CDCl$_3$) δ3.29-3.25 (m, 1H), 3.10-2.98 (m, 4H), 2.69 (s, 6H), 2.25-2.12 (m, 2H).

Step 4: 4-(5-(methylsulfonyl)-1,3,4-oxadiazol-2-yl)-2-((5-(methylsulfonyl)-1,3,4-oxadiazol-2-yl)methyl) butanoic Acid (4)

Compound 33 (12 mg, 36 µmol) was dissolved in DCM (3 mL), to which m-chloroperbenzoic acid (74 mg, 0.36 mmol) was added. The reaction mixture was stirred at rt for 16 h, and then concentrated under reduced pressure to remove the solvent. The residue was purified by prep-RP-HPLC (method 6: 40%-70% B in 8 min→95% B in 4 min) to give compound 4 (5 mg) as a white solid.

LC-MS (method 1): $R_t$=1.69 min; m/z (ES$^+$)=394.9 (M+H)$^+$.

$^1$H NMR (500 MHz, DMSO-d$_6$) δ3.65 (s, 3H), 3.63 (s, 3H), 3.38-3.26 (m, 2H), 3.15-3.07 (3H), 2.19-2.11 (m, 2H).

Example 5

Synthesis of 4-(5-(methylsulfonyl)-1,3,4-oxadiazol-2-yl)-2-(2-(5-(methylsulfonyl)-1,3,4-oxadiazol-2-yl)ethyl)butanoic Acid (Linker 5)

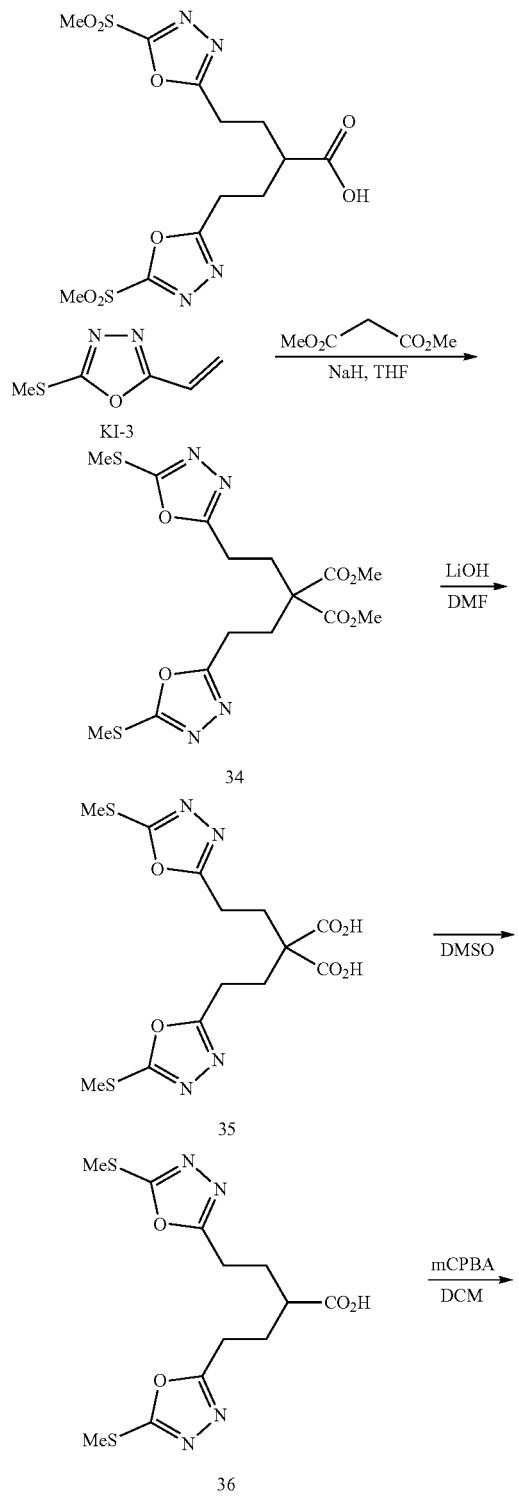

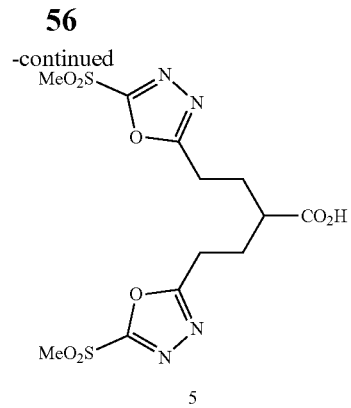

Step 1: Synthesis of dimethyl 2,2-bis(2-(5-(methylthio)-1,3,4-oxadiazol-2-yl)ethyl)malonate (34)

Dimethyl malonate (46 mg, 0.35 mmol) was dissolved in THF (5 mL), to which sodium hydride (60% dispersion in mineral oil, 42 mg, 1.05 mmol) was added. The reaction mixture was stirred at rt for 30 min, followed by the addition of KI-3 (100 mg, 0.70 mmol) and continuous stirring for 4 h. The mixture was concentrated under reduced pressure to remove the solvent, and the residue was purified by silica gel chromatography (PE/EA 1:1) to give compound 34 (46 mg) as colorless oil.

LC-MS (method 1): $R_t$=1.72 min; m/z (ES$^+$)=417.1 (M+H)$^+$.

$^1$H NMR (500 MHz, CDCl$_3$) δ3.72 (s, 6H), 2.82 (t, 4H), 2.66 (s, 6H), 2.38 (t, 4H).

Step 2: Synthesis of 2,2-bis(2-(5-(methylthio)-1,3,4-oxadiazol-2-yl)ethyl)malonic Acid (35)

Compound 34 (270 mg, 0.65 mmol) was dissolved in THF (5 mL), to which aqueous lithium hydroxide (2 M, 3.24 mL, 6.48 mmol) was added. The reaction mixture was stirred at rt for 16 h, to which 1 M hydrochloric acid was added to adjust pH to 2~3. The mixture was extracted by EA, and the organic phase was sequentially washed with water, dried, filtered, and concentrated under reduced pressure to give compound 35 (200 mg) as a white solid.

LC-MS (method 1): $R_t$=1.49 min; m/z (ES$^+$)=389.0 (M+H)$^+$.

$^1$H NMR (500 MHz, DMSO-d$_6$) δ13.25 (br s, 2H), 2.81 (t, 4H), 2.68 (s, 6H), 2.23 (t, 4H).

Step 3: Synthesis of 4-(5-(methylthio)-1,3,4-oxadiazol-2-yl)-2-(2-(5-(methylthio)-1,3,4-oxadiazol-2-yl)ethyl)butanoic Acid (36)

Compound 35 (100 mg, 0.26 mmol) was dissolved in DMSO (2 mL), and the reaction mixture was stirred at 100° C. for 2 h. Purification by prep-RP-HPLC (method 6: 30%-60% B in 8 min→95% B in 4 min) gave compound 36 (73 mg) as a white solid.

LC-MS (method 1): $R_t$=1.38 min; m/z (ES$^+$)=345.0 (M+H)$^+$.

$^1$H NMR (500 MHz, CDCl$_3$) δ8.90 (br s, 1H), 2.98-2.86 (m, 4H), 2.65-2.55 (m, 1H), 2.18-2.10 (m, 2H), 2.04-1.96 (m, 2H).

Step 4: Synthesis of 4-(5-(methylsulfonyl)-1,3,4-oxadiazol-2-yl)-2-(2-(5-(methylsulfonyl)-1,3,4-oxadiazol-2-yl)ethyl)butanoic Acid (5)

Compound 36 (40 mg, 0.12 mmol) was dissolved in DCM (5 mL), to which m-chloroperbenzoic acid (236 mg, 1.16 mmol) was added. The reaction mixture was stirred at rt for 16 h, and then concentrated under reduced pressure to remove the solvent. The residue was purified by prep-RP-HPLC (method 6: 30%-60% B in 8 min→95% B in 4 min) to give compound 5 (25 mg) as a white solid.

LC-MS (method 1): $R_t$=1.29 min; m/z (ES$^+$)=408.9 (M+H)$^+$.

$^1$H NMR (500 MHz, DMSO-d$_6$) δ3.64 (s, 6H), 3.04 (t, 4H), 2.62-2.58 (m, 1H), 2.10-1.98 (m, 4H).

Example 6

Synthesis of 5-(bis(2-(5-(methylsulfonyl)-1,3,4-oxadiazol-2-yl)ethyl)amino)-5-oxopentanoic Acid (Linker 6)

6

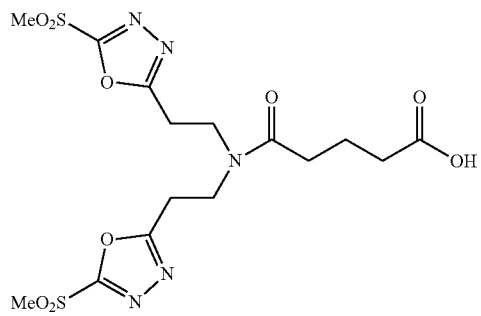

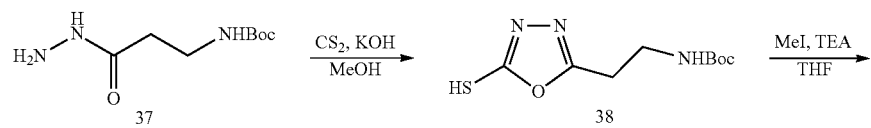

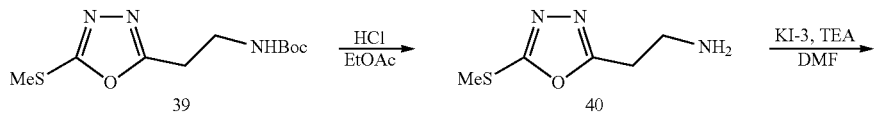

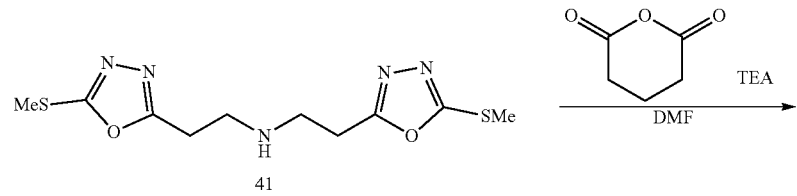

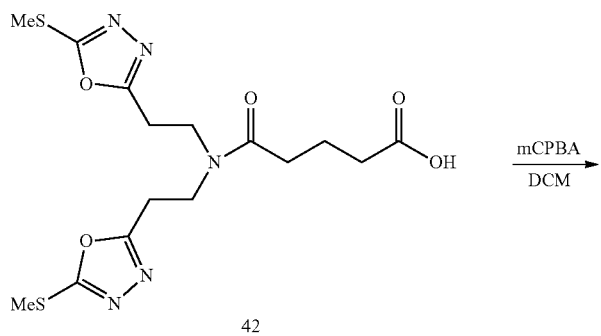

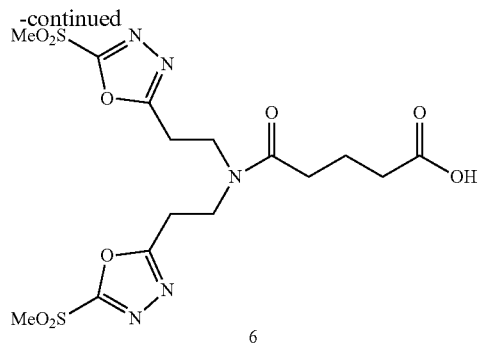

6

Step 1: Synthesis of tert-butyl 2-(5-mercapto-1,3,4-oxadiazol-2-yl)ethylcarbamate (38)

tert-Butyl 3-hydrazinyl-3-oxopropylcarbamate (37, 6.2 g, 31 mmol, prepared according to Journal of Medicinal Chemistry, 2008, 51, 4430-4448) was dissolved in MeOH (50 mL), to which carbon disulfide (5.5 mL, 92 mmol) and potassium hydroxide (4.7 g, 71 mmol) were sequentially added. The reaction mixture was stirred at rt for 1 h, and then heated to reflux for 4 h. After cooling down to rt, the mixture was diluted by water, to which concentrated hydrochloric acid was then added to adjust pH to 1~2. The mixture was extracted by EA, and the organic phase was sequentially dried, filtered, and concentrated under reduced pressure to give compound 38 as pale yellow oil, which was used for next step without further purification.

Step 2: Synthesis of tert-butyl 2-(5-(methylthio)-1,3,4-oxadiazol-2-yl)ethylcarbamate (39)

Compound 38 was dissolved in THF (30 mL), to which iodomethane (2.85 mL, 47.8 mmol) and TEA (6.38 mL, 47.8 mmol) were added. The reaction mixture was stirred at rt for 30 min, and then concentrated under reduced pressure to remove the solvent. The residue was purified by silica gel chromatography (PE/EA 3:1) to give compound 39 (2.4 g) as colorless oil.

LC-MS (method 2): $R_t$=1.64 min; m/z (ES$^+$)=260.0 (M+H)$^+$.

$^1$H NMR (500 MHz, CDCl$_3$) δ 5.08 (br s, 1H), 3.61-3.54 (m, 2H), 3.00 (t, 2H), 2.70 (s, 3H), 1.42 (s, 9H).

Step 3: Synthesis of 2-(5-(methylthio)-1,3,4-oxadiazol-2-yl)ethanamine (40)

Compound 39 (350 mg, 1.35 mmol) was dissolved in EA (5 mL), to which a solution of hydrogen chloride in EA (2.0 M, 5 mL, 10 mmol) was added. The reaction mixture was stirred at rt for 3 h, and then concentrated under reduced pressure to give compound 40 as a white solid, which was used for next step without further purification.

Step 4: Synthesis of bis(2-(5-(methylthio)-1,3,4-oxadiazol-2-yl)ethyl)amine (41)

Compound 40 was suspended in DMF (5 mL), to which KI-3 (192 mg, 1.35 mmol) and DIEA (0.47 mL, 2.7 mmol) were sequentially added. The reaction mixture was stirred at 80° C. for 16 h, and then concentrated under reduced pressure to remove the solvent. The residue was purified by prep-RP-HPLC (method 6: 30%-60% B in 8 min→95% B in 4 min) to give compound 41 (40 mg) as a white solid.

LC-MS (method 5): $R_t$=1.54 min; m/z (ES$^+$)=302.2 (M+H)$^+$.

$^1$H NMR (500 MHz, DMSO-d$_6$) δ2.96-2.91 (m, 4H), 2.91-2.87 (m, 4H), 2.68 (s, 6H).

Step 5: Synthesis of 5-(bis(2-(5-(methylthio)-1,3,4-oxadiazol-2-yl)ethyl)amino)-5-oxopentanoic Acid (42)

Compound 41 (40 mg, 0.13 mmol) was dissolved in DCM (5 mL), to which glutaric anhydride (30 mg, 0.26 mmol) and TEA (37 µL, 0.26 mmol) were sequentially added. The reaction mixture was stirred at rt for 3 h, and then concentrated under reduced pressure to remove the solvent. The residue was purified by prep-RP-HPLC (method 6: 40%-70% B in 8 min→95% B in 4 min) to give compound 42 (20 mg) as a white solid.

LC-MS (method 2): $R_t$=1.41 min; m/z (ES$^+$)=416.0 (M+H)$^+$.

$^1$H NMR (500 MHz, DMSO-d$_6$) δ 12.0 (br s, 1H), 3.71 (t, 2H), 3.61 (t, 2H), 3.16 (t, 2H), 3.04 (t, 2H), 2.68 (s, 3H), 2.67 (s, 3H), 2.26 (t, 2H), 2.19 (t, 2H), 1.68-1.62 (m, 2H).

Step 6: Synthesis of 5-(bis(2-(5-(methylsulfonyl)-1,3,4-oxadiazol-2-yl)ethyl)amino)-5-oxopentanoic Acid (6)

Compound 42 (20 mg, 48 µmol) was dissolved in DCM (5 mL), to which m-chloroperbenzoic acid (98 mg, 480 µmol) was added. The reaction mixture was stirred at rt for 16 h, and then concentrated under reduced pressure to remove the solvent. The residue was purified by prep-RP-HPLC (method 6: 30%-60% B in 8 min→95% B in 4 min) to give compound 6 (10 mg) as a white solid.

LC-MS (method 2): $R_t$=1.38 min; m/z (ES$^+$)=479.9 (M+H)$^+$.

$^1$H NMR (500 MHz, DMSO-d$_6$) δ3.84 (t, 2H), 3.70 (t, 2H), 3.65 (s, 3H), 3.61 (s, 3H), 3.34 (t, 2H), 3.22 (t, 2H), 2.31 (t, 2H), 2.19 (t, 2H), 1.67-1.61 (m, 2H).

Example 7

Synthesis of 4-(3,5-bis(5-(methylsulfonyl)-1,3,4-oxadiazol-2-yl)phenylamino)-4-oxobutanoic Acid (Linker 7)

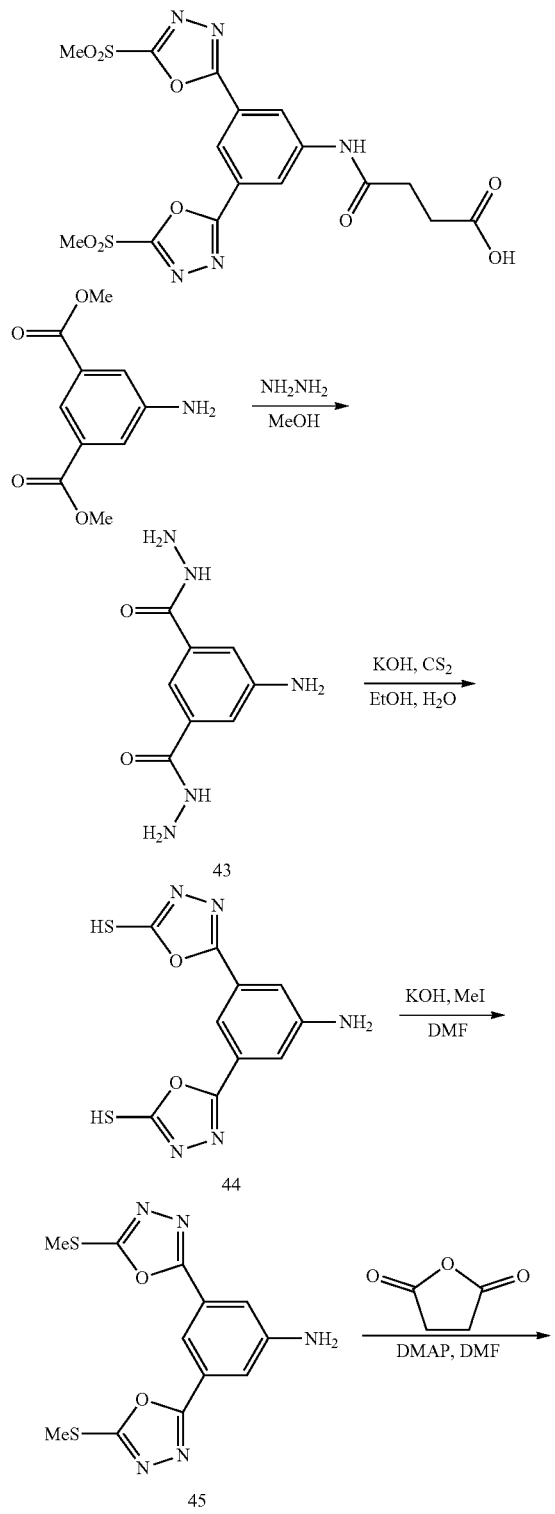

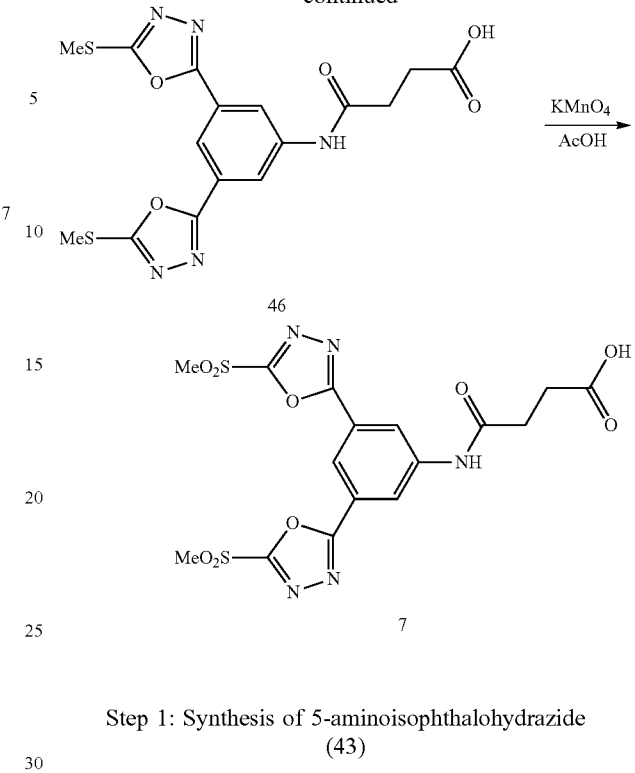

Step 1: Synthesis of 5-aminoisophthalohydrazide (43)

Dimethyl 5-aminoisophthalate (1.05 g, 5.0 mmol) and hydrazine monohydrate (1.25 g, 20 mmol) were dissolved in MeOH (10 mL), and the reaction mixture was heated to reflux for 24 h, while white precipitate formed in the meantime. The mixture was cooled to rt, and filtered to remove the solid. The filtrate was concentrated under reduced pressure to give compound 43 (600 mg) as a white solid, which was used for next step without further purification.

Step 2: Synthesis of 5,5'-(5-amino-1,3-phenylene)bis(1,3,4-oxadiazole-2-thiol) (44)

Compound 43 was suspended in ethanol (10 mL), to which carbon disulfide (1.04 mL, 17.2 mmol) and aqueous potassium hydroxide solution (2.3 M, 5 mL, 11.5 mmol) were sequentially added. The reaction mixture was heated to reflux for 16 h, and then cooled to rt, and diluted with water (50 mL). Concentrated hydrochloric acid was added to the solution to adjust pH to 1~2, while white precipitate formed. The solid was collected by filtration, washed, and dried to give compound 44 (300 mg) as a white solid, which was used for next step without further purification.

Step 3: Synthesis of 3,5-bis(5-(methylthio)-1,3,4-oxadiazol-2-yl)aniline (45)

Compound 44 (300 mg, 1.02 mmol) was dissolved in DMF (5 mL), to which potassium hydroxide (135 mg, 2.05 mmol) and iodomethane (191 μL, 3.07 mmol) were sequentially added. The reaction mixture was stirred at rt for 4 h. Water (10 mL) was added to the mixture, and solid was precipitated. The solid was collected by filtration, washed, and dried to give compound 45 (230 mg) as a white solid. LC-MS (method 1): $R_f$=1.71 min; m/z (ES$^+$)=322.0 (M+H)$^+$.

$^1$H NMR (500 MHz, DMSO-$d_6$) δ7.56 (s, 1H), 7.37 (d, 2H), 5.97 (s, 2H), 2.78 (s, 6H).

Step 4: Synthesis of 4-(3,5-bis(5-(methylthio)-1,3,4-oxadiazol-2-yl)phenylamino)-4-oxobutanoic Acid (46)

Compound 45 (35 mg, 0.11 mmol) was dissolved in DMF (2 mL), to which 4-dimethyaminopyridine (27 mg, 0.22 mmol) and succinic anhydride (33 mg, 0.33 mmol) were sequentially added. The reaction mixture was stirred at 80° C. for 24 h, and then concentrated to remove the solvent. The residue was purified by prep-RP-HPLC (method 6: 40%-70% B in 8 min→95% B in 4 min) to give compound 46 (8.0 mg) as a white solid.

LC-MS (method 3): $R_t$=1.09 min; m/z (ES$^+$)=422.0 (M+H)$^+$.

$^1$H NMR (500 MHz, DMSO-$d_6$) δ10.54 (s, 1H), 8.42 (d, 2H), 8.05 (s, 1H), 2.79 (s, 6H), 2.62 (t, 2H), 2.55 (t, 2H).

Step 5: Synthesis of 4-(3,5-bis(5-(methylsulfonyl)-1,3,4-oxadiazol-2-yl)phenylamino)-4-oxobutanoic acid (7)

Compound 46 (16 mg, 38 μmol) was dissolved in acetic acid (0.5 mL), to which potassium permanganate (15 mg, 95 μmol) was added. The reaction mixture was stirred at rt for 4 h, and then purified by prep-RP-HPLC (method 6: 40%-60% B in 8 min→95% B in 4 min) to give compound 7 (3.0 mg) as a white solid.

LC-MS (method 1): $R_t$=1.58 min; m/z (ES$^+$)=486.0 (M+H)$^+$.

$^1$H NMR (500 MHz, DMSO-$d_6$) δ10.71 (s, 1H), 8.65 (d, 2H), 8.33 (t, 1H), 3.73 (s, 6H), 2.65 (t, 2H), 2.57 (t, 2H).

Example 8

Synthesis of 3,4-bis((5-(methylsulfonyl)-1,3,4-oxadiazol-2-yl)methoxy)benzoic Acid (Linker 8)

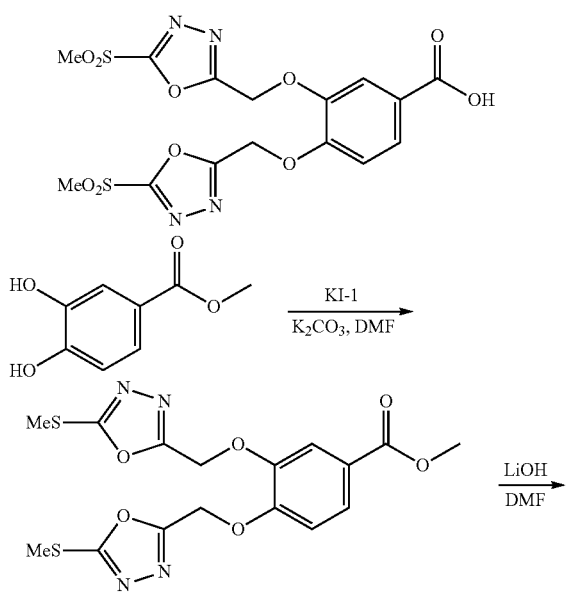

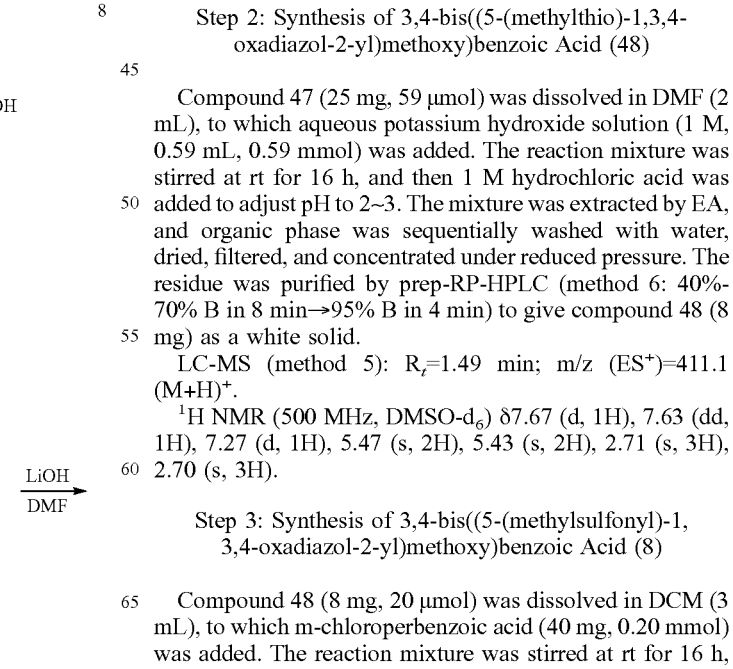

Step 1: Synthesis of methyl 3,4-bis((5-(methylthio)-1,3,4-oxadiazol-2-yl)methoxy)benzoate (47)

Methyl 3,4-dihydroxybenzoate (84 mg, 0.50 mmol) was dissolved in DMF (5 mL), to which potassium carbonate (173 mg, 1.25 mmol) and KI-1 (206 mg, 1.25 mmol) were sequentially added. The reaction mixture was stirred at 40° C. for 16 h, and then concentrated hydrochloric acid was added to adjust pH to 2~3. The mixture was diluted by EA, and then sequentially washed with water, dried, filtered, and concentrated under reduced pressure. The residue was purified by silica gel chromatography (PE/EA 1:1) to give compound 47 (125 mg) as a white solid.

LC-MS (method 2): $R_t$=1.72 min; m/z (ES$^+$)=424.8 (M+H)$^+$.

$^1$H NMR (500 MHz, CDCl$_3$) δ 7.75-7.71 (m, 2H), 7.11 (d, 1H), 5.32 (s, 2H), 5.28 (s, 2H), 3.89 (s, 3H), 2.73 (s, 3H), 2.72 (s, 3H).

Step 2: Synthesis of 3,4-bis((5-(methylthio)-1,3,4-oxadiazol-2-yl)methoxy)benzoic Acid (48)

Compound 47 (25 mg, 59 μmol) was dissolved in DMF (2 mL), to which aqueous potassium hydroxide solution (1 M, 0.59 mL, 0.59 mmol) was added. The reaction mixture was stirred at rt for 16 h, and then 1 M hydrochloric acid was added to adjust pH to 2~3. The mixture was extracted by EA, and organic phase was sequentially washed with water, dried, filtered, and concentrated under reduced pressure. The residue was purified by prep-RP-HPLC (method 6: 40%-70% B in 8 min→95% B in 4 min) to give compound 48 (8 mg) as a white solid.

LC-MS (method 5): $R_t$=1.49 min; m/z (ES$^+$)=411.1 (M+H)$^+$.

$^1$H NMR (500 MHz, DMSO-$d_6$) δ7.67 (d, 1H), 7.63 (dd, 1H), 7.27 (d, 1H), 5.47 (s, 2H), 5.43 (s, 2H), 2.71 (s, 3H), 2.70 (s, 3H).

Step 3: Synthesis of 3,4-bis((5-(methylsulfonyl)-1,3,4-oxadiazol-2-yl)methoxy)benzoic Acid (8)

Compound 48 (8 mg, 20 μmol) was dissolved in DCM (3 mL), to which m-chloroperbenzoic acid (40 mg, 0.20 mmol) was added. The reaction mixture was stirred at rt for 16 h, and then concentrated under reduced pressure to remove the solvent. The residue was purified by prep-RP-HPLC (method 6: 30%-60% B in 8 min→95% B in 4 min) to give compound 8 (3.3 mg) as a white solid.

LC-MS (method 2): $R_t$=1.52 min; m/z (ES$^+$)=474.8 (M+H)$^+$.

$^1$H NMR (500 MHz, DMSO-d$_6$) δ7.74 (d, 1H), 7.67 (dd, 1H), 7.34 (d, 1H), 5.68 (s, 2H), 5.64 (s, 2H), 3.70 (s, 3H), 3.69 (s, 3H).

Example 9

Synthesis of 3,5-bis((5-(methylsulfonyl)-1,3,4-oxadiazol-2-yl)methoxy)benzoic Acid (Linker 9)

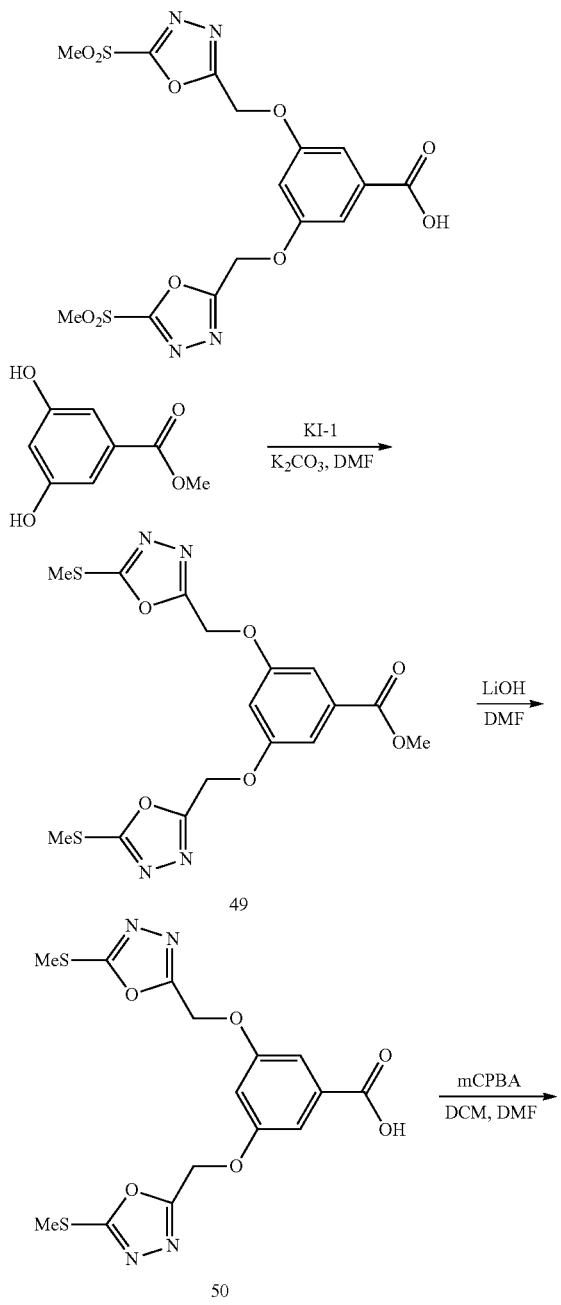

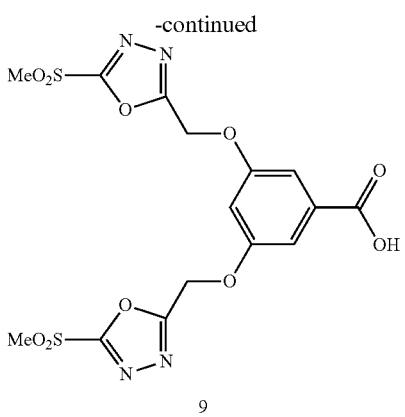

Step 1: Synthesis of methyl 3,5-bis((5-(methylthio)-1,3,4-oxadiazol-2-yl)methoxy)benzoate (49)

Methyl 3,5-dihydroxybenzoate (168 mg, 1.0 mmol) was dissolved in DMF (2 mL), to which potassium carbonate (414 mg, 3.0 mmol) and KI-1 (411 mg, 2.5 mmol) were sequentially added. The reaction mixture was stirred at 40° C. for 16 h, and then concentrated hydrochloric acid was added to adjust pH to 4~5. The mixture was diluted by EA, and then sequentially washed with brine, dried, filtered, and concentrated under reduced pressure. The residue was purified by silica gel chromatography (PE/EA 1:1) to give compound 49 (400 mg) as a white solid.

LC-MS (method 2): $R_t$=1.78 min; m/z (ES$^+$)=424.9 (M+H)$^+$.

$^1$H NMR (500 MHz, CDCl$_3$) δ7.35 (d, 2H), 6.87 (t, 1H), 5.24 (s, 4H), 3.92 (s, 3H), 2.74 (s, 6H).

Step 2: Synthesis of 3,5-bis((5-(methylthio)-1,3,4-oxadiazol-2-yl)methoxy)benzoic Acid (50)

Compound 49 (60 mg, 140 μmol) was dissolved in DMF (2 mL), to which aqueous lithium hydroxide (1.4 M, 0.5 mL, 0.70 mmol) was added. The reaction mixture was stirred at rt for 4 h, and then 1 M hydrochloric acid was added to adjust pH to 4~5. The mixture was extracted by EA, and the organic phase was sequentially washed with water, dried, filtered, and concentrated under reduced pressure. The residue was purified by prep-RP-HPLC (method 6: 30%-60% B in 8 min→95% B in 4 min) to give compound 50 (23 mg) as a white solid.

LC-MS (method 4): $R_t$=1.48 min; m/z (ES$^+$)=410.8 (M+H)$^+$.

$^1$H NMR (500 MHz, DMSO-d$_6$) δ7.25 (d, 2H), 7.04 (t, 1H), 5.45 (s, 4H), 2.72 (s, 6H).

Step 3: Synthesis of 3,5-bis((5-(methylsulfonyl)-1,3,4-oxadiazol-2-yl)methoxy)benzoic Acid (9)

Compound 50 (12 mg, 30 μmol) was dissolved in DCM/DMF (1.9 mL/0.1 mL), to which m-chloroperbenzoic acid (52 mg, 0.30 mmol) was added. The reaction mixture was stirred at rt for 16 h, and then concentrated under reduced pressure to remove the solvent. The residue was purified by prep-RP-HPLC (method 6: 40%-70% B in 8 min→95% B in 4 min) to give compound 9 (2.0 mg) as a white solid.

LC-MS (method 4): $R_t$=1.45 min; m/z (ES$^+$)=474.7 (M+H)$^+$.

$^1$H NMR (500 MHz, DMSO-d$_6$) δ7.31 (d, 2H), 7.14 (t, 1H), 5.64 (s, 4H), 3.70 (s, 6H).

Example 10

Synthesis of 6-(2,4,6-tris((5-(methylsulfonyl)-1,3,4-oxadiazol-2-yl)methoxy)benzamido)hexanoic Acid (Linker 10)

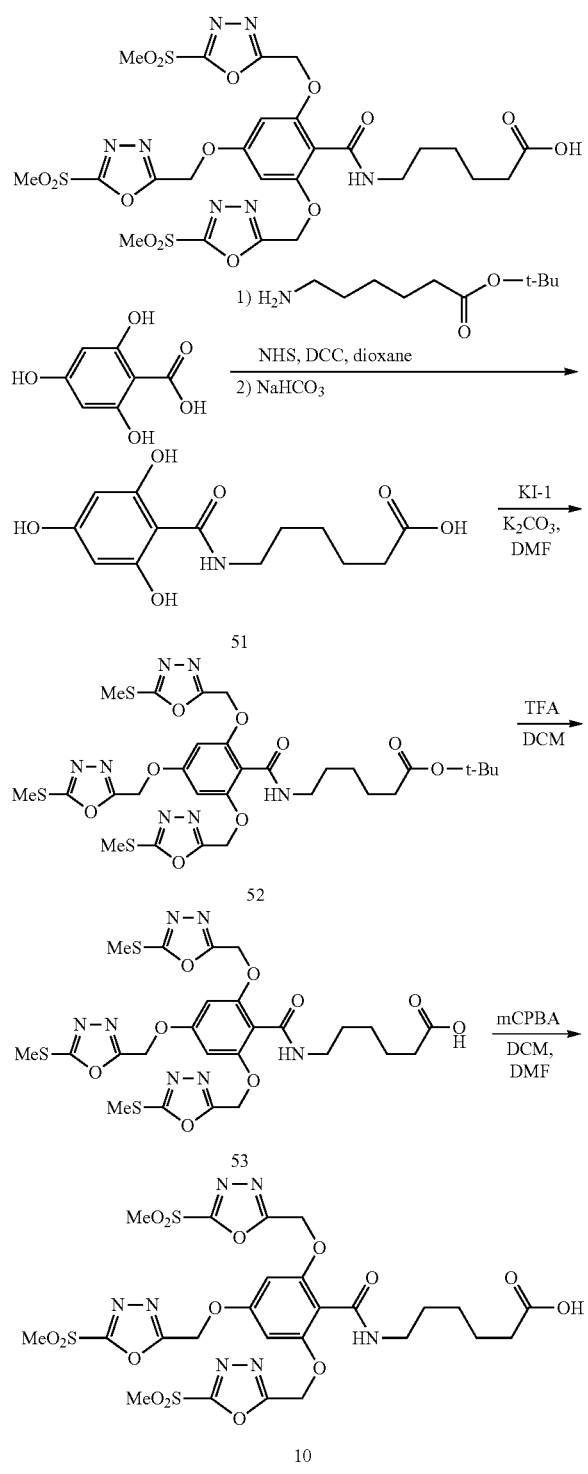

Step 1: Synthesis of tert-butyl 6-(2,4,6-trihydroxybenzamido)hexanoate (51)

2,4,6-Trihydroxybenzoic acid (85 mg, 0.50 mmol), N-hydroxysuccinimde (58 mg, 0.50 mmol), and N,N'-Dicyclohexylcarbodiimide (206 mg, 1.0 mmol) were dissolved in 1,4-dioxane (5 mL), and the reaction mixture was stirred at rt for 16 h. The mixture was filtered to remove the precipitate, and then tert-butyl 6-aminohexanoate (94 mg, 0.50 mmol) and aqueous sodium bicarbonate solution (42 mg in 2 mL of water, 0.50 mmol) were added to the filtrate. The reaction mixture was stirred at 50° C. for 1.5 h. After cooling to rt, concentrated hydrochloric acid was added to adjust pH to 4~5, and then the mixture was extracted by EA. The organic phase was sequentially washed with water, dried, filtered, and concentrated under reduced pressure. The residue was purified by silica gel chromatography (PE/EA 2:1) to give compound 51 (40 mg) as colorless oil.

LC-MS (method 2): $R_t$=1.77 min; m/z (ES$^+$)=340.0 (M+H)$^+$.

$^1$H NMR (500 MHz, CDCl$_3$) δ8.55 (br s, 1H), 5.93 (s, 2H), 3.29-3.28 (m, 2H), 2.19 (t, 2H), 1.57-1.53 (m, 4H), 1.40 (s, 9H), 1.32-1.24 (m, 2H).

Step 2: Synthesis of tert-butyl 6-(2,4,6-tris((5-(methylthio)-1,3,4-oxadiazol-2-yl)methoxy)benzamido)hexanoate (52)

Compound 51 (30 mg, 88 μmol) was dissolved in DMF (2 mL), to which KI-1 (51 mg, 308 μmol) and potassium carbonate (49 mg, 352 μmol) were sequentially added. The reaction mixture was stirred at rt for 16 h, and then diluted by EA. The mixture was sequentially washed with brine, dried, filtered, and concentrated under reduced pressure. The residue was purified by silica gel chromatography (PE/EA 1:1 to DCM/MeOH 20:1) to give compound 52 (50 mg) as a yellow solid.

LC-MS (method 3): $R_t$=1.38 min; m/z (ES$^+$)=724.0 (M+H)$^+$.

$^1$H NMR (500 MHz, CDCl$_3$) δ6.47 (s, 2H), 5.24 (s, 4H), 5.20 (s, 2H), 3.41-3.37 (m, 2H), 2.75 (s, 3H), 2.68 (s, 6H), 2.20 (t, 2H), 1.61-1.52 (m, 4H), 1.42 (s, 9H), 1.40-1.29 (m, 2H).

Step 3: Synthesis of 6-(2,4,6-tris((5-(methylthio)-1,3,4-oxadiazol-2-yl)methoxy)benzamido)hexanoic Acid (53)

Compound 52 (22 mg, 30 μmol) was dissolved in DCM (3 mL), to which TFA (0.3 mL) was added. The reaction mixture was stirred at rt for 3 h, and then concentrated under reduced pressure to remove the solvent. The residue was purified by silica gel chromatography (DCM/MeOH 20:1) to give compound 53 (14 mg) as yellow oil.

LC-MS (method 3): $R_t$=1.07 min; m/z (ES$^+$)=668.0 (M+H)$^+$.

$^1$H NMR (500 MHz, DMSO-d$_6$) δ8.01 (t, 1H), 6.68 (s, 2H), 5.43 (s, 2H), 5.34 (s, 4H), 3.08-3.06 (m, 2H), 2.73 (s, 3H), 2.70 (s, 6H), 2.15 (t, 2H), 1.46-1.43 (m, 4H), 1.34-1.32 (m, 2H).

Step 4: Synthesis of 6-(2,4,6-tris((5-(methylsulfonyl)-1,3,4-oxadiazol-2-yl)methoxy)benzamido) hexanoic Acid (10)

Compound 53 (14 mg, 20 μmol) was dissolved in DCM/DMF (1.9 mL/0.1 mL), to which m-chloroperbenzoic acid (104 mg, 600 µmol) was added. The reaction mixture was stirred at rt for 16 h, and then concentrated under reduced pressure to remove the solvent. The residue was purified by prep-RP-HPLC (method 6: 40%-70% B in 8 min→95% B in 4 min) to give compound 10 (1.5 mg) as a white solid.

LC-MS (method 2): R$_t$=1.56 min; m/z (ES$^+$)=763.8 (M+H)$^+$.

$^1$H NMR (500 MHz, DMSO-d$_6$) δ8.02 (t, 1H), 6.81 (s, 2H), 5.61 (s, 2H), 5.54 (s, 4H), 3.71 (s, 3H), 3.67 (s, 6H), 3.10-3.05 (m, 2H), 2.20 (t, 2H), 1.46-1.43 (m, 4H), 1.34-1.32 (m, 2H).

Example 11

Synthesis of 3,5-bis((3,4-bis(5-(methylsulfonyl)-1,3,4-oxadiazol-2-yl)butanamido)methyl)benzoic Acid (Linker 11)

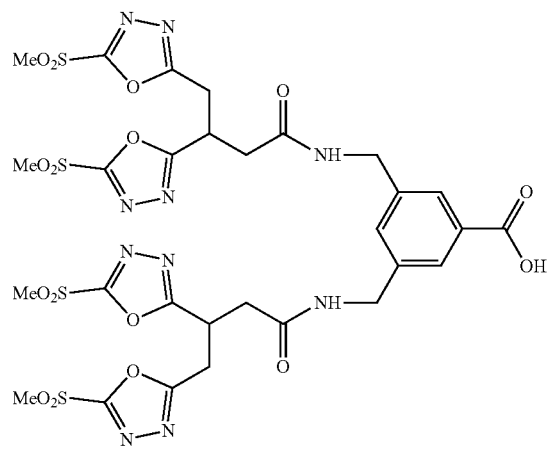

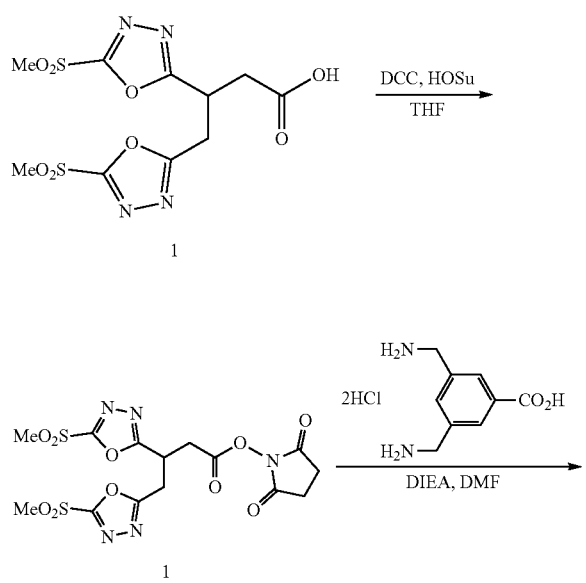

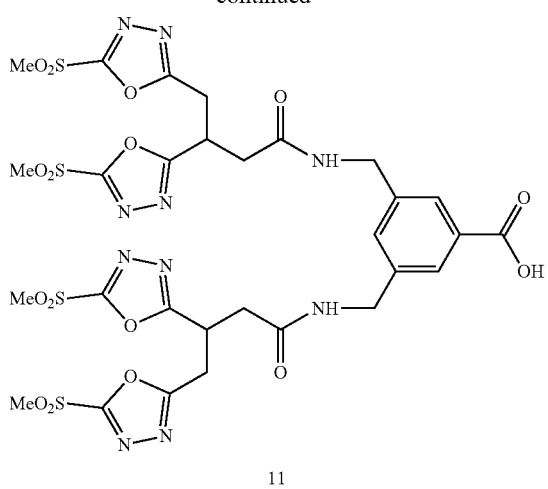

Step 1: Synthesis of 2,5-dioxopyrrolidin-1-yl 3,4-bis(5-(methylsulfonyl)-1,3,4-oxadiazol-2-yl)butanoate (54)

Compound 1 (70 mg, 0.184 mmol) and N-hydroxysuccinimide (25 mg, 0.217 mmol) were dissolved in THF (5 mL), to which DCC (50 mg, 0.243 mmol) was added. The reaction mixture was stirred at rt for 16 h, and then filtered to remove the solid. The filtrate was concentrated under reduced pressure, and the residue was purified by prep-RP-HPLC (method 6: 30%-60% B in 8 min→95% B in 4 min) to give compound 54 (45 mg) as a white solid.

LC-MS (method 2): R$_t$=1.51 min; m/z (ES$^+$)=477.5 (M+H)$^+$.

Step 2: Synthesis of 3,5-bis((3,4-bis(5-(methylsulfonyl)-1,3,4-oxadiazol-2-yl)butanamido)methyl)benzoic Acid (11)

Compound 54 (22 mg, 0.046 mmol) and 3,5-bis(aminomethyl)benzoic acid dihydrochloride (5 mg, 0.02 mmol) were dissolved in DMF (1 mL), to which DIEA (10 mg, 0.078 mmol) was added. The reaction mixture was stirred at rt for 4 h, and then concentrated under reduced pressure. The residue was purified by prep-RP-HPLC (method 6: 40%-60% B in 8 min→95% B in 4 min) to give compound 11 (5 mg) as a white solid.

LC-MS (method 2): R$_t$=1.60 min; m/z (ES$^+$)=904.1 (M+H)$^+$.

$^1$H NMR (500 MHz, DMSO-d$_6$) δ8.69 (t, 2H), 7.70 (s, 2H), 7.36 (s, 1H), 4.29 (d, 4H), 4.20-4.15 (m, 2H), 3.63 (s, 12H), 3.66-3.54 (m, 4H), 3.00-2.88 (m, 4H).

Example 12

Synthesis of 5-(bis(2-(3,4-bis(5-(methylsulfonyl)-1,3,4-oxadiazol-2-yl)butanamido)ethyl)amino)-5-oxo-pentanoic Acid (Linker 12)

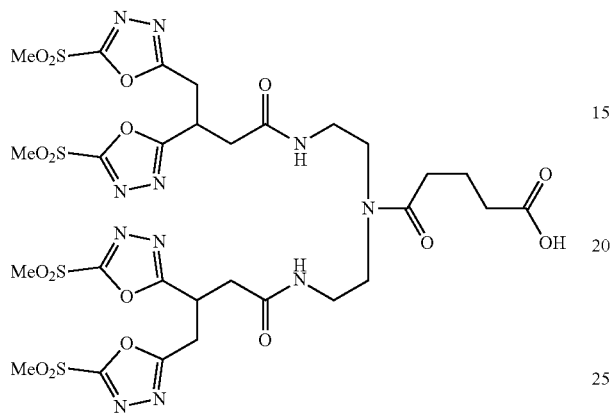

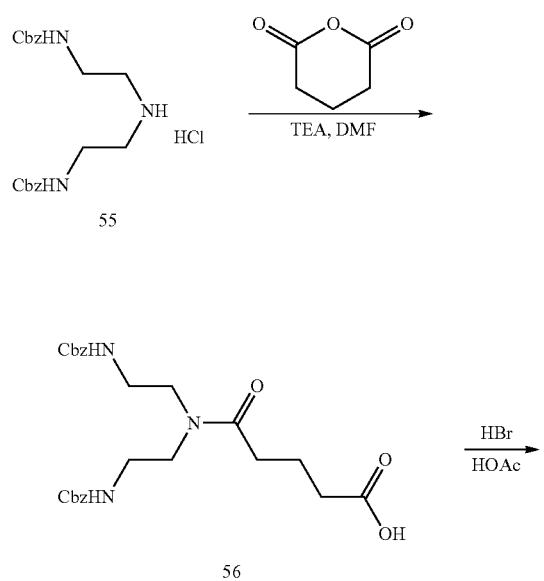

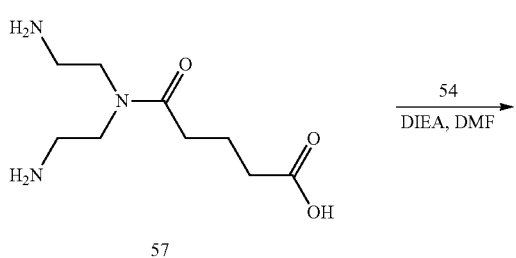

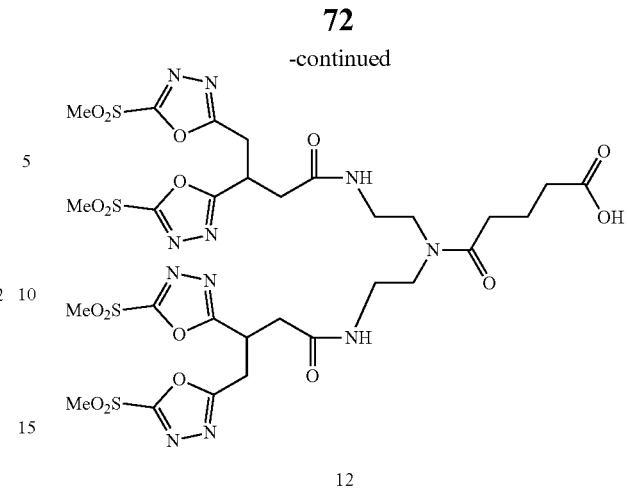

12

Step 1: Synthesis of 5-(bis(2-(benzyloxycarbonylamino)ethyl)amino)-5-oxopentanoic Acid (56)

Bis(2-(benzyloxycarbonylamino)ethyl)amine (55, 815 mg, 2 mmol, prepared according to European Journal of Medicinal Chemistry, 2009, 44, 678-688) and TEA (0.70 mL<5 mmol) were dissolved in DMF (5 mL), to which a solution of glutaric anhydride (228 mg, 2 mmol) in DMF (1 mL) was added. The reaction mixture was stirred at rt overnight, to which water (20 mL) was added and the mixture was extracted by DCM (15 mL×3). The combined organic phase was sequentially washed with brine, dried, filtered, and concentrated under reduced pressure. The residue was purified by silica gel chromatography (DCM/MeOH 30:1) to give compound 56 (872 mg) as a pale yellow solid.

LC-MS (method 3): Rt=1.21 min; m/z (ES+) 486.3 (M+H)$^+$.

Step 2: Synthesis of 5-(bis(2-aminoethyl)amino)-5-oxopentanoic acid (57)

A solution of hydrogen bromide in acetic acid (33%, 3 mL) was dropwise added to compound 56 (522 mg, 1.1 mmol), and then the reaction mixture was stirred at rt for 15 min. Diethyl ether (20 mL) was added to the mixture to precipitate a yellow solid, which was collected by centrifugation. Diethyl ether was added to the solid thus obtained, and the mixture was centrifuged again to collect the solid. The similar procedure was repeated for three times, and the solid was dried in vacuo (60° C.) to give compound 57 hydrobromide salt (350 mg) as a yellow solid.

LC-MS (method 4): Rt=0.28 min; m/z (ES$^+$) 218.0 (M+H)$^+$.

Step 3: Synthesis of 5-(bis(2-(3,4-bis(5-(methylsulfonyl)-1,3,4-oxadiazol-2-yl)butanamido)ethyl)amino)-5-oxopentanoic Acid (12)

Compound 57 hydrobromide salt (5 mg, 18.5 μmol) and compound 54 (22 mg, 46 μmol) were dissolved in DMF (1 mL), to which DIEA (10 mg, 78 μmol) was added. The reaction mixture was stirred at rt for 4 h, and then concentrated under reduced pressure. The residue was purified by prep-RP-HPLC (method 6: 40%-60% B in 8 min→95% B in 4 min) to give compound 12 (5 mg) as a white solid.

LC-MS (method 1): Rt=1.55 min; m/z (ES+) 941.2 (M+H)$^+$.

$^1$H NMR (500 MHz, DMSO-d$_6$) δ 8.27 (t, 1H), 8.17 (t, 1H), 4.17-4.09 (m, 2H), 3.64 (s, 6H), 3.63 (s, 6H), 3.62-3.52 (m, 4H), 3.29-3.22 (m, 4H), 3.20-3.08 (m, 4H), 2.91-2.76 (m, 4H), 2.30 (t, 2H), 2.23 (t, 2H), 1.73-1.65 (m, 2H).

Example 13

Synthesis of Oxadiazole Linker-Drug (1-vcMMAE)

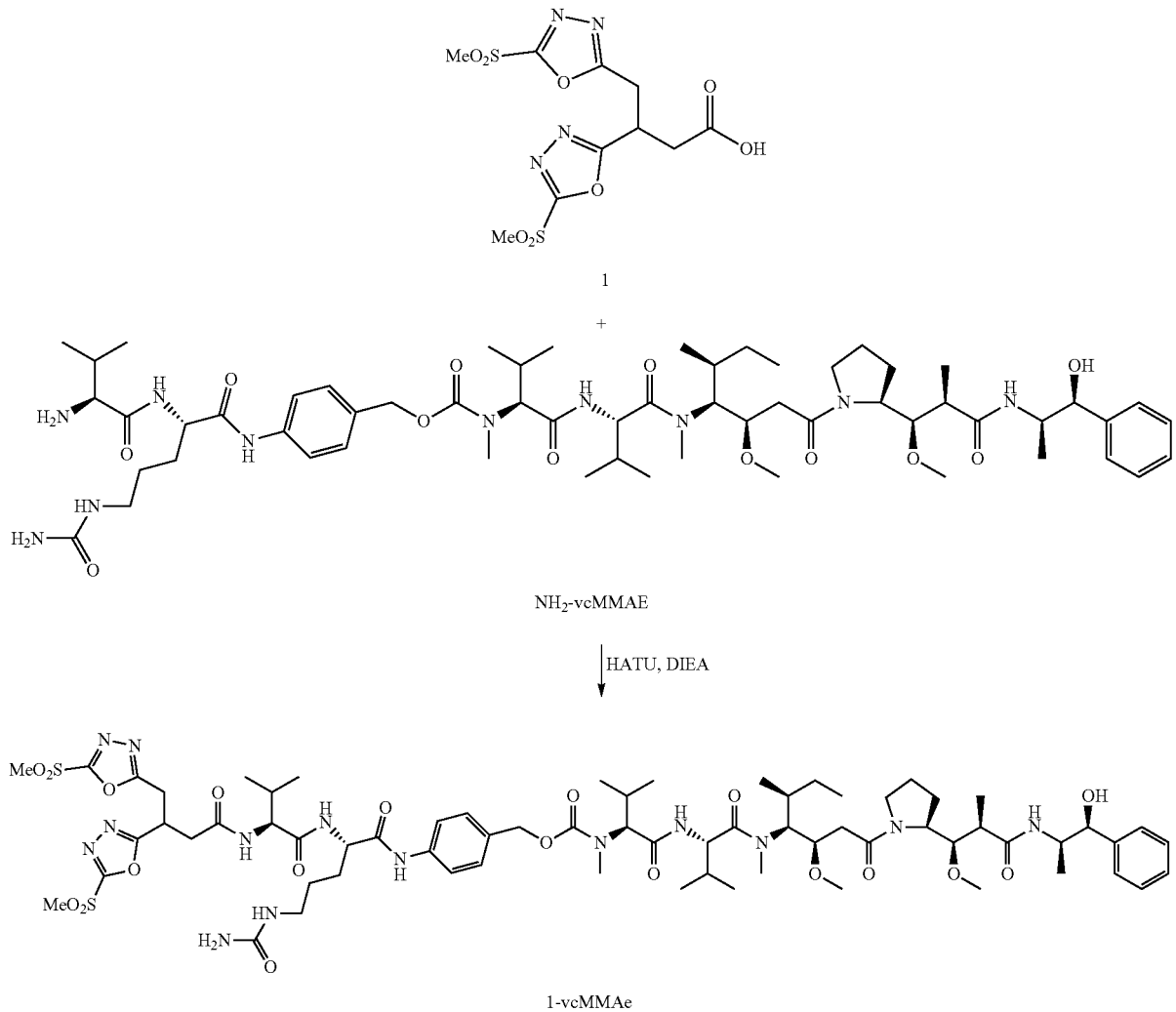

Compound 1 (5.0 mg, 13.15 μmol) and NH-vcMMAEF (TFA salt, 6.0 mg, 4.85 μmol, prepared according to WO2013/173337) were dissolved in DMF (0.2 mL), to which DIEA (3.39 μL, 19.4 μmol) and HATU (3.7 mg, 9.7 μmol) were then sequentially added. The reaction mixture was stirred at rt for 2 h, and then purified by prep-RP-HPLC (method 6: 40%-70% B in 8 min→95% B in 4 min) to give compound 1-vcMMAE (3.0 mg) as white powder.

LC-MS (method 1): $R_t$=1.84 min; m/z (ES$^+$) 743.1 [½(M+2H)]+.

Example 14

Synthesis of Other Oxadiazole Linker-Drugs

Other oxadiazole linker-drugs were synthesized via the similar method as that for 1-vcMMAE in example 13, except that compound 1 was replaced with oxadiazole linkers 2-12. The linker-drugs and their characterization data were listed in Table 1, wherein the linker-drug 2-vcMMAE to 12-vcMMAE were named according to the oxadiazole linker compounds 2 to 12.

TABLE 1

Linker-drugs of the invention and their characterizations

| Compound | LC-MS method; $R_t$ (min); m/z ½[M + 2H]$^+$ |
|---|---|
| 2-vcMMAE | 1; 1.84; 792.7 |
| 3-vcMMAE | 1; 1.87; 743.5 |
| 4-vcMMAE | 1; 1.89; 750.3 |
| 5-vcMMAE | 1; 1.83; 757.2 |
| 6-vcMMAE | 1; 1.85; 792.8 |
| 7-vcMMAE | 1; 1.86; 795.8 |
| 8-vcMMAE | 1; 1.91; 790.2 |
| 9-vcMMAE | 1; 1.91; 790.3 |
| 10-vcMMAE | 1; 1.89; 934.8 |
| 11-vcMMAE | 1; 1.88; 1004.5 |
| 12-vcMMAE | 1; 1.85; 1023.2 |

Example 15

Preparation and Characterization of Antibody-Drug Conjugates

Tris(2-carboxyethyl)phosphine (TCEP, 10 eq, stock solution 10 mM) was added to a solution of antibody H (IgG1) (2-10 mg/mL, containing 25 mM boric acid-sodium borate buffer, 25 mM NaCl and 1 mM diethylene triamine pentacetic acid (DTPA), pH 7.0-8.0). The reaction mixture was incubated at 37° C. in a shaker for 2 h, and then cooled to ~10° C., followed by buffer-exchange with a PBS buffer (100 mM $KH_2PO_4$—$K_2HPO_4$, 100 mM NaCl, 1 mM DTPA, pH 7.0-8.0) via ultrafiltration (Merck Millipore Amicon® Ultra, 50000 MWCO) or gel-filtration. The solution was cooled at 10° C., to which DMSO and compound 1-vcMMAE prepared in example 13 (stock solution in DMSO, 6 equivalent) were sequentially added, in which the volume percentage of DMSO was controlled at 15%. The conjugation reaction was conducted at 10° C. for 0.5 h.

Excess cysteine solution was added to the reaction mixture to quench the unreacted compound 1-vcMMAE, and the quenching reaction was kept at 10° C. for 30 min. The reaction mixture was ultrafiltered (Merck Millipore Amicon® Ultra, 50000 MWCO) or gel-filtered to remove excess 1-vcMMAE-cysteine adducts and excess cysteine. The filtrate was sterile filtered through 0.22 m filter (Merck Millex-GV Filter), and the solution of conjugate H-1-vcMMAE thus obtained was kept at 4° C.

Conjugates H-2-vcMMAE to H-12-vcMMAE were prepared from antibody H according to the same method as above, except for replacing compound 1-vcMMAE with compounds 2-vcMMAE to 12-vcMMAE.

1) Determination of Average DAR

The average DAR was calculated by from the relative peak area (%) of each peak and the corresponding number of drugs loaded on HIC (hydrophobic interaction chromatography) (Anal. Chem. 2013, 85, 1699-1704). The weighted peak percentage, which measures the contribution of individual drugloaded species to DAR, is calculated by multiplying the relative peak area (%) and the corresponding number of loaded drugs. DAR is then obtained by summing up the weighted peak percentage from all observed species and dividing the sum by 100, as follows:

DARt=Σ(relative peak area %×corresponding number of loaded drugs)/100

The average DARs of the ADCs of the invention were listed in table 2.

TABLE 2

The average DAR results of the ADCs in the invention

| ADC | Average DAR | Eq of linker-drug |
|---|---|---|
| H-1-vcMMAE | 4.0 | 6 |
| H-2-vcMMAE | 4.0 | 6 |
| H-3-vcMMAE | 4.0 | 8 |
| H-4-vcMMAE | 4.0 | 6 |
| H-5-vcMMAE | 4.0 | 6 |
| H-6-vcMMAE | 4.1 | 8 |
| H-7-vcMMAE | 4.1 | 6 |
| H-8-vcMMAE | 4.2 | 8 |
| H-9-vcMMAE | 4.1 | 8 |
| H-10-vcMMAE | 3.0 | 20 |
| H-11-vcMMAE | 2.1 | 4 |
| H-12-vcMMAE | 2.2 | 4 |

As shown in table 2, the average DARs of the ADCs (H-1-vcMMAE to H-9-vcMMAE) based on bis(1,3,4-oxadiazole) linker of the invention could be well-controlled around 4, and the DAR of the main component (85%+) is 4. The average DAR of the ADC (H-10-vcMMAE) based on tri(1,3,4-oxadiazole) linker of the invention could be well-controlled around 3, and the DAR of the main component (85%+) is 3. The average DARs of the ADCs (H-11-vcMMAE to H-12-vcMMAE) based on tetra(1,3,4-oxadiazole) linker of the invention could be well-controlled around 2, and the DAR of the main component (85%+) is 2. These results are due to the accurate site and number control by the site-specific linkers of the invention.

2) Native MS

8 μL of PNGase F (New England Biolabs, USA) was added to 400 μg of conjugate H-1-vcMMAE, and the mixture was incubated at 37° C. overnight (15 h). The deglycosylated ADC sample was buffer-exchanged into ammonium acetate buffer (20 mM, pH 7.0), and the buffer exchange procedure was repeated for 5 times.

The mass spectrometer used was high-resolution Orbitrap Exactive Plus EMR (Thermo Fisher Scientific, Germany), and the ion source is TriVersa NanoMate® (Advion, USA). The sample concentration was adjusted to 2 μg/μL, and direct injection was adopted. The mass data was collected under the positive ion mode, and the native mass data was analyzed by Protein Deconvolution 4.0 software (Thermo Fisher Scientific, Germany).

The native MS spectrum of antibody-drug conjugate H-1-vcMMAE was shown in FIG. 1, which shows that the main component of the product has a DAR of 4.

3) SDS-PAGE

SDS-PAGE was measured using NuPAGE™, 4-12%, Bis-Tris Gel (Thermal Fisher) on XCell SureLock® Mini-Cell protein electrophoresis instrument (Thermal Fisher). A sample (≥10 μg by weight) was combined with loading buffer, and the mixture was heated at 70° C. in water bath for 10 min. The sample and standard protein (5 μL/hole) were added to the spacer gel comb holes sequentially, and the electrophoresis was conducted at 220 V for 50 min. The gel was removed, rinsed by deionized water, and then stained in SimplyBlue™ SafeStain (Thermal Fisher) on a shaker for 3 h. The stained gel was rinsed by deionized water for three times, and destained on a shaker for 4 h. The destained gel was transferred to an imager to record the gel image.

Figure 2A:
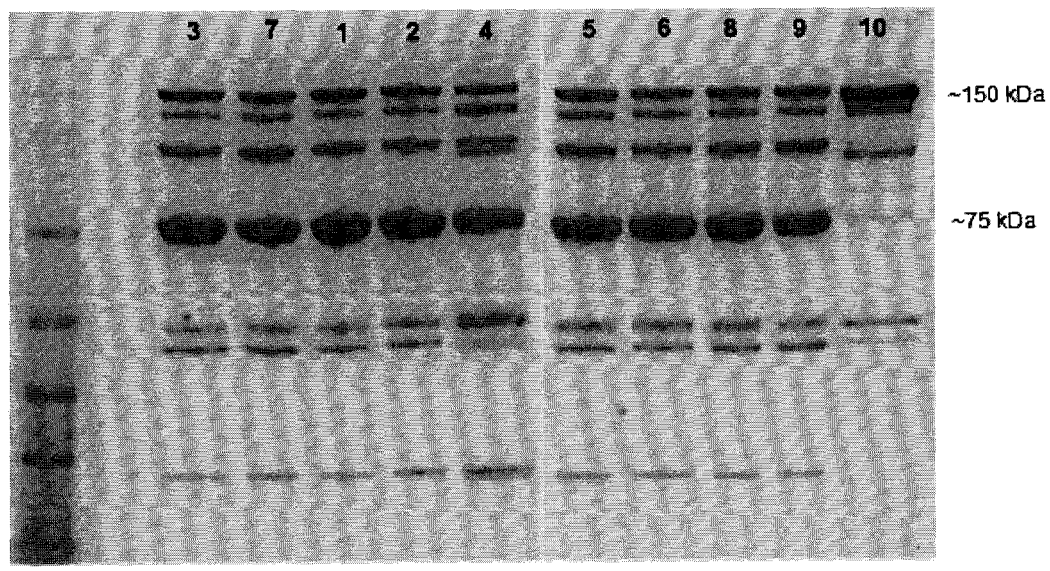
FIGS. 2a-2b illustrate the SDS-PAGE results of the antibody-drug conjugates based on oxadiazole linkers, wherein 2a represents the SDS-PAGE result of H-1-vcM-MAE to H-10-vcMMAE (corresponding to 1-10 respectively); 2b represents the SDS-PAGE result of H-11-vcM-MAE to H-12-vcMMAE (corresponding to 11-12 respectively).
Figure 2B:
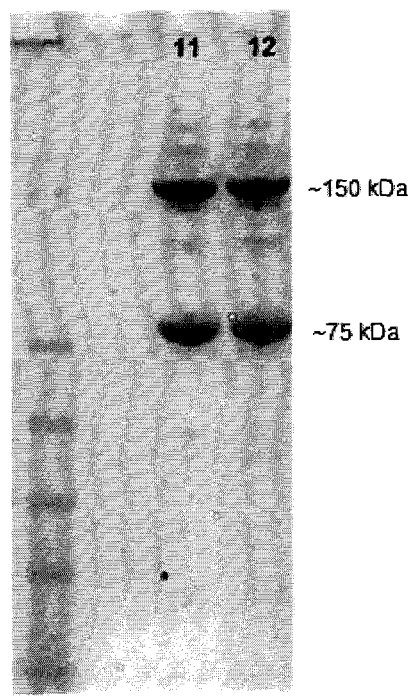
Figure 3A:
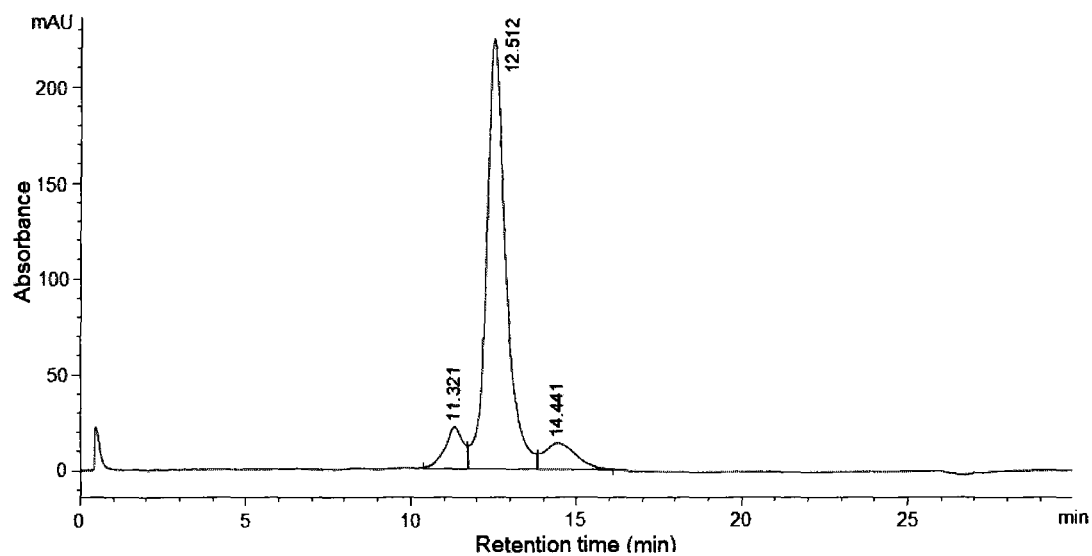
FIGS. 3a-3l illustrate the HIC results of the antibody-drug conjugates, wherein 3a-3l correspond to H-1-vcMMAE to H-12-vcMMAE, respectively.
Figure 3B:
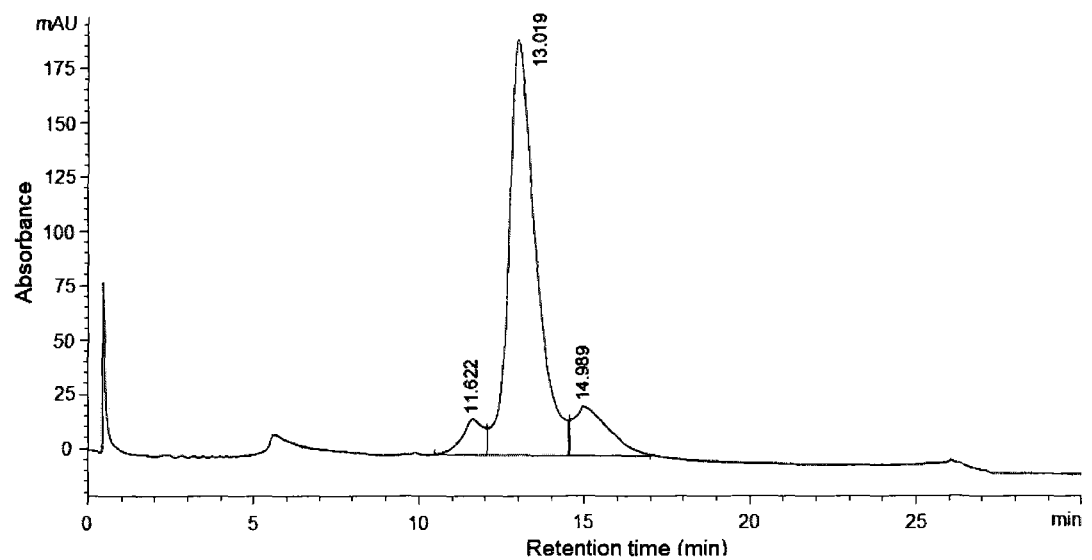
Figure 3C:
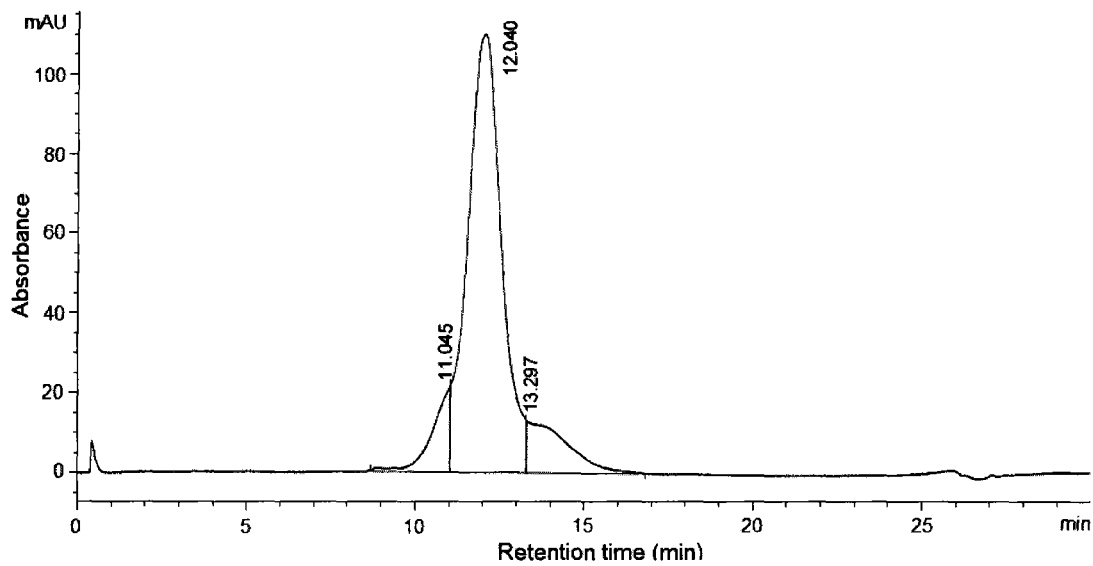
Figure 3D:
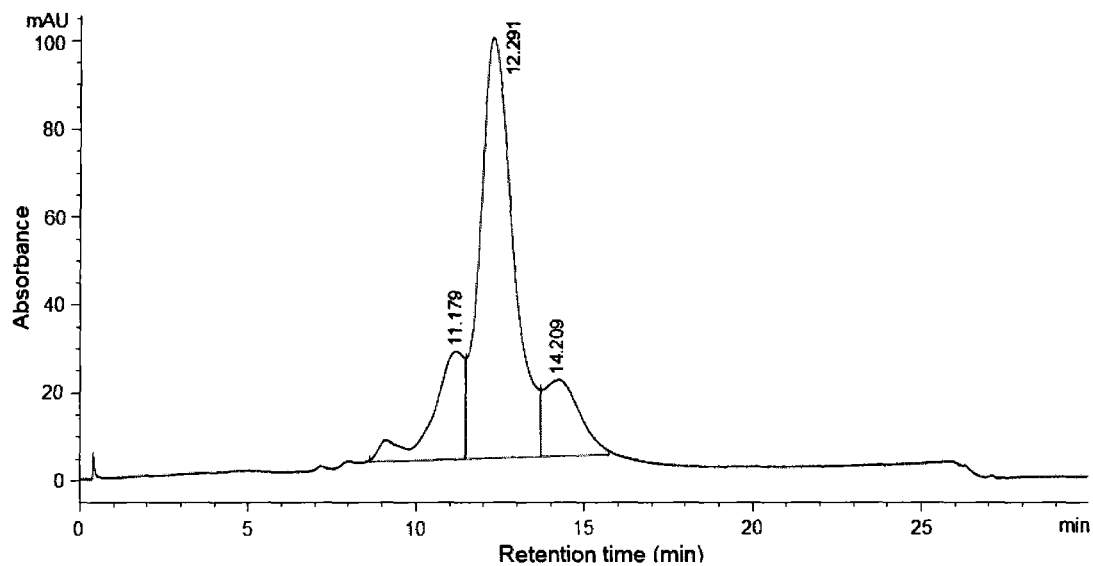
Figure 3E:
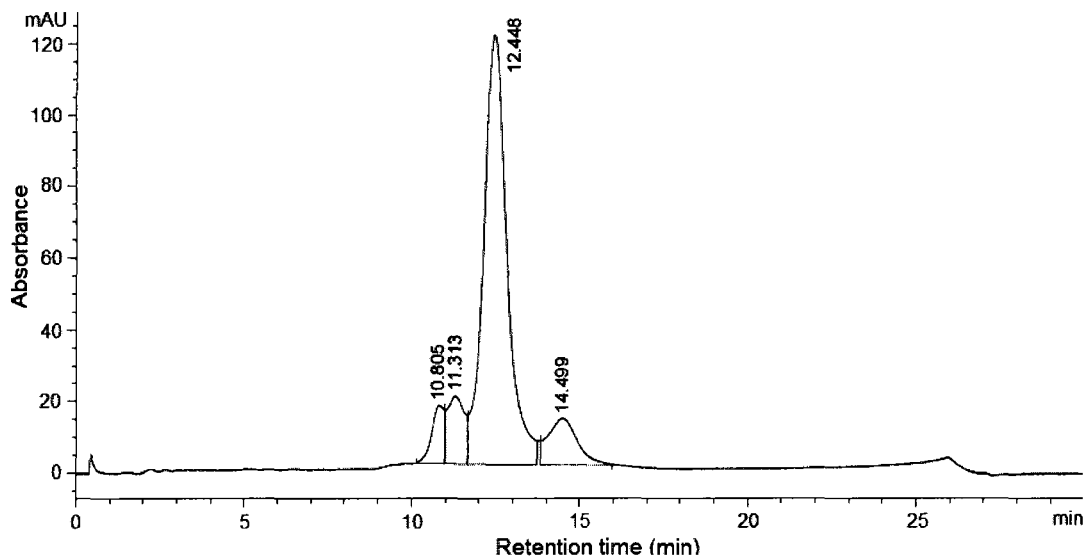
Figure 3F:
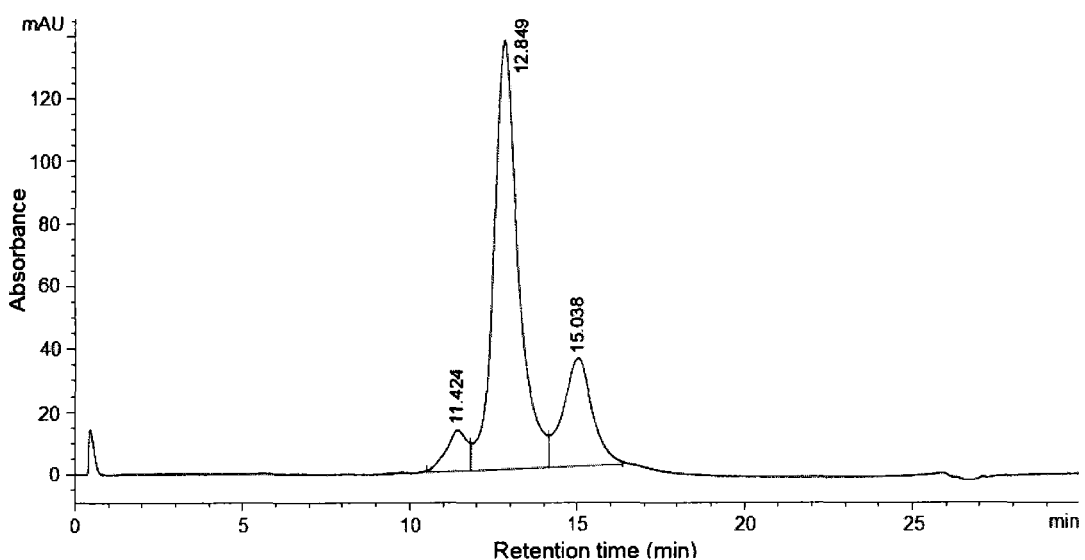
Figure 3G:
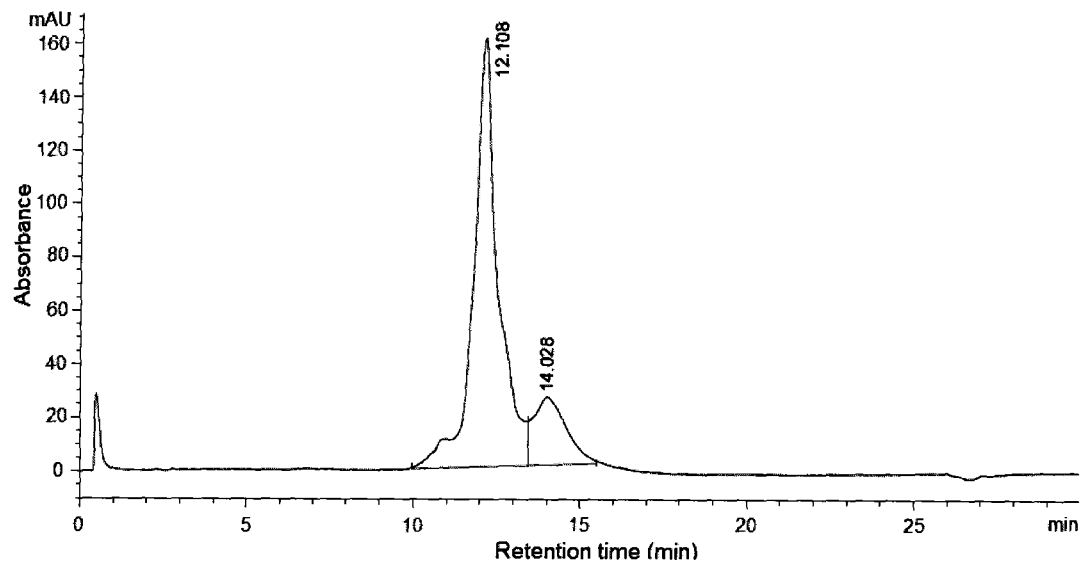
Figure 3H:
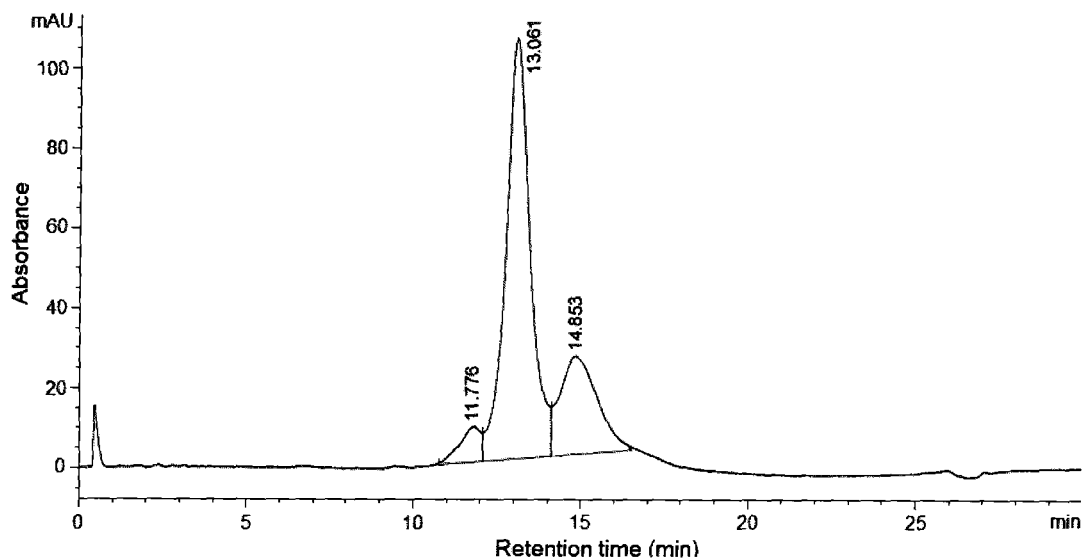
Figure 3I:
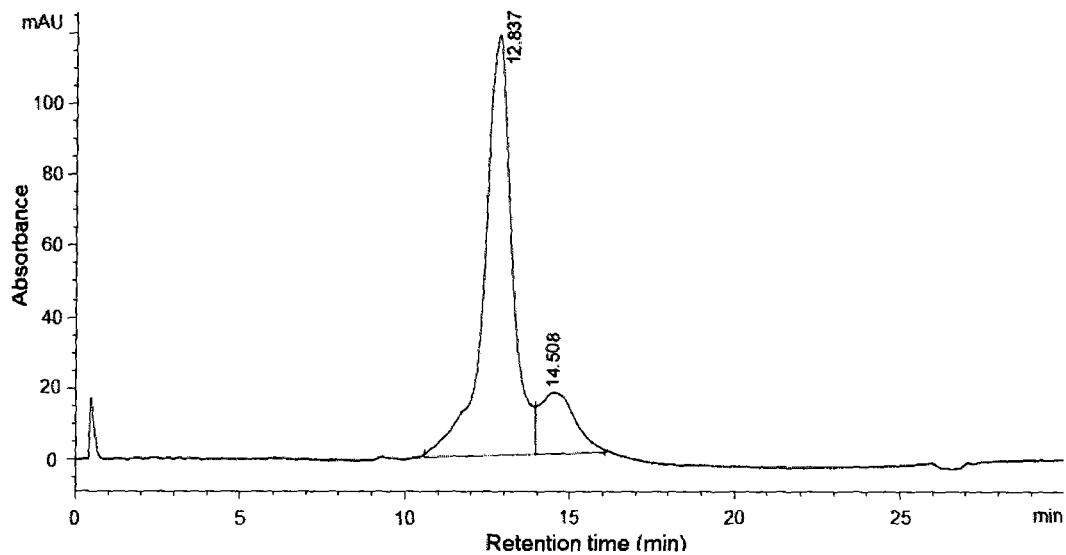
Figure 3J:
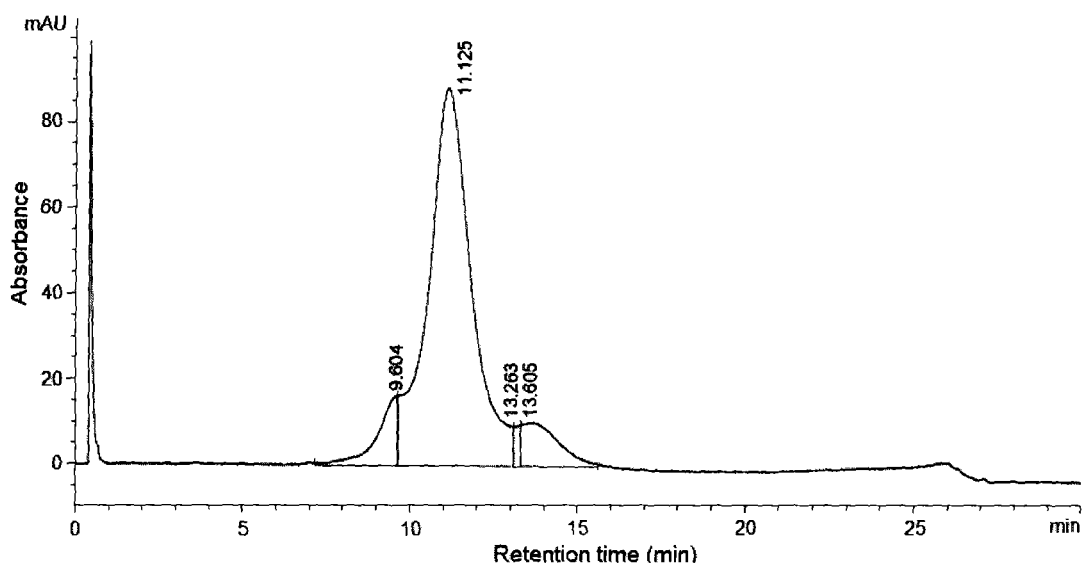
Figure 3K:
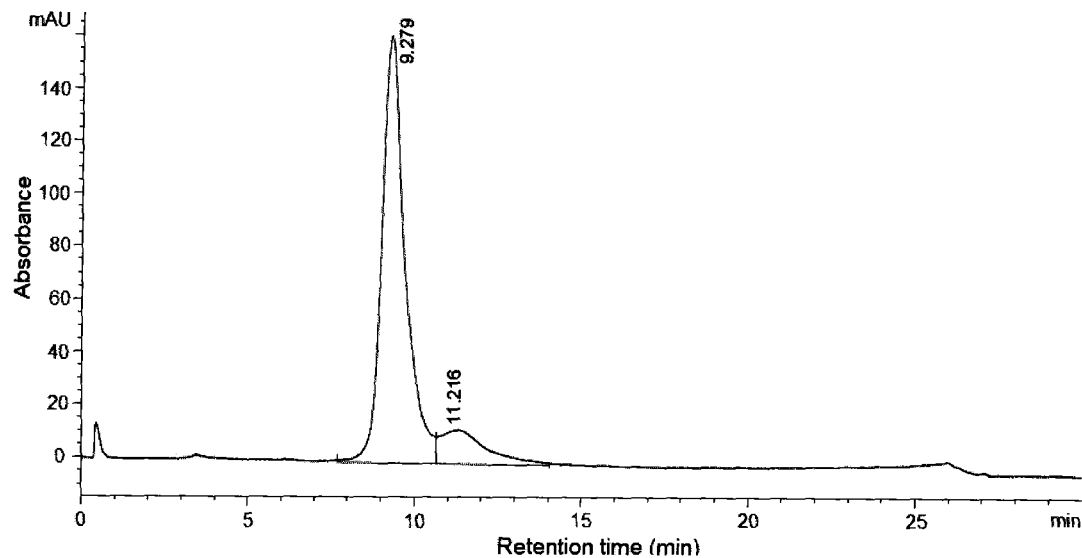
Figure 3L:
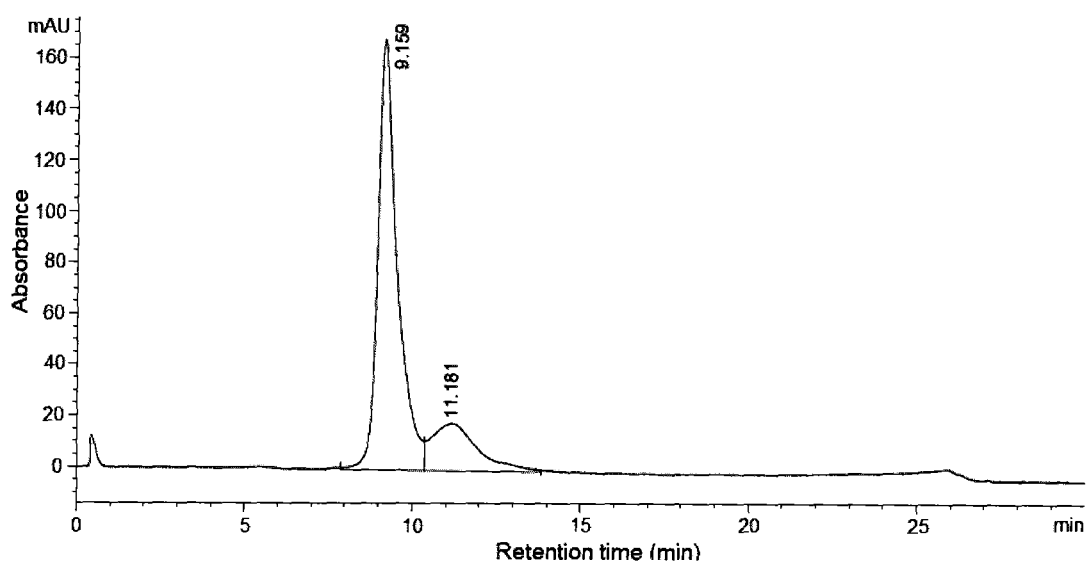

The SDS-PAGE results are shown in FIGS. 2a-2b, which shows that the main components in sample H-1-vcMMAE to H-12-vcMMAE were full antibody HHLL (full ADC) and half antibody HL (full ADC lost heavy chain interaction). The result proves that the oxadiazole linkers of the invention can crosslink the inter chains of the reduced antibody, and thus effectively control the number of drugs per antibody (DAR).

4) Hydrophobic Interaction Chromatography (HIC) Analysis

HIC was measured on an Agilent 1100 chromatograph. TSKgel butyl-NPR column (4.6×35 mm, 2.5 m, Tosoh Bioscience Shanghai) was applied as the immobile phase. The method was consisted of a linear gradient from 100% buffer A (50 mM potassium phosphate (pH 7.0)+1.5 M ammonium sulfate) to 100% buffer B (80% v/v 50 mM sodium phosphate (pH 7.0), 20% v/v isopropanol) over 25 minutes. The flow rate was 0.8 mL/min, the column temperature was 30° C., and the detection wavelengths were 230 and 280 nm.

HIC analysis results are shown in FIGS. 3a-3l, which show that the main components of the ADC samples, H-1-vcMMAE to H-9-vcMMAE, are DARt=4 components. The main components of the ADC sample, H-10-vcMMAE, is DARt=3 component. The main components of the ADC samples, H-11-vcMMAE to H-12-vcMMAE, are DARt=2 components. The result proves that the oxadiazole linkers of the invention could be used to effectively control the DAR and distribution of the ADC product.

Test Example 1

Determination of the Antigen Binding Ability of the ADCs of the Invention by Enzyme-Linked Immunosorbent Assay (ELISA)

Indirect ELISA was used to analyze binding ability of the antibody or antibody-drug conjugate to the corresponding antigen. The Her2 antigen was immobilized on a solid-phase support (96 well microplate) by coating to form a solid-phase antigen, and then unbound antigen was removed by washing. Serial dilutions of test antibody or antibody-drug conjugate were added, wherein specific antibody or antibody-drug conjugate bound to the antigen and formed solid-phase antigen-antibody complexes. The antibody or antibody-drug conjugate unbound to the solid-phase antigen was removed by washing. The enzyme labeled anti-antibody was added to bind to the above-formed complexes. After washing, substrate solution was added, and the optical density was read by a microplate reader at 450 nm/630 nm, based on which the curve was drawn and the $EC_{50}$ was calculated.

The binding abilities of the ADCs of the invention to Her2 antigen were listed in Table 3.

TABLE 3

The binding ability of the ADCs of the invention to Her2 antigen

| Antibody/ADCs | $EC_{50}$ (ng/mL) |
| --- | --- |
| H | 33.5 |
| H-1-vcMMAE | 70.8 |
| H-2-vcMMAE | 79.6 |
| H-3-vcMMAE | 63.8 |
| H-4-vcMMAE | 66.1 |
| H-5-vcMMAE | 59.0 |
| H-6-vcMMAE | 70.8 |
| H-7-vcMMAE | 95.9 |
| H-8-vcMMAE | 83.3 |
| H-9-vcMMAE | 62.5 |
| H-10-vcMMAE | 34.4 |
| H-11-vcMMAE | ND |
| H-12-vcMMAE | ND |

ND: not determined.

As shown in Table 3, compared to naked antibody, the binding ability of the ADCs prepared from oxadiazole linkers to the antigen shows no significant difference.

Test Example 2

Cell Proliferation Inhibition of the ADCs of the Invention
Cell Proliferation Assay Cell proliferation inhibition of an antibody or ADC is measured by the following method. Mammalian cells expressing tumor-associated antigens or receptor proteins (Her2 expressing breast cancer cell, SK-BR-3, was used in this assay) were seed in 96-well plate at a concentration of 8000 cells/well, and the cells were suspended in DMEM (GIBCO). The initial ADC concentration was 2 μg/mL, which was 3 times gradient diluted with DMEM containing 2% FBS (GIBCO). The initial cell culture media was removed and 200 μL of ADC was added to each well. The cells were incubated for 72 h, and the media was removed. 100 μL of CCK-8 was added, followed by incubation of 30 min. The absorption was read by a microplate reader at 450 nm/630 nm, based on which the curve was drawn and the $IC_{50}$ was calculated.

The cell proliferation inhibition result of the ADCs of the invention was listed in table 4.

TABLE 4

Cell Proliferation Inhibition Result of the ADCs of the Invention

| ADC | $IC_{50}$ (ng/mL) |
| --- | --- |
| H-1-vcMMAE | 3.0 |
| H-2-vcMMAE | 3.3 |
| H-3-vcMMAE | 3.2 |
| H-4-vcMMAE | 3.0 |
| H-5-vcMMAE | 2.7 |
| H-6-vcMMAE | 2.5 |
| H-7-vcMMAE | 5.4 |
| H-8-vcMMAE | 2.8 |
| H-9-vcMMAE | 3.5 |
| H-10-vcMMAE | 3.2 |
| H-11-vcMMAE | 6.1 |
| H-12-vcMMAE | 6.3 |

Table 4 shows that the ADCs of the invention have excellent cell proliferation inhibition activity.

All references mentioned in the present application are incorporated herein by reference to the same extent as if each individual reference is individually incorporated by reference. In addition, it should be understood that after reading the present invention, those skilled in the art can make various changes or modifications to the present invention, and these equivalent forms also fall within the scope defined by the appended claims of the present application.

What is claimed is:
1. A compound of formula I,

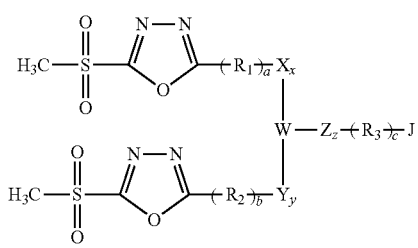

and pharmaceutically acceptable salts thereof,
wherein
W is selected from N, $CR_{11}$ and aryl;
X, Y and Z are each independently selected from O, C(=O), C(=O)$NR_{12}$, $NR_{13}$C(=O), $NR_{14}$C(=O)$NR_{15}$, $NR_{16}$C(=O)O and OC(=O)$NR_{17}$;
J is selected from —COOH, —OH and —$NHR_{18}$;
a, b, c, x, y and z are each independently selected from 0 and 1;
$R_1$, $R_2$ and $R_3$ are each independently selected from $C_1$-$C_8$ alkylene and $C_1$-$C_8$ alkylene containing O in the backbone;
$R_{11}$, $R_{12}$, $R_{13}$, $R_{14}$, $R_{15}$, $R_{16}$, $R_{17}$ and $R_{18}$ are each independently selected from H and $C_1$-$C_8$ alkyl.
2. The compound of formula I according to claim 1 and pharmaceutically acceptable salts thereof, wherein:
W is selected from N, CH and $C_6$-$C_{10}$ aryl.

3. The compound of formula I according to claim 1 and pharmaceutically acceptable salts thereof, wherein:
   a, b, x and y are 0; or
   a is 0, b is 1, while x and y are 0; or
   a is 1, b is 0, while x and y are 0; or
   a and b are 1, while x and y are 0; or
   a and b are 1, while x and y are 1.

4. The compound of formula I according to claim 1 and pharmaceutically acceptable salts thereof, wherein:
   c is 0 or 1.

5. The compound of formula I according to claim 1 and pharmaceutically acceptable salts thereof, wherein:
   $R_1$ and $R_2$ are each independently selected from $C_1$-$C_4$ alkylene and $C_1$-$C_4$ alkylene containing O in the backbone.

6. The compound of formula I according to claim 1 and pharmaceutically acceptable salts thereof, wherein:
   $R_3$ is selected from $C_1$-$C_8$ alkylene and $C_1$-$C_8$ alkylene containing O in the backbone.

7. The compound of formula I according to claim 1 and pharmaceutically acceptable salts thereof, wherein:
   Z is selected from O, C(=O), C(=O)$NR_{12}$ and $NR_{13}$C(=O), wherein $R_{12}$ and $R_{13}$ are as defined in claim 1.

8. The compound of formula I according to claim 1 and pharmaceutically acceptable salts thereof, wherein:
   J is —COOH.

9. The compound of formula I according to claim 1 and pharmaceutically acceptable salts thereof, wherein the compound is selected from the group consisting of compounds 1-9:

1
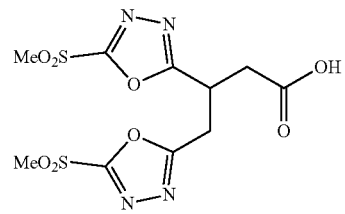

2
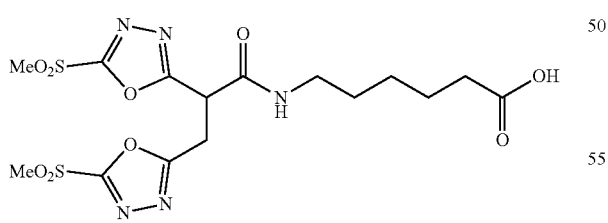

3
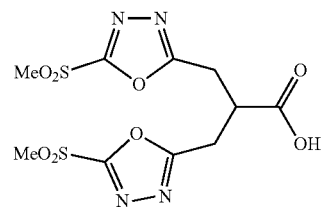

-continued

4
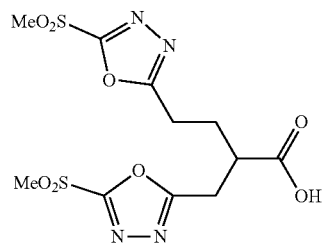

5
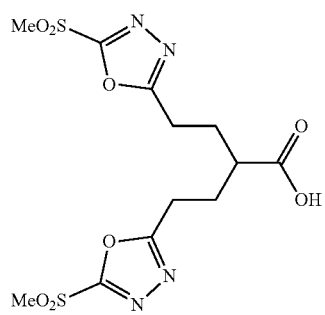

6
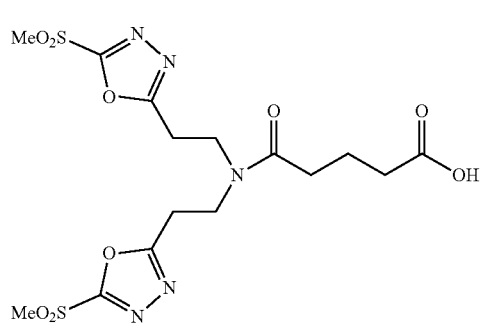

7
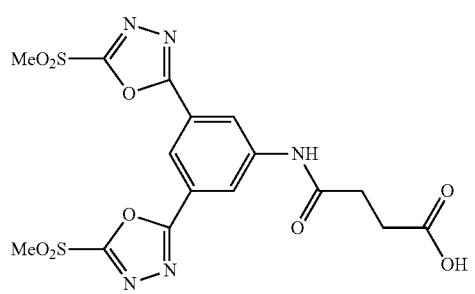

8
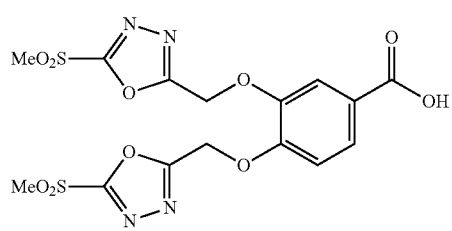

-continued

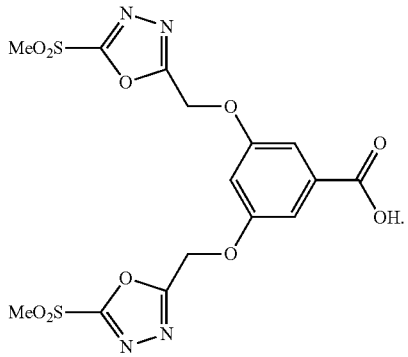

10. A compound of formula II,

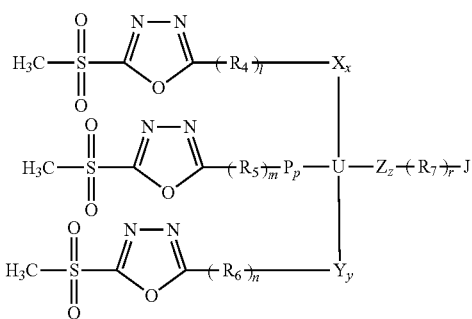

and pharmaceutically acceptable salts thereof, wherein
U is selected from C and aryl;
X, Y, P and Z are each independently selected from O, C(=O), C(=O)NR$_{12}$, NR$_{13}$C(=O), NR$_{14}$C(=O)NR$_{15}$, NR$_{16}$C(=O)O and OC(=O)NR$_{17}$;
J is selected from —COOH, —OH and —NHR$_{18}$;
l, m, n, r, x, y and z are each independently selected from 0 and 1;
R$_4$, R$_5$, R$_6$ and R$_7$ are each independently selected from C$_1$-C$_8$ alkylene and C$_1$-C$_8$ alkylene containing O in the backbone;
R$_{12}$, R$_{13}$, R$_{14}$, R$_{15}$, R$_{16}$, R$_{17}$ and R$_{18}$ are each independently selected from H and C$_1$-C$_8$ alkyl.

11. The compound of formula II according to claim 10 and pharmaceutically acceptable salts thereof, wherein:
U is C$_6$-C$_{10}$ aryl.

12. The compound of formula II according to claim 10 and pharmaceutically acceptable salts thereof, wherein:
X, Y and P are each independently selected from O, C(=O), C(=O)NR$_{12}$ and NR$_{13}$C(=O), wherein R$_{12}$ and R$_{13}$ are defined as in claim 10.

13. The compound of formula II according to claim 10 and pharmaceutically acceptable salts thereof, wherein:
Z is selected from O, C(=O), C(=O)NR$_{12}$ and NR$_{13}$C(=O), wherein R$_{12}$ and R$_{13}$ are as defined in claim 10.

14. The compound of formula II according to claim 10 and pharmaceutically acceptable salts thereof, wherein:
R$_4$, R$_5$ and R$_6$ are each independently selected from C$_1$-C$_4$ alkylene and C$_1$-C$_4$ alkylene containing O in the backbone.

15. The compound of formula II according to claim 10, wherein:
R$_7$ is selected from C$_1$-C$_4$ alkylene and C$_1$-C$_4$ alkylene containing O in the backbone.

16. The compound of formula II according to claim 10, wherein:
J is —COOH.

17. The compound of formula II according to claim 10 and pharmaceutically acceptable salts thereof, wherein the compound is:

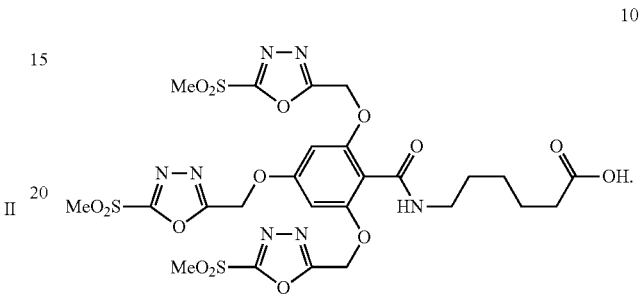

18. A compound of formula III,

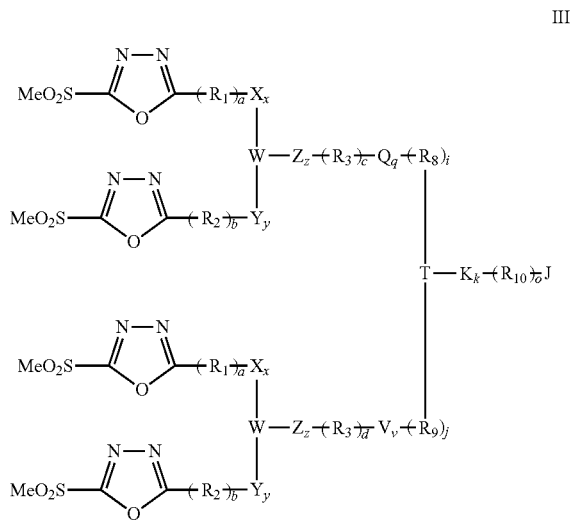

and pharmaceutically acceptable salts thereof, wherein
T is selected from N, CR$_{11}$ and aryl;
X, Y, Z and K are each independently selected from O, C(=O), C(=O)NR$_{12}$, NR$_{13}$C(=O), NR$_{14}$C(=O)NR$_{15}$, NR$_{16}$C(=O)O and OC(=O)NR$_{17}$;
Q and V are each independently selected from O, C(=O), C(=O)NR$_{12}$, NR$_{13}$C(=O) and OC(=O);
a, b, c, d, i, j, k, o, q, v, x, y and z are each independently selected from 0 and 1;
R$_1$, R$_2$, R$_3$, R$_8$, R$_9$ and R$_{10}$ are each independently selected from C$_1$-C$_8$ alkylene and C$_1$-C$_8$ alkylene containing O in the backbone;
R$_{11}$, R$_{12}$, R$_{13}$, R$_{14}$, R$_{15}$, R$_{16}$ and R$_{17}$ are each independently selected from H and C$_1$-C$_8$ alkyl.

19. The compound of formula III according to claim 18 and pharmaceutically acceptable salts thereof, wherein:
T is selected from N and C$_6$-C$_{10}$ aryl.

20. The compound of formula III according to claim 18 and pharmaceutically acceptable salts thereof, wherein:

$R_8$ and $R_9$ are each independently selected from $C_1$-$C_4$ alkylene and $C_1$-$C_4$ alkylene containing O in the backbone.

21. The compound of formula III according to claim 18 and pharmaceutically acceptable salts thereof, wherein:

$R_{10}$ is selected from $C_1$-$C_8$ alkylene and $C_1$-$C_8$ alkylene containing O in the backbone.

22. The compound of formula III according to claim 18 and pharmaceutically acceptable salts thereof, wherein:

Q and V are each independently selected from C(=O)$NR_{12}$, $NR_{13}$C(=O) and OC(=O), wherein $R_{12}$ and $R_{13}$ are as defined in claim 18.

23. The compound of formula III according to claim 18 and pharmaceutically acceptable salts thereof, wherein:

K is selected from O, C(=O), C(=O)$NR_{12}$ and $NR_{13}$C(=O), wherein $R_{12}$ and $R_{13}$ are as defined in claim 18.

24. The compound of formula III according to claim 18 and pharmaceutically acceptable salts thereof, wherein:

$R_3$ is selected from $C_1$-$C_4$ alkylene and $C_1$-$C_4$ alkylene containing O in the backbone.

25. The compound of formula III according to claim 18 and pharmaceutically acceptable salts thereof, wherein:

$R_1$ and $R_2$ are each independently selected from $C_1$-$C_4$ alkylene and $C_1$-$C_4$ alkylene containing O in the backbone.

26. The compound of formula III according to claim 18 and pharmaceutically acceptable salts thereof, wherein:

J is —COOH.

27. The compound of formula III according to claim 18 and pharmaceutically acceptable salts thereof, wherein the compound is selected from:

28. A compound of formula IV,

B-A-D       IV wherein
B is a compound of formula I according to claim 1,
A is optionally other linker; and
D is a drug molecule;
wherein B is linked to A or D by reaction between a terminal J group of B and a terminal group of A or D.

29. An antibody-drug conjugate of formula V,

L-(B-A-D)$_n$       V wherein
L is an antibody or antibody fragment;
B is a compound of formula I according to claim 1;
A is optionally other linker;
D is a drug molecule; and
n is an integer of 1 to 8;
wherein B is linked to A or D by reaction between a terminal J group of B and a terminal group of A or D, and is linked to L by reaction between the cysteines or other amino acid residues of L and 1,3,4-oxadiazole groups.

30. A compound of formula IV according to claim 28, wherein A is optionally a cleavable or noncleavable linker other than a 1,3,4-oxadiazole linker.

31. A compound of formula IV according to claim 28, wherein A has a formula of C-$E_e$-$F_f$ or $G_g$:

wherein
C is a cleavable linker;
E and F are self-immolative linkers;
e and f are each independently selected from an integer of 0 to 5;
G is a noncleavable linker; and
g is an integer of 0 to 5.

32. An antibody-drug conjugate of formula V according to claim 29, wherein said antibody-drug conjugate has the formula VI wherein
L is an antibody or antibody fragment;
A is optionally a cleavable or noncleavable linker other than a 1,3,4-oxadiazole linker;
D is a drug molecule;
W is selected from N, $CR_{11}$ and aryl
X, Y, and Z are each independently selected from O, $C(=O)$, $C(=O)NR_{12}$, $NR_{13}C(=O)$, $NR_{14}C(=O)NR_{15}$, $NR_{16}C(=O)O$ and $OC(=O)NR_{17}$;
a, b, c, n, x, y and z are each independently selected from 0 and 1;
$R_1$, $R_2$, and $R_3$, are each independently selected from $C_1$-$C_8$ alkylene and $C_1$-$C_8$ alkylene containing O in the backbone;
$R_1$, $R_{12}$, $R_{13}$, $R_{14}$, $R_{15}$, $R_{16}$ and $R_{17}$ are each independently selected from H and $C_1$-$C_8$ alkyl, preferably $C_1$-$C_4$ alkyl.

33. An antibody-drug conjugate of formula V according to claim 29, wherein the antibody targets cell surface receptors or tumor-related antigens.

34. An antibody-drug conjugate of formula V according to claim 29, wherein the antibody is IgG1.

35. A compound of formula IV according to claim 28, wherein the drug is a cytotoxic drug, an anti-autoimmune disease drug, or an anti-inflammation drug.

36. A pharmaceutical composition comprising an antibody-drug conjugate of formula V according to claim 29 and a pharmaceutically acceptable carrier.

37. A method of treating a cancer, autoimmune disease or inflammatory disease, comprising administering to a patient in need thereof an effective amount of an antibody-drug conjugate of formula V according to claim 29.

38. A compound of formula IV,

B-A-D          IV wherein
B is a compound of formula II according claim 10;
A is optionally other linker; and
D is a drug molecule;
wherein B is linked to A or D by reaction between a terminal J group of B and a terminal group of A or D.

39. An antibody-drug conjugate of formula V,

L-(B-A-D)$_n$          V wherein
L is an antibody or antibody fragment;
B is a compound of formula I according to claim 10;
A is optionally other linker;
D is a drug molecule; and
n is an integer of 1 to 8;
wherein B is linked to A or D by reaction between a terminal J group of B and a terminal group of A or D, and is linked to L by reaction between the cysteines or other amino acid residues of L and 1,3,4-oxadiazole groups.

40. A compound of formula IV according to claim 38, wherein A is optionally a cleavable or noncleavable linker other than a 1,3,4-oxadiazole linker.

41. A compound of formula IV according to claim 38, wherein A has a formula of C-$E_e$-$F_f$ or $G_g$:
wherein
C is a cleavable linker;
E and F are self-immolative linkers;
e and f are each independently selected from an integer of 0 to 5;
G is a noncleavable linker; and
g is an integer of 0 to 5.

42. An antibody-drug conjugate of formula V according to claim 39, wherein said antibody-drug conjugate has the formula VII:

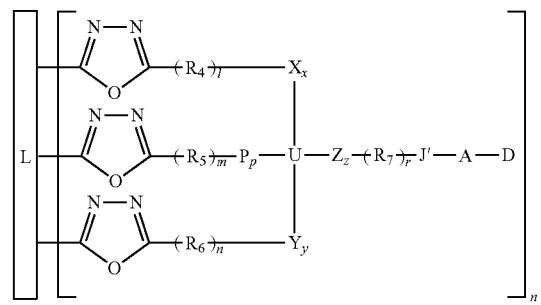

wherein
L is an antibody or antibody fragment;
A is optionally a cleavable or noncleavable linker other than a 1,3,4-oxadiazole linker;
D is a drug molecule;
U is selected from C and aryl;
X, Y, P, and Z are each independently selected from O, $C(=O)$, $C(=O)NR_{12}$, $NR_{13}C(=O)$, $NR_{14}C(=O)NR_{15}$, $NR_{16}C(=O)O$ and $OC(=O)NR_{17}$;
l, m, n, p, r, x, y and z are each independently selected from 0 and 1;
$R_4$, $R_5$, and $R_6$, are each independently selected from $C_1$-$C_8$ alkylene and $C_1$-$C_8$ alkylene containing O in the backbone;
$R_{11}$, $R_{12}$, $R_{13}$, $R_{14}$, $R_{15}$, $R_{16}$ and $R_{17}$ are each independently selected from H and $C_1$-$C_8$ alkyl, preferably $C_1$-$C_4$ alkyl.

43. An antibody-drug conjugate of formula V according to claim 39, wherein the antibody targets cell surface receptors or tumor-related antigens.

44. An antibody-drug conjugate of formula V according to claim 39, wherein the antibody is IgG1.

45. A compound of formula IV according to claim 38, wherein the drug is a cytotoxic drug, an anti-autoimmune disease drug, or an anti-inflammation drug.

46. A pharmaceutical composition comprising an antibody-drug conjugate of formula V according to claim 39 and a pharmaceutically acceptable carrier.

47. A method of treating a cancer, autoimmune disease or inflammatory disease, comprising administering to a patient in need thereof an effective amount of an antibody-drug conjugate of formula V according to claim 39.

48. A compound of formula IV,

B-A-D          IV wherein
B is a compound of formula III according to claim 18;
A is optionally other linker; and
D is a drug molecule;
wherein B is linked to A or D by reaction between a terminal J group of B and a terminal group of A or D.

49. An antibody-drug conjugate of formula V,

L-(B-A-D)$_n$     V wherein
L is an antibody or antibody fragment;
B is a compound of formula III according to claim 18;
A is optionally other linker;
D is a drug molecule; and
n is an integer of 1 to 8;
wherein B is linked to A or D by reaction between a terminal J group of B and a terminal group of A or D, and is linked to L by reaction between the cysteines or other amino acid residues of L and 1,3,4-oxadiazole groups.

50. A compound of formula IV according to claim 48, wherein A is optionally a cleavable or noncleavable linker other than a 1,3,4-oxadiazole linker.

51. A compound of formula IV according to claim 48, wherein A has a formula of C-E$_e$-F$_f$ or G$_g$:
wherein
C is a cleavable linker;
E and F are self-immolative linkers;
e and f are each independently selected from an integer of 0 to 5;
G is a noncleavable linker; and
g is an integer of 0 to 5.

52. An antibody-drug conjugate of formula V according to claim 49, wherein said antibody-drug conjugate has the formula VIII:

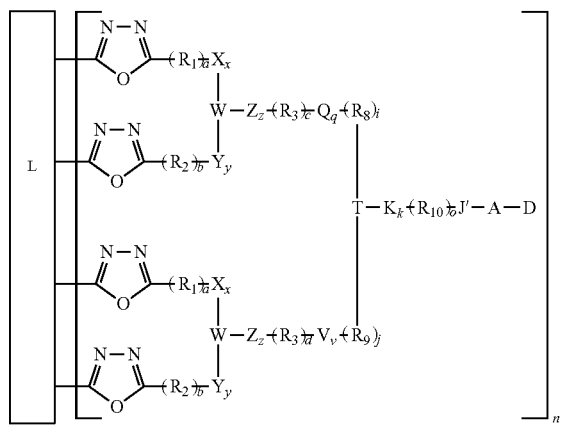

VII wherein
L is an antibody or antibody fragment;
A is optionally a cleavable or noncleavable linker other than a 1,3,4-oxadiazole linker;
D is a drug molecule;
W is selected from N, CR$_{11}$ and aryl;
T is selected from N, CR$_{12}$ and aryl;
X, Y, Z and K are each independently selected from O, C(=O), C(=O)NR$_{12}$, NR$_{13}$C(=O), NR$_{14}$C(=O)NR$_{15}$, NR$_{16}$C(=O)O and OC(=O)NR$_{17}$;
Q and V are each independently selected from O, C(=O), C(=O)NR$_{12}$, NR$_{13}$C(=O) and OC(=O);
a, b, c, d, i, j, k, n, o, q, v, x, y and z are each independently selected from 0 and 1;
R$_1$, R$_2$, R$_3$, R$_8$, R$_9$ and R$_{10}$ are each independently selected from C$_1$-C$_8$ alkylene and C$_1$-C$_8$ alkylene containing O in the backbone;
R$_{11}$, R$_{12}$, R$_{13}$, R$_{14}$, R$_{15}$, R$_{16}$ and R$_{17}$ are each independently selected from H and C$_1$-C$_8$ alkyl, preferably C$_1$-C$_4$ alkyl.

53. An antibody-drug conjugate of formula V according to claim 49, wherein the antibody targets cell surface receptors or tumor-related antigens.

54. An antibody-drug conjugate of formula V according to claim 49, wherein the antibody is IgG1.

55. A compound of formula IV according to claim 28, wherein the drug is a cytotoxic drug, an anti-autoimmune disease drug, or an anti-inflammation drug.

56. A pharmaceutical composition comprising an antibody-drug conjugate of formula V according to claim 49 and a pharmaceutically acceptable carrier.

57. A method of treating a cancer, autoimmune disease or inflammatory disease, comprising administering to a patient in need thereof an effective amount of an antibody-drug conjugate of formula V according to claim 49.

* * * * *